US009404932B2

(12) United States Patent
Veidal et al.

(10) Patent No.: US 9,404,932 B2
(45) Date of Patent: *Aug. 2, 2016

(54) PATHOLOGY BIOMARKER ASSAY

(75) Inventors: Sanne S. Veidal, Ølstykke (DK);
Morten A. Karsdal, Copenhagen Ø
(DK); Diana J. Leeming, Copenhagen
SV (DK); Natasha Barascuk,
Copenhagen S (DK); Helene
Skjøt-Arkil, Copenhagen S (DK);
Efstathios Vassiliadis, Rødovre (DK)

(73) Assignee: Nordic Bioscience A/S, Herlev (DK)

( * ) Notice: Subject to any disclaimer, the term of this patent is extended or adjusted under 35 U.S.C. 154(b) by 1063 days.

This patent is subject to a terminal disclaimer.

(21) Appl. No.: 13/187,205

(22) Filed: Jul. 20, 2011

(65) Prior Publication Data
US 2012/0045781 A1 Feb. 23, 2012

Related U.S. Application Data

(63) Continuation-in-part of application No. 12/749,652, filed on Mar. 30, 2010, which is a continuation-in-part of application No. PCT/EP2008/064946, filed on Nov. 4, 2008.

(60) Provisional application No. 61/211,467, filed on Mar. 30, 2009, provisional application No. 61/289,081, filed on Dec. 22, 2009.

(30) Foreign Application Priority Data

Nov. 5, 2007 (GB) .................................... 0721713.6
Nov. 20, 2007 (GB) .................................... 0722748.1
Feb. 15, 2008 (GB) .................................... 0802814.4

(51) Int. Cl.
G01N 31/00 (2006.01)
G01N 33/53 (2006.01)
G01N 33/68 (2006.01)
C07K 14/78 (2006.01)
C12Q 1/37 (2006.01)

(52) U.S. Cl.
CPC ............ *G01N 33/6893* (2013.01); *C07K 14/78* (2013.01); *C12Q 1/37* (2013.01); *G01N 2333/4737* (2013.01); *G01N 2333/775* (2013.01); *G01N 2333/78* (2013.01); *G01N 2800/32* (2013.01)

(58) Field of Classification Search
CPC ..... A61K 38/00; A61K 39/00; G01N 33/582; G01N 22/6893; C07K 14/705; C07K 16/18
See application file for complete search history.

(56) References Cited

U.S. PATENT DOCUMENTS

| 6,703,219 B1 | 3/2004 | Potempa et al. |
| 2007/0099242 A1 | 5/2007 | Heinecke et al. |
| 2010/0209940 A1 | 8/2010 | Veidal et al. |
| 2010/0323377 A1 | 12/2010 | Karsdal et al. |

FOREIGN PATENT DOCUMENTS

| EP | 1182213 A1 | 2/2002 |
| WO | 99/24835 A2 | 5/1999 |
| WO | 99/61477 A2 | 12/1999 |
| WO | 02/088750 A2 | 11/2002 |
| WO | 2005/050224 A2 | 6/2005 |
| WO | 2005/124341 A2 | 12/2005 |
| WO | 2007/050661 A2 | 5/2007 |
| WO | 2009/059973 A3 | 5/2009 |

OTHER PUBLICATIONS

Tascilar et al. (Annals of Oncology 10,Suppl. 4:S107-S110, 1999).*
Tockman et al. (Cancer Research 52:2711s-2718s, 1992).*
Bigg et al., (The FEBS Journal, Mar. 2007; 274(5) pp. 1246-1255).*
Acharya PS, Zukas A, Chandan V, Katzenstein AL, Pure E. Fibroblast activation protein: a serine protease expressed at the remodeling interface in idiopathic pulmonary fibrosis. Hum Pathol 2006;37:352-360.
Adams LA, Bulsara M, Rossi E, DeBoer B, Speers D, George J, Kench J, Farrell G, McCaughan GW, Jeffrey GP. Hepascore: an accurate validated predictor of liver fibrosis in chronic hepatitis C infection. Clin Chem 2005;51:1867-1873.
Attallah AM, Toson EA, Shiha GE, Omran MM, bdel-Aziz MM, El-Dosoky I. Evaluation of serum procollagen aminoterminal propeptide III, laminin, and hydroxyproline as predictors of severe fibrosis in patients with chronic hepatitis C. J Immunoassay Immunochem 2007;28:199-211.
Bartlett AH, Hayashida K, Park PW. Molecular and cellular mechanisms of syndecans in tissue injury and inflammation. Mol Cells 2007;24:153-166.
Bay-Jensen AC, Hoegh-Madsen S, Dam E, Henriksen K, Sondergaard BC, Pastoureau P, et al. Which elements are involved in reversible and irreversible cartilage degradation in osteoarthritis? Rheumatol Int Feb. 2010;30(4):435-442.
Beliveau et al; Genes and Development 24:2800-2811; 2010.

(Continued)

*Primary Examiner* — Lisa Cook
(74) *Attorney, Agent, or Firm* — Benjamin Aaron Adler

(57) ABSTRACT

Methods of diagnosis or of quantitation of pathological conditions comprise conducting an immunoassay to measure neo-epitope containing protein fragments naturally present in a biofluid sample, and associating an elevation of the measure in the patient above a normal level with the presence or extent of pathology. The immunoassay is conducted by a method comprising: contacting protein fragments naturally present in the sample with an immunological binding partner reactive with a neo-epitope formed by cleavage of a protein by a proteinase and measuring the extent of binding of peptide fragments to the immunological binding partner to measure therein protein fragments comprising the neo-epitope. Neo-epitopes from, collagen type I, collagen type III, collagen type IV, collagen type V, collagen type VI, elastin, biglycan, decorin, lumican, versican, C-reactive protein, ApoE and laminins are described.

7 Claims, 1 Drawing Sheet

(56) References Cited

OTHER PUBLICATIONS

Figure 1:
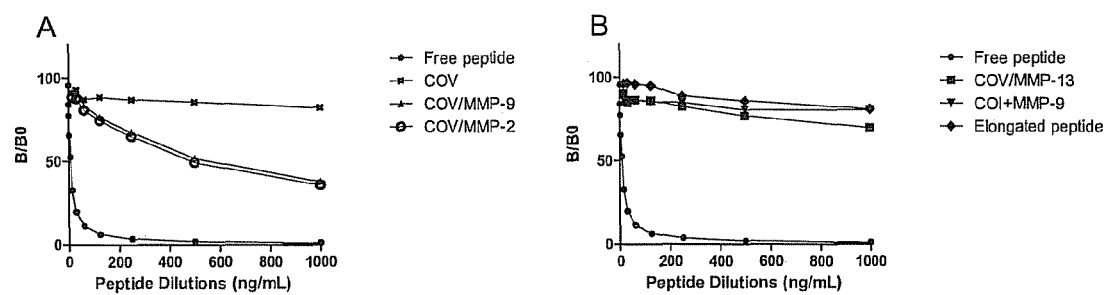

Benyon RC, Arthur MJ. Extracellular matrix degradation and the role of hepatic stellate cells. Semin Liver Dis 2001;21:373-384.
Berendsen AD, Bronckers AL, Smit TH, Walboomers XF, Everts V. Collagen type V enhances matrix contraction by human periodontal ligament fibroblasts seeded in three-dimensional collagen gels. Matrix Biol Oct. 2006;25(8):515-522.
Birk DE, Fitch JM, Babiarz JP, Linsenmayer TF. Collagen type I and type V are present in the same fibril in the avian corneal stroma. J Cell Biol Mar. 1988;106(3):999-1008.
Blochberger TC, Cornuet PK, Hassell JR. Isolation and partial characterization of lumican and decorin from adult chicken corneas. A keratan sulfate-containing isoform of decorin is developmentally regulated. J Biol Chem 1992;267:20613-20619.
Bobryshev YV. Calcification of elastic fibers in human atherosclerotic plaque. Atherosclerosis 2005;180:293-303.
Boeker KH, Haberkorn CI, Michels D, Flemming P, Manns MP, Lichtinghagen R. Diagnostic potential of circulating TIMP-1 and MMP-2 as markers of liver fibrosis in patients with chronic hepatitis C. Clin Chim Acta Feb. 2002;316(1-2):71-81.
Bourliere M, Penaranda G, Renou C, Botta-Fridlund D, Tran A, Portal I, Lecomte L, Castellani P, Rosenthal-Allieri MA, Gerolami R, Ouzan D, Deydier R, Degott C, Halfon P. Validation and comparison of indexes for fibrosis and cirrhosis prediction in chronic hepatitis C patients: proposal for a pragmatic approach classification without liver biopsies. J Viral Hepat 2006;13:659-670.
Braun J, Pincus T. Mortality, course of disease and prognosis of patients with ankylosing spondylitis. Clin Exp Rheumatol Nov. 2002;20(6 Suppl 28):S16-S22.
Brown, D. C. and K. G. Vogel. "Characteristics of the in vitro interaction of a small proteoglycan (PG II) of bovine tendon with type I collagen." Matrix. 9.6 (1989): 468-78.
Cacoub P, Carrat F, Bedossa P, Lambert J, Penaranda G, Perronne C, Pol S, Halfon P. Comparison of non-invasive liver fibrosis biomarkers in HIV/HCV co-infected patients: the fibrovic study—ANRS HC02. J Hepatol 2008;48:765-773.
Cales P, Laine F, Boursier J, Deugnier Y, Moal V, Oberti F, Hunault G, Rousselet MC, Hubert I, Laafi J, Ducluzeaux PH, Lunel F. Comparison of blood tests for liver fibrosis specific or not to NAFLD. J Hepatol 2008.
Camacho VR, Silveira TR, Oliveira JR, Barros SG, Cerski CT. Relationship between serum concetrations of type III procollagen, hyluronic acid and histopathological findings in the liver of HCV-positive blood donors. Arq Gastroenterol 2007;44:118-122.
Carvalho-Filho RJ, Schiavon LL, Narciso-Schiavon JL, Sampaio JP, Lanzoni VP, Ferraz ML, Silva AE. Optimized cutoffs improve performance of the aspartate aminotransferase to platelet ratio index for predicting significant liver fibrosis in human immunodeficiency virus/hepatitis C virus co-infection. Liver Int 2008;28:486-493.
Castera L, Vergniol J, Foucher J, Le BB, Chanteloup E, Haaser M, Darriet M, Couzigou P, de L, V. Prospective comparison of transient elastography, Fibrotest, APRI, and liver biopsy for the assessment of fibrosis in chronic hepatitis C. Gastroenterology 2005;128:343-350.
Cattin L, Fisicaro M, Tonizzo M, Valenti M, Danek GM, Fonda M, Da Col PG, Casagrande S, Pincetri E, Bovenzi M, and Baralle F. Polymorphism of the apolipoprotein E gene and early carotid atherosclerosis defined by ultrasonography in asymptomatic adults. Arterioscler Thromb Vasc Biol. Jan. 1997;17(1):91-4.
Chapman HA, Riese RJ, Shi GP. Emerging roles for cysteine proteases in human biology. Annu.Rev.Physiol 1997;59:63-88.
Clarkson TB, Kaplan JR. Stage of Reproductive Life, Atherosclerosis Progression and Estrogen Effects on Coronary Artery Atherosclerosis, In: Lobo RA, editor. Treatment of the Postmenopausal Woman: Basic and Clinical Aspects, 3 ed. San Diego: Elsevier; 2007. p. 509-28.
Danielson, K. G., et al. "Targeted disruption of decorin leads to abnormal collagen fibril morphology and skin fragility." J.Cell Biol. 136.3 (1997): 729-43.
Dours-Zimmermann, M. T. and D. R. Zimmermann. "A novel glycosaminoglycan attachment domain identified in two alternative splice variants of human versican." J.Biol.Chem. 269.52 (1994): 32992-98.
Eriksen HA, Satta J, Risteli J, Veijola M, Vare P, Soini Y. Type I and type III collagen synthesis and composition in the valve matrix in aortic valve stenosis. Atherosclerosis 2006;189:91-98.
Evanko, S. P., et al. "Proteoglycan distribution in lesions of atherosclerosis depends on lesion severity, structural characteristics, and the proximity of platelet-derived growth factor and transforming growth factor-beta." Am.J.Pathol. 152.2 (1998): 533-46.
Farkkila M, Rautiainen H, Karkkainen P, Karvonen AL, Nurmi H, Niemela O. Serological markers for monitoring disease progression in noncirrhotic primary biliary cirrhosis on ursodeoxycholic acid therapy. Liver Int 2008;28:787-797.
Fisher LW, Termine JD, Young MF. Deduced protein sequence of bone small proteoglycan I (biglycan) shows homology with proteoglycan II (decorin) and several nonconnective tissue proteins in a variety of species. J Biol Chem 1989;264:4571-4576.
Forns X, Ampurdanes S, Llovet JM, Aponte J, Quinto L, Martinez-Bauer E, Bruguera M, Sanchez-Tapias JM, Rodes J. Identification of chronic hepatitis C patients without hepatic fibrosis by a simple predictive model. Hepatology 2002;36:986-992.
Friedman SL. Mechanisms of disease: Mechanisms of hepatic fibrosis and therapeutic implications. Nat Clin Pract Gastroenterol Hepatol 2004;1:98-105.
Funderburgh, J. L. "Keratan sulfate: structure, biosynthesis, and function." Glycobiology 10.10 (2000): 951-58.
Funderburgh, J. L., et al. "Macrophage receptors for lumican. A corneal keratan sulfate proteoglycan." Invest Ophthalmol.Vis.Sci. 38.6 (1997): 1159-67.
Gabay C, Kushner I. Acute-phase proteins and other systemic responses to inflammation. N Engl J Med 1999;340:448-454.
Gagliano N, Arosio B, Grizzi F, Masson S, Tagliabue J, Dioguardi N, Vergani C, Annoni G. Reduced collagenolytic activity of matrix metalloproteinases and development of liver fibrosis in the aging rat. Mech Ageing Dev 2002;123:413-425.
Gardner CD, Fortmann SP, Krauss RM. Association of small low-density lipoprotein particles with the incidence of coronary artery disease in men and women. JAMA 1996;276:875-81.
Garrone R, Lethias C, Le Guellec D. Distribution of minor collagens during skin development. Microsc Res Tech 1997;38:407-412.
Gefter ML, Margulies DH, Scharff MD. A simple method for polyethylene glycol-promoted hybridization of mouse myeloma cells. Somatic Cell Genet Mar. 1977;3(2):231-236.
Gelse K, Poschl E, Aigner T. Collagens—structure, function, and biosynthesis. Adv Drug Deliv Rev 2003;55:1531-1546.
Gilliam AC. Scleroderma. Curr Dir Autoimmun 2008;10:258-279.
Graham I, Atar D, Borch-Johnsen K, Boysen G, Burell G, Cifkova R et al. European guidelines on cardiovascular disease prevention in clinical practice: executive summary. Atherosclerosis 2007;194:1-45.
Gressner AM, Weiskirchen R. Modern pathogenetic concepts of liver fibrosis suggest stellate cells and TGF-beta as major players and therapeutic targets. J Cell Mol Med 2006;10:76-99.
Gressner OA, Weiskirchen R, Gressner AM. Biomarkers of hepatic fibrosis, fibrogenesis and genetic pre-disposition pending between fiction and reality. J Cell Mol Med 2007;11:1031-1051.
Gressner OA, Weiskirchen R, Gressner AM. Biomarkers of liver fibrosis: clinical translation of molecular pathogenesis or based on liver-dependent malfunction tests. Clin Chim Acta 2007;381:107-113.
Grigorescu M, Rusu M, Neculoiu D, Radu C, Serban A, Catanas M, Grigorescu MD. The FibroTest value in discriminating between insignificant and significant fibrosis in chronic hepatitis C patients. The Romanian experience. J Gastrointestin Liver Dis 2007;16:31-37.
Guanabens N, Pares A, Alvarez L, Martinez de Osaba MJ, Monegal A, Peris P, Ballesta AM, Rodes J. Collagen-related markers of bone turnover reflect the severity of liver fibrosis in patients with primary biliary cirrhosis. J Bone Miner Res 1998;13:731-738.
Guechot J, Poupon RE, Giral P, Balkau B, Giboudeau J, Poupon R. Relationship between procollagen III aminoterminal propeptide and

(56) References Cited

OTHER PUBLICATIONS hyaluronan serum levels and histological fibrosis in primary biliary cirrhosis and chronic viral hepatitis C. J Hepatol 1994;20:388-393.

Guo J, Friedman SL. Hepatic fibrogenesis. Semin Liver Dis 2007;27:413-426.

Halfon P, Bacq Y, De MA, Penaranda G, Bourliere M, Ouzan D, Tran A, Botta D, Renou C, Brechot MC, Degott C, Paradis V. Comparison of test performance profile for blood tests of liver fibrosis in chronic hepatitis C. J Hepatol 2007;46:395-402.

Halfon P, Bourliere M, Deydier R, Botta-Fridlund D, Renou C, Tran A, Portal I, Allemand I, Bertrand JJ, Rosenthal-Allieri A, Rotily M, Sattonet C, Benderitter T, Saint Paul MC, Bonnot HP, Penaranda G, Degott C, Masseyeff MF, Ouzan D. Independent prospective multicenter validation of biochemical markers (fibrotest-actitest) for the prediction of liver fibrosis and activity in patients with chronic hepatitis C: the fibropaca study. Am J Gastroenterol 2006;101:547-555.

Haraki T, Takegoshi T, Kitoh C, Wakasugi T, Saga T, Hirai JI, Aoyama T, Inazu A and Mabuchi H, Carotid artery intima-media thickness and brachial artery flow-mediated vasodilation in asymptomatic Japanese male subjects amongst apolipoprotein E phenotypes. J Intern Med. Aug. 2002;252(2):114-20.

Hatanaka K, Li XA, Masuda K, Yutani C and Yamamoto A, Immunohistochemical localization of C-reactive protein-binding sites in human atherosclerotic aortic lesions by a modified streptavidin-biotin-staining method. Pathol Int. Sep. 1995;45(9):635-41.

Heegaard AM, Corsi A, Danielsen CC, Nielsen KL, Jorgensen HL, Riminucci M, Young MF and Bianco P, Biglycan deficiency causes spontaneous aortic dissection and rupture in mice. Circulation. May 29, 2007;115(21):2731-8. Epub May 14, 2007.

Heinegard D, Oldberg A. Structure and biology of cartilage and bone matrix noncollagenous macromolecules. FASEB J 1989;3:2042-2051.

Hemmann S, Graf J, Roderfeld M, Roeb E. Expression of MMPs and TIMPs in liver fibrosis—a systematic review with special emphasis on anti-fibrotic strategies. J Hepatol May 2007;46(5):955-975.

Herman MP, Sukhova GK, Libby P, Gerdes N, Tang N, Horton DB et al. Expression of neutrophil collagenase (matrix metalloproteinase-8) in human atheroma: a novel collagenolytic pathway suggested by transcriptional profiling. Circulation 2001;104:1899-904.

Hongbo L, Xiaohui L, Hong K, Wei W, Yong Z. Assessing routine and serum markers of liver fibrosis in CHB patients using parallel and serial interpretation. Clin Biochem 2007;40:562-566.

Hummers LK. Microvascular damage in systemic sclerosis: detection and monitoring with biomarkers. Curr Rheumatol Rep 2006;8:131-137.

Imbert-Bismut F, Ratziu V, Pieroni L, Charlotte F, Benhamou Y, Poynard T. Biochemical markers of liver fibrosis in patients with hepatitis C virus infection: a prospective study. Lancet 2001;357:1069-1075.

Iredale JP, Benyon RC, Arthur MJ, Ferris WF, Alcolado R, Winwood PJ, Clark N, Murphy G. Tissue inhibitor of metalloproteinase-1 messenger RNA expression is enhanced relative to interstitial collagenase messenger RNA in experimental liver injury and fibrosis. Hepatology 1996;24:176-184.

Jacqueminet S, Lebray P, Morra R, Munteanu M, Devers L, Messous D, Bernard M, Hartemann-Heurtier A, Imbert-Bismut F, Ratziu V, Grimaldi A, Poynard T. Screening for liver fibrosis by using a noninvasive biomarker in patients with diabetes. Clin Gastroenterol Hepatol 2008;6:828-831.

Jeppesen J, Hein HO, Suadicani P, Gyntelberg F. High triglycerides/low high-density lipoprotein cholesterol, ischemic electrocardiogram changes, and risk of ischemic heart disease. Am Heart J 2003;145:103-08.

Karsdal MA, Henriksen K, Leeming DJ, Mitchell P, Duffin K, Barascuk N, et al. Biochemical markers and the FDA Critical Path: how biomarkers may contribute to the understanding of pathophysiology and provide unique and necessary tools for drug development. Biomarkers May 2009;14(3):181-202.

Karsdal MA, Madsen SH, Christiansen C, Henriksen K, Fosang AJ, Sondergaard BC. Cartilage degradation is fully reversible in the presence of aggrecanase but not matrix metalloproteinase activity. Arthritis Res Ther 2008;10(3):R63.

Katsuda S, Okada Y, Minamoto T, Oda Y, Matsui Y, Nakanishi I. Collagens in human atherosclerosis. Immunohistochemical analysis using collagen type-specific antibodies. Arterioscler.Thromb. 1992;12:494-502.

Kiani C, Chen L, Wu YJ, Yee AJ, Yang BB. Structure and function of aggrecan. Cell Res 2002;12:19-32.

Kirimlioglu H, Kirimlioglu V, Yilmaz S. Expression of matrix metalloproteinases 2 and 9 in donor liver, cirrhotic liver, and acute rejection after human liver transplantation. Transplant Proc Dec. 2008;40(10):3574-3577.

Klappacher G, Franzen P, Haab D, Mehrabi M, Binder M, Plesch K, Pacher R, Grimm M, Pribill I, Eichler HG, . Measuring extracellular matrix turnover in the serum of patients with idiopathic or ischemic dilated cardiomyopathy and impact on diagnosis and prognosis. Am J Cardiol 1995;75:913-918.

Knox, S. M. and J. M. Whitelock. "Perlecan: how does one molecule do so many things?" Cell Mol.Life Sci. 63.21 (2006): 2435-45.

Koda M, Matunaga Y, Kawakami M, Kishimoto Y, Suou T, Murawaki Y. FibroIndex, a practical index for predicting significant fibrosis in patients with chronic hepatitis C. Hepatology 2007;45:297-306.

Krusius T, Gehisen KR, Ruoslahti E. A fibroblast chondroitin sulfate proteoglycan core protein contains lectin-like and growth factor-like sequences. J Biol Chem 1987;262:13120-13125.

Kuller LH, Tracy RP, Shaten J and Meilahn EN, Relation of C-reactive protein and coronary heart disease in the MRFIT nested case-control study. Multiple Risk Factor Intervention Trial. Am J Epidemiol. Sep. 15, 1996;144(6):537-47.

Kumar Vaakfn. Tissue renewal and repair: regeneration, healing, and fibrosis. Pathologic basis of disease.Philadelphia, Pennsylvania, USA: Elsevier Saunders, 2005. 87-118.

Kunz J. Matrix metalloproteinases and atherogenesis in dependence of age. Gerontology. 2007;53:63-73.

Kuzuya M, Nakamura K, Sasaki T, Cheng XW, Itohara S, Iguchi A. Effect of MMP-2 deficiency on atherosclerotic lesion formation in apoE-deficient mice. Arterioscler.Thromb.Vasc.Biol 2006;26:1120-25.

Laurent GJ. Dynamic state of collagen: pathways of collagen degradation in vivo and their possible role in regulation of collagen mass. Am J Physiol 1987;252:C1-C9.

Lawrie TD, Mcalpine SG, Rifkind BM, Robinson JF. Serum fatty-acid patterns in coronary-artery disease. Lancet 1961;1:421-24.

Lebensztejn DM, Sobaniec-Lotowska ME, Bauer M, Kaczmarski M, Voelker M, Schuppan D. Serum fibrosis markers as predictors of an antifibrotic effect of interferon alfa in children with chronic hepatitis B. Eur J Gastroenterol Hepatol 2005;17:843-848.

Lebensztejn DM, Sobaniec-Lotowska ME, Kaczmarski M, Voelker M, Schuppan D. Matrix-derived serum markers in monitoring liver fibrosis in children with chronic hepatitis B treated with interferon alpha. World J Gastroenterol 2006;12:3338-3343.

Lee KN, Jackson KW, Christiansen VJ, Lee CS, Chun JG, McKee PA. Antiplasmin-cleaving enzyme is a soluble form of fibroblast activation protein. Blood 2006;107:1397-1404.

Lein M, Wirth M, Miller K, Eickenberg HU, Weissbach L, Schmidt K, Haus U, Stephan C, Meissner S, Loening SA, Jung K. Serial Markers of Bone Turnover in Men with Metastatic Prostate Cancer Treated with Zoledronic Acid for Detection of Bone Metastases Progression. Eur Urol 2007.

Leinonen M and Saikku P, Evidence for infectious agents in cardiovascular disease and atherosclerosis. Lancet Infect Dis. Jan. 2002;2(1):11-7.

Leroy V, Halfon P, Bacq Y, Boursier J, Rousselet MC, Bourliere M, De MA, Sturm N, Hunault G, Penaranda G, Brechot MC, Trocme C, Cales P. Diagnostic accuracy, reproducibility and robustness of fibrosis blood tests in chronic hepatitis C: a meta-analysis with individual data. Clin Biochem 2008;41:1368-1376.

Leroy V, Hilleret MN, Sturm N, Trocme C, Renversez JC, Faure P, Morel F, Zarski JP. Prospective comparison of six non-invasive scores for the diagnosis of liver fibrosis in chronic hepatitis C. J Hepatol 2007;46:775-782.

(56) References Cited

OTHER PUBLICATIONS

Levy MT, McCaughan GW, Marinos G, Gorrell MD. Intrahepatic expression of the hepatic stellate cell marker fibroblast activation protein correlates with the degree of fibrosis in hepatitis C virus infection. Liver 2002;22:93-101.
Lieber CS, Weiss DG, Paronetto F. Value of fibrosis markers for staging liver fibrosis in patients with precirrhotic alcoholic liver disease. Alcohol Clin Exp Res 2008;32:1031-1039.
Lijnen,H.R. 2001. Plasmin and matrix metalloproteinases in vascular remodeling. Thromb. Haemost. 86:324-333.
Liu J, Sukhova GK, Sun JS, Xu WH, Libby P, Shi GP. Lysosomal cysteine proteases in atherosclerosis. Arterioscler.Thromb.Vasc.Biol 2004;24:1359-66.
Lochter A, Bissell MJ. An odyssey from breast to bone: multi-step control of mammary metastases and osteolysis by matrix metalloproteinases. APMIS Jan. 1999;107(1):128-136.
Lopez-Casillas F, Wrana JL, Massague J. Betaglycan presents ligand to the TGF beta signaling receptor. Cell 1993;73:1435-1444.
Lorenzo-Zuniga V, Bartoli R, Masnou H, Montoliu S, Morillas RM, Planas R. Serum concentrations of insulin-like growth factor-I (igf-I) as a marker of liver fibrosis in patients with chronic hepatitis C. Dig Dis Sci 2007;52:3245-3250.
Lutgens, S. P., et al. "Cathepsin cysteine proteases in cardiovascular disease." FASEB J. 21.12 (2007): 3029-41.
Manolakopoulos S, Bethanis S, Liapi C, Stripeli F, Sklavos P, Margeli A, Christidou A, Katsanika A, Vogiatzakis E, Tzourmakliotis D, Theocharis S. An assessment of serum leptin levels in patients with chronic viral hepatitis: a prospective study. BMC Gastroenterol 2007;7:17.
Marcellin P, Asselah T, Boyer N. Fibrosis and disease progression in hepatitis C. Hepatology 2002;36:S47-S56.
Mariat C. [Diagnosis and follow-up of chronic kidney graft dysfunction: from DFG to new biomarkers]. Nephrol Ther 2008;4 Suppl 3:S204-S207.
Martinez-Hernandez A, Amenta PS. The hepatic extracellular matrix. II. Ontogenesis, regeneration and cirrhosis. Virchows Arch A Pathol Anat Histopathol 1993;423:77-84.
Mayne R. Collagenous proteins of blood vessels. Arteriosclerosis. 1986;6:585-93.
Mays PK, McAnulty RJ, Campa JS, Laurent GJ. Age-related changes in collagen synthesis and degradation in rat tissues. Importance of degradation of newly synthesized collagen in regulating collagen production. Biochem J 1991;276 ( Pt 2):307-313.
McCullagh KG, Duance VC, Bishop KA. The distribution of collagen types I, III and V (AB) in normal and atherosclerotic human aorta. J Pathol 1980;130:45-55.
McHugh NJ, Distler O, Giacomelli R, Riemekasten G. Non organ based laboratory markers in systemic sclerosis. Clin Exp Rheumatol 2003;21:S32-S38.
McHutchison JG, Blatt LM, de Medina M, Craig JR, Conrad A, Schiff ER, Tong MJ. Measurement of serum hyaluronic acid in patients with chronic hepatitis C and its relationship to liver histology. Consensus Interferon Study Group. J Gastroenterol Hepatol 2000;15:945-951.
Mendall MA, Patel P, Ballam L, Strachan D and Northfield TC. C reactive protein and its relation to cardiovascular risk factors: a population based cross sectional study.,BMJ. Apr. 27, 1996;312(7038):1061-5.
Metwally MA, Zein CO, Zein NN. Predictors and noninvasive identification of severe liver fibrosis in patients with chronic hepatitis C. Dig Dis Sci 2007;52:582-588.
Meyer O. Prognostic markers for systemic sclerosis. Joint Bone Spine 2006;73:490-494.
Michalickova K, Susic M, Willing MC, Wenstrup RJ, Cole WG. Mutations of the alpha2(V) chain of type V collagen impair matrix assembly and produce ehlers-danlos syndrome type I. Hum Mol Genet Feb. 1998;7(2):249-255.
Mohamadnejad M, Montazeri G, Fazlollahi A, Zamani F, Nasiri J, Nobakht H, Forouzanfar MH, Abedian S, Tavangar SM, Mohamadkhani A, Ghoujeghi F, Estakhri A, Noun N, Farzadi Z, Najjari A, Malekzadeh R. Noninvasive markers of liver fibrosis and inflammation in chronic hepatitis B-virus related liver disease. Am J Gastroenterol 2006;101:2537-2545.
Moller S, Hansen M, Hillingso J, Jensen JE, Henriksen JH. Elevated carboxy terminal cross linked telopeptide of type I collagen in alcoholic cirrhosis: relation to liver and kidney function and bone metabolism. Gut 1999;44:417-423.
Monfort J, Nacher M, Montell E, Vila J, Verges J and Benito P, Chondroitin sulfate and hyaluronic acid (500-730 kda) inhibit stromelysin-1 synthesis in human osteoarthritic chondrocytes. Drugs Exp Clin Res. 2005;31(2):71-6.
Muller-Quernheim J. Serum markers for the staging of disease activity of sarcoidosis and other interstitial lung diseases of unknown etiology. Sarcoidosis Vasc Diffuse Lung Dis 1998;15:22-37.
Murasawa Y, Hayashi T, Wang PC. The role of type V collagen fibril as an ECM that induces the motility of glomerular endothelial cells. Exp Cell Res Dec. 10, 2008;314(20):3638-3653.
Myers RP, Tainturier MH, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003;39:222-230.
Naveau S, Raynard B, Ratziu V, Abella A, Imbert-Bismut F, Messous D, Beuzen F, Capron F, Thabut D, Munteanu M, Chaput JC, Poynard T. Biomarkers for the prediction of liver fibrosis in patients with chronic alcoholic liver disease. Clin Gastroenterol Hepatol 2005;3:167-174.
Ngo Y, Munteanu M, Messous D, Charlotte F, Imbert-Bismut F, Thabut D, Lebray P, Thibault V, Benhamou Y, Moussalli J, Ratziu V, Poynard T. A prospective analysis of the prognostic value of biomarkers (FibroTest) in patients with chronic hepatitis C. Clin Chem 2006;52:1887-1896.
Nunes D, Fleming C, Offner G, O'Brien M, Tumilty S, Fix O, Heeren T, Koziel M, Graham C, Craven DE, Stuver S, Horsburgh CR, Jr. HIV infection does not affect the performance of noninvasive markers of fibrosis for the diagnosis of hepatitis C virus-related liver disease. J Acquir Immune Defic Syndr 2005;40:538-544.
Olsen BR. Life without perlecan has its problems. J Cell Biol 1999;147:909-912.
Paggi S, Colli A, Fraquelli M, Vigano M, Del PP, Facciotto C, Colombo M, Ronchi G, Conte D. A non-invasive algorithm accurately predicts advanced fibrosis in hepatitis C: a comparison using histology with internal-external validation. J Hepatol 2008;49:564-571.
Parise ER, Oliveira AC, Figueiredo-Mendes C, Lanzoni V, Martins J, Nader H, Ferraz ML. Noninvasive serum markers in the diagnosis of structural liver damage in chronic hepatitis C virus infection. Liver Int 2006;26:1095-1099.
Pasceri V, Willerson JT and Yeh ET, Direct proinflammatory effect of C-reactive protein on human endothelial cells.Circulation. Oct. 31, 2000;102(18):2165-8.
Patel K, Gordon SC, Jacobson I, Hezode C, Oh E, Smith KM, Pawlotsky JM, McHutchison JG. Evaluation of a panel of non-invasive serum markers to differentiate mild from moderate-to-advanced liver fibrosis in chronic hepatitis C patients. J Hepatol 2004;41:935-942.
Patel K, Nelson DR, Rockey DC, Afdhal NH, Smith KM, Oh E, Hettinger K, Vallee M, Dev A, Smith-Riggs M, McHutchison JG. Correlation of FIBROSpect II with histologic and morphometric evaluation of liver fibrosis in chronic hepatitis C. Clin Gastroenterol Hepatol 2008;6:242-247.
Phan SH, Thrall RS. Pulmonary Fibrosis. Lung Biology in Health and Disease. 80 ed. New York: Marcel Dekker, Inc., 1995.
Poynard T, Imbert-Bismut F, Ratziu V, Chevret S, Jardel C, Moussalli J, Messous D, Degos F. Biochemical markers of liver fibrosis in patients infected by hepatitis C virus: longitudinal validation in a randomized trial. J Viral Hepat 2002;9:128-133.
Poynard T, Morra R, Halfon P, Castera L, Ratziu V, Imbert-Bismut F, Naveau S, Thabut D, Lebrec D, Zoulim F, Bourliere M, Cacoub P, Messous D, Munteanu M, de L, V. Meta-analyses of FibroTest diagnostic value in chronic liver disease. BMC Gastroenterol 2007;7:40.
Poynard T, Munteanu M, Imbert-Bismut F, Charlotte F, Thabut D, Le CS, Messous D, Thibault V, Benhamou Y, Moussalli J, Ratziu V.

(56) References Cited

OTHER PUBLICATIONS

Prospective analysis of discordant results between biochemical markers and biopsy in patients with chronic hepatitis C. Clin Chem 2004;50:1344-1355.

Poynard T, Zoulim F, Ratziu V, Degos F, Imbert-Bismut F, Deny P, Landais P, El HA, Slama A, Blin P, Thibault V, Parvaz P, Munteanu M, Trepo C. Longitudinal assessment of histology surrogate markers (FibroTest-ActiTest) during lamivudine therapy in patients with chronic hepatitis B infection. Am J Gastroenterol 2005;100:1970-1980.

Ratziu V, Massard J, Charlotte F, Messous D, Imbert-Bismut F, Bonyhay L, Tahiri M, Munteanu M, Thabut D, Cadranel JF, Le BB, de L, V, Poynard T. Diagnostic value of biochemical markers (FibroTest-FibroSURE) for the prediction of liver fibrosis in patients with non-alcoholic fatty liver disease. BMC Gastroenterol 2006;6:6.

Rauch U, Karthikeyan L, Maurel P, Margolis RU, Margolis RK. Cloning and primary structure of neurocan, a developmentally regulated, aggregating chondroitin sulfate proteoglycan of brain. J Biol Chem 1992;267:19536-19547.

Register TC, Cann JA, Kaplan JR, Williams JK, Adams MR, Morgan TM et al. Effects of soy isoflavones and conjugated equine estrogens on inflammatory markers in atherosclerotic, ovariectomized monkeys. J Clin Endocrinol Metab 2005;90:1734-40.

Reynolds GD and Vance RP. C-reactive protein immunohistochemical localization in normal and atherosclerotic human aortas. Arch Pathol Lab Med. Mar. 1987;111(3):265-9.

Ridker PM, Hennekens CH, Buring JE and Rifai N. C-reactive protein and other markers of inflammation in the prediction of cardiovascular disease in women. N Engl J Med. Mar. 23, 2000;342(12):836-43.

Ridker PM, Intrinsic fibrinolytic capacity and systemic inflammation: novel risk factors for arterial thrombotic disease. Haemostasis. 1997;27 Suppl 1:2-11.

Rodriguez-Lee M, Bondjers G and Camejo G, Fatty acid-induced atherogenic changes in extracellular matrix proteoglycans. Curr Opin Lipidol. Oct. 2007;18(5):546-53.

Rosen HN, Parker RA, Greenspan SL, Iloputaife ID, Bookman L, Chapin D, Perlmutter I, Kessel B, Qvist P, Rosenblatt M. Evaluation of ability of biochemical markers of bone turnover to predict a response to increased doses of HRT. Calcif Tissue Int 2004;74:415-423.

Rouis M. Matrix metalloproteinases: a potential therapeutic target in atherosclerosis. Curr Drug Targets.Cardiovasc Haematol Disord. 2005;5:541-48.

Rudel LL, Haines J, Sawyer JK, Shah R, Wilson MS, Carr TP. Hepatic origin of cholesteryl oleate in coronary artery atherosclerosis in African green monkeys. Enrichment by dietary monounsaturated fat. J Clin Invest 1997;100:74-83.

Salisbury BG and Wagner, W DJ Biol Chem. Aug. 10, 1981;256(15):8050-7,'Isolation and preliminary characterization of proteoglycans dissociatively extracted from huma aorta'.

Satta J, Juvonen T, Haukipuro K, Juvonen M, Kairaluoma MI. Increased turnover of collagen in abdominal aortic aneurysms, demonstrated by measuring the concentration of the aminoterminal propeptide of type III procollagen in peripheral and aortal blood samples. J Vasc.Surg. 1995;22:155-60.

Schaar JA, Mastik F, Regar E, den Uil CA, Gijsen FJ, Wentzel JJ et al. Current diagnostic modalities for vulnerable plaque detection. Curr Pharm Des. 2007;13:995-1001.

Schaller S, Henriksen K, Hoegh-Andersen P, Sondergaard BC, Sumer EU, Tanko LB, et al. In vitro, ex vivo, and in vivo methodological approaches for studying therapeutic targets of osteoporosis and degenerative joint diseases: how biomarkers can assist? Assay Drug Dev Technol Oct. 2005;3(5):553-580.

Schuppan D, Ruehl M, Somasundaram R, Hahn EG. Matrix as a modulator of hepatic fibrogenesis. Semin Liver Dis Aug. 2001;21(3):351-372.

Schwarze U, Atkinson M, Hoffman GG, Greenspan DS, Byers PH. Null alleles of the COL5A1 gene of type V collagen are a cause of the classical forms of Ehlers-Danlos syndrome (types I and II). Am J Hum Genet Jun. 2000;66(6):1757-1765.

Sebastiani G, Vario A, Guido M, Noventa F, Plebani M, Pistis R, Ferrari A, Alberti A. Stepwise combination algorithms of non-invasive markers to diagnose significant fibrosis in chronic hepatitis C. J Hepatol 2006;44:686-693.

Shekhonin BV, Domogatsky SP, Muzykantov VR, Idelson GL, Rukosuev VS. Distribution of type I, III, IV and V collagen in normal and atherosclerotic human arterial wall: immunomorphological characteristics. Coll.Relat Res 1985;5:355-68.

Shin, J., J. E. Edelberg, and M. K. Hong. "Vulnerable atherosclerotic plaque: clinical implications." Curr.Vasc.Pharmacol. 1.2 (2003): 183-204.

Siest G, Pillot T, Regis-Bailly A, Leininger-Muller B, Steinmetz J, Galteau MM and Visvikis S, Apolipoprotein E: an important gene and protein to follow in laboratory medicine. Clin Chem. Aug. 1995;41(8 Pt 1):1068-86.

Snyder N, Gajula L, Xiao SY, Grady J, Luxon B, Lau DT, Soloway R, Petersen J. APRI: an easy and validated predictor of hepatic fibrosis in chronic hepatitis C. J Clin Gastroenterol 2006;40:535-542.

Snyder N, Nguyen A, Gajula L, Soloway R, Xiao SY, Lau DT, Petersen J. The APRI may be enhanced by the use of the FIBROSpect II in the estimation of fibrosis in chronic hepatitis C. Clin Chim Acta 2007;381:119-123.

Stary HC. Composition and classification of human atherosclerotic lesions. Virchows Arch A.Pathol Anat.Histopathol. 1992;421:277-90.

Sundstrom J, Vasan RS. Circulating biomarkers of extracellular matrix remodeling and risk of atherosclerotic events. Curr Opin Lipidol. 2006;17:45-53.

Suzuki,K., Enghild,J.J., Morodomi,T., Salvesen,G., and Nagase,H. 1990. Mechanisms of activation of tissue procollagenase by matrix metalloproteinase 3 (stromelysin). Biochemistry 29:10261-10270.

Svensson L, Oldberg A, Heinegard D. Collagen binding proteins. Osteoarthritis and Cartilage 2001;9:S23-S28.

Symoens S, Renard M, Bonod-Bidaud C, Syx D, Vaganay E, Malfait F, et al. Identification of binding partners interacting with the alpha1-N-propeptide of type V collagen. Biochem J Dec. 22, 2010;433(2):371-381.

Talusan, P., et al. "Analysis of intimal proteoglycans in atherosclerosis-prone and atherosclerosis-resistant human arteries by mass spectrometry." Mol.Cell Proteomics. 4.9 (2005): 1350-57.

Tam LS, Gu J, Yu D. Pathogenesis of ankylosing spondylitis. Nat Rev Rheumatol Jul. 2010;6(7):399-405.

Terry JG, Howard G, Mercuri M, Bond MG and Crouse JR 3rd. Apolipoprotein E polymorphism is associated with segment-specific extracranial carotid artery intima-media thickening., Stroke. Oct. 1996;27(10):1755-9.

Tomasek JJ, Gabbiani G, Hinz B, Chaponnier C, Brown RA. Myofibroblasts and mechano-regulation of connective tissue remodelling. Nat Rev Mol Cell Biol 2002;3:349-363.

Toyama-Sorimachi N, Sorimachi H, Tobita Y, Kitamura F, Yagita H, Suzuki K, Miyasaka M. A novel ligand for CD44 is serglycin, a hematopoietic cell lineage-specific proteoglycan. Possible involvement in lymphoid cell adherence and activation. J Biol Chem 1995;270:7437-7444.

Tracy RP, Lemaitre RN, Psaty BM,Ives DG, Evans RW, Cushman M, Meilahn EN and Kuller LH, Relationship of C-reactive protein to risk of cardiovascular disease in the elderly. Results from the Cardiovascular Health Study and the Rural Health Promotion Project. Arterioscler Thromb Vasc Biol. Jun. 1997;17(6):1121-7.

Trang T, Petersen JR, Snyder N. Non-invasive markers of hepatic fibrosis in patients co-infected with HCV and HIV: comparison of the APRI and FIB-4 index. Clin Chim Acta 2008;397:51-54.

Trocme C, Leroy V, Sturm N, Hilleret MN, Bottari S, Morel F, Zarski JP. Longitudinal evaluation of a fibrosis index combining MMP-1 and PIIINP compared with MMP-9, TIMP-1 and hyaluronic acid in patients with chronic hepatitis C treated by interferon-alpha and ribavirin. J Viral Hepat 2006;13:643-651.

Tsochatzis E, Papatheodoridis GV, Hadziyannis E, Georgiou A, Kafiri G, Tiniakos DG, Manesis EK, Archimandritis AJ. Serum

(56) References Cited

OTHER PUBLICATIONS adipokine levels in chronic liver diseases: association of resistin levels with fibrosis severity. Scand J Gastroenterol 2008;43:1128-1136.

Turu MM, Krupinski J, Catena E, Rosell A, Montaner J, Rubio F et al. Intraplaque MMP-8 levels are increased in asymptomatic patients with carotid plaque progression on ultrasound. Atherosclerosis 2006;187:161-69.

Ulrich D, Noah EM, von HD, Pallua N. TIMP-1, MMP-2, MMP-9, and PIIINP as serum markers for skin fibrosis in patients following severe burn trauma. Plast Reconstr Surg 2003;111:1423-1431.

Vassiliadis E, Veidal SS, Simonsen H, Larsen DV, Vainer B, Chen X, et al. Immunological detection of the type V collagen propeptide fragment, PVCP-1230, in connective tissue remodeling associated with liver fibrosis. Biomarkers May 25, 2011.

Venugopal SK, Devaraj S, Yuhanna I, Shaul P and Jialal I. Demonstration that C-reactive protein decreases eNOS expression and bioactivity in human aortic endothelial cells., Circulation. Sep. 17, 2002;106(12):1439-41.

Wang TJ, Gona P, Larson MG, Tofler GH, Levy D, Newton-Cheh C et al. Multiple biomarkers for the prediction of first major cardiovascular events and death. N Engl J Med 2006;355:2631-39.

Wenstrup RJ, Florer JB, Brunskill EW, Bell SM, Chervoneva I, Birk DE. Type V collagen controls the initiation of collagen fibril assembly. J Biol Chem Dec. 17, 2004;279(51):53331-53337.

Wenstrup RJ, Florer JB, Willing MC, Giunta C, Steinmann B, Young F, et al. COL5A1 haploinsufficiency is a common molecular mechanism underlying the classical form of EDS. Am J Hum Genet Jun. 2000;66(6):1766-1776.

Whitelock, J. M. and R. V. Iozzo. "Heparan sulfate: a complex polymer charged with biological activity." Chem. Rev. 105.7 (2005): 2745-64.

Wight TN and Merrilees MJ, Proteoglycans in atherosclerosis and restenosis: key roles for versican. Circ Res. May 14, 2004;94(9):1158-67.

Wight TN, Versican: a versatile extracellular matrix proteoglycan in cell biology.Curr Opin Cell Biol. Oct. 2002;14(5):617-23.

Wight, T. N. "The extracellular matrix and atherosclerosis." Curr. Opin.Lipidol. 6.5 (1995): 326-34.

Wight, T. N., et al. "Vascular cell proteoglycans: evidence for metabolic modulation." Ciba Found.Symp. 124 (1986): 241-59.

Wilson PW, Schaefer EJ, Larson MG and Ordovas JM. Apolipoprotein E alleles and risk of coronary disease. A meta-analysis. Arterioscler Thromb Vasc Biol. Oct. 1996;16(10):1250-5.

Wong VS, Hughes V, Trull A, Wight DG, Petrik J, Alexander GJ. Serum hyaluronic acid is a useful marker of liver fibrosis in chronic hepatitis C virus infection. J Viral Hepat 1998;5:187-192.

World Health Organization. Reducing Risks, Promoting Healthy Life. Peducing Risks, Promoting Healthy Life, Geneva: WHO, 2002:1-230.

Wynn TA. Cellular and molecular mechanisms of fibrosis. J Pathol 2008;214:199-210.

Wynn TA. Common and unique mechanisms regulate fibrosis in various fibroproliferative diseases. J Clin Invest 2007;117:524-529.

Yamada H, Watanabe K, Shimonaka M, Yamaguchi Y. Molecular cloning of brevican, a novel brain proteoglycan of the aggrecan/versican family. J Biol Chem 1994;269:10119-10126.

Yamada Y, Izawa H, Ichihara S, Takatsu F, Ishihara H, Hirayama H et al. Prediction of the risk of myocardial infarction from polymorphisms in candidate genes. N Engl J Med 2002;347:1916-23.

Yang BL, Zhang Y, Cao L, Yang BB. Cell adhesion and proliferation mediated through the G1 domain of versican. J Cell Biochem 1999;72:210-220.

Yoneda M, Mawatari H, Fujita K, Iida H, Yonemitsu K, Kato S, Takahashi H, Kirikoshi H, Inamori M, Nozaki Y, Abe Y, Kubota K, Saito S, Iwasaki T, Terauchi Y, Togo S, Maeyama S, Nakajima A. High-sensitivity C-reactive protein is an independent clinical feature of nonalcoholic steatohepatitis (NASH) and also of the severity of fibrosis in NASH. J Gastroenterol 2007;42:573-582.

Zaman A, Rosen HR, Ingram K, Corless CL, Oh E, Smith K. Assessment of FIBROSpect II to detect hepatic fibrosis in chronic hepatitis C patients. Am J Med 2007;120:280-14.

Zhen EY, Brittain IJ, Laska DA, Mitchell PG, Sumer EU, Karsdal MA, et al. Characterization of metalloprotease cleavage products of human articular cartilage. Arthritis Rheum Aug. 2008;58(8):2420-2431.

Zheng M, Cai WM, Weng HL, Liu RH. ROC curves in evaluation of serum fibrosis indices for hepatic fibrosis. World J Gastroenterol 2002;8:1073-1076.

Zwaka TP, Hombach V and Torzewski J. C-reactive protein-mediated low density lipoprotein uptake by macrophages: implications for atherosclerosis., Circulation. Mar. 6, 2001;103(9):1194-7.

Banks RE, et al., The acute phase protein response in patients receiving subcutaneous UL-6; Clin Exp Immunol 1995; 102:217-223.

Ying S-C et al: "Localization of sequence-determined neoepitopes and neutrophil digestion fragments of C-reactive protein utilizing monoclonal antibodies and synthetic peptides" Molecular Immunology, Pergamon, GB, vol. 29, No. 5, May 1, 1992, pp. 677-687.

Bisoendial et al: "C-reative protein and atherogenesis: From fatty streak to clinical event", Atherosclerosis, Elsevier Ireland Ltd, IE, vol. 195, No. 2, Jul. 21, 2007, pp. e10-e18.

Molloy K J et al: "Unstable carotid plaques exhibit raised matrix metalloproteinase-8 activity" Circulation, vol. 110, No. 3, Jul. 20, 2004, pp. 337-343.

Satta et al: "Incerased turnover of collagen in abdominal aortic aneurysms, demonstrated by measuring the concentration of the aminoterminal propeptide of type III procollagen in peripheral and aortal blood samples" Journal of Vascular Surgery, C.V. Mosby Co., St. Louis, MO, US, vol. 22, No. 2, 1995, pp. 155-160.

Zannad F et al: "Limitationo f excessive extracellular matrix turnover my contribute to survival benefit of spironolactone therapy in patients with congestive heart failure: insights from the rtandomized aldactone evaluation study (RALES). Rales Investigators." Circulation Nov. 28, 2000, vol. 102, No. 22, Nov. 28, 2000, pp. 2700-2706.

Lin Y H et al: "The relation of amino-terminal propeptide of type III procollagen and severity of coronary artery disease in patients without myocardial infarction or hibernation" Clinical Biochemistry, Elsevier Inc, US, CA, vol. 39, No. 9, Sep. 1, 2006, pp. 861-866.

Shinohara, Tadashi et al., "Soluble Elastin Fragmens in Serum are Elevated in Acute Aortic Dissection", Arterioscler Thromb Vasc. Biol., Oct. 2003, pp. 1839-1844.

Zimmerli, Lukas U. et al., "Urinary Proteomic Biomarkers in Coronary Artery Disease", Molecular & Cellular Proteomics 7.2, Oct. 18, 2007, pp. 290-298.

* cited by examiner

PATHOLOGY BIOMARKER ASSAY

CROSS REFERENCE TO RELATED APPLICATIONS

This application is a continuation-in-part of U.S. application Ser. No. 12/749,652, filed on Mar. 30, 2010, which is a continuation-in-part of PCT/EP2008/064946 filed on Nov. 4, 2008, which claims Convention priority from GB0721713.6 filed in the United Kingdom on Nov. 5, 2007, GB0722748.1 filed in the United Kingdom on Nov. 20, 2007 and GB0802814.4 filed in the United Kingdom on Feb. 15, 2008, and also claims the benefit under 35 U.S.C. §1.119(e) of U.S. Provisional application No. 61/211,467 filed on Mar. 30, 2009 and U.S. Provisional application No. 61/289,081 filed on Dec. 22, 2009. The entire contents of each of the aforementioned patent applications are incorporated herein by this references.

The present invention relates to assays for biomarkers useful in the diagnosis of various diseases including fibrosis diseases and prognosis of its development, including biomarkers indicative of the risk of developing disease, e.g. the risk of developing a fibrosis after a chronic injury. Biomarkers for inflammatory diseases such as ankylosing spondylitis are also described as are biomarkers for cardiovascular diseases (CVD).

In particular, according to the present invention, biomarkers relating to degradation fragments of Collagen type I, III, IV, V, and VI, elastin, C-reactive protein, ApoE, lumican, LAMC1, LAMB1, LAMA5 and proteoglycans including Biglycan, Decorin, Versican, and Perlecan are found to be useful.

Fibrotic diseases (including those listed in Table 1) are a leading cause of morbidity and mortality, e.g. cirrhosis with 800,000 death per year worldwide[1].

TABLE 1

Different fibrotic diseases[2]

| Tissue | Examples of Causes |
|---|---|
| Liver | Viral hepatitis |
|  | Schistosomiasis |
|  | Steatohepatitis (Alcoholic or non-alcoholic) |
| Lung | Idiopathic pulmonary fibrosis (IPF) |
|  | Systemic sclerosis (Scleroderma) |
| Kidney | Nephrogenic systemic fibrosis (NSF) |
|  | Diabetes |
|  | Untreated hypertension |
| Heart | Heart attack |
|  | Hypertension |
|  | Atherosclerosis |
|  | Restenosis |
| Eye | Macular degeneration, retinal and vitreal retinopathy |
| Skin | Systemic sclerosis and scleroderma, keloids, hypertrophic scars, burns, genetic factors NFS |
| Pancreas | Autoimmune/hereditary causes |
| Intestine | Crohn's disease/inflammatory bowel disease |
| Brain | Alzheimer's disease, AIDS |
| Bone marrow | Cancer, ageing |
| Multi-organ fibrosis | Surgical complications, chemotherapeutic drug-induced fibrosis, radiation-induced fibrosis, mechanical injuries |

A 'fibrotic disease' is any disease giving rise to fibrosis, whether as a main or a secondary symptom.

Fibrosis is the end result of chronic inflammatory reactions induced by a variety of stimuli including persistent infections, autoimmune reactions, allergic responses, chemical insults, radiation, and tissue injury. Fibrosis is characterized by the accumulation and reorganization of the extracellular matrix (ECM). Despite having obvious etiological and clinical distinctions, most chronic fibrotic disorders have in common a persistent irritant that sustains the production of growth factors, proteolytic enzymes, angiogenic factors, and fibrogenic cytokines, which together stimulate the deposition of connective tissue elements, especially collagens and proteoglycans, which progressively remodel and destroy normal tissue architecture[3,4]. Despite its enormous impact on human health, there are currently no approved treatments that directly target the mechanisms of fibrosis[5].

The key cellular mediator of fibrosis is the myofibroblast, which when activated serves as the primary collagen-producing cell.

Inflammatory Conditions

Ankylosing Spondylitis (AS) is a form of chronic inflammation of the spine and the sacroiliac joints. Over time, chronic inflammation of the spine can lead to a complete cementation of the vertebrae (110), a process with a molecular pathology that still remains to be investigated and fully understood. AS is also a systemic disease, affecting other tissues throughout the body including inflammation in or injury to other joints, as well as to organs, such as eyes, heart, lungs, and kidneys (111). The inflammation related processes in AS, involving multiple tissues seems to involve molecular processes including increased MMP activity and collagen deposition, seen in most types of connective tissue turnover.

Extracellular matrix (ECM) remodeling is a key process of tissue homeostasis (112, 113). Specific proteolytic activities are a prerequisite for a range of cellular functions and interactions within the ECM (114). These specific activities are precisely coordinated under normal physiological situations, with a specified sequence of events resulting in controlled tissue turnover. In pathological situations, with special emphasis on connective tissue diseases, the normal repair-response relationship is disturbed (115), leading to excessive remodeling and tissue turnover. The consequence of this ECM remodeling is the release of a range of degradation products of proteins, neoepitopes, generated by the proteases expressed locally in the pathologically affected area. These protein degradation fragments may serve as molecular biomarker targets, as they are more specific for the tissue of origin compared to their intact origins (116).

Endopeptidases, such as matrix metalloproteinases (MMPs), play a major role in the degradation of ECM proteins as collagens and proteoglycans (117, 118). In particular, in connective tissue diseases such as fibrosis, MMP-2 and -9 have been shown to be highly up-regulated (119-121). Recently, neoepitope-based biochemical markers found in urine and serum have received increased attention for their diagnostic and prognostic potential (116). In particular for slow progressing diseases, such as osteoporosis and osteoarthritis, bone resorption and cartilage degradation markers, based on type I and II collagen degradation products respectively, have been studied extensively (122).

Extracellular Matrix (ECM)

Fibrogenesis is a dynamic process involving complex cellular and molecular mechanisms that usually originates from tissue injury[6]. Fibrogenesis is the result of an imbalance in normal ECM regulation that alters the concentration of macromolecules leading to increased tissue size and density, with progressively impaired function. These macromolecules are mainly fibrous proteins with structural and adhesive functions, such as collagens and proteoglycans.

Collagen

Collagens are widely distributed in the human body, i.e. ~30% of the protein mass in the human body is composed of collagens. Collagens are responsible for the structural integrity of the ECM of most connective tissues. The ECM content results from a fine balance between synthesis and degradation tightly controlled through regulation of gene expression and protein secretion, but also through endogenous protease inhibition and protein degradation by metalloproteinases and cysteine proteases[7-9]. Table 2 lists the major collagen types with their major tissue distribution.

TABLE 2

Major collagen types and their tissue distribution.

| Collagen type | Tissue distribution |
|---|---|
| I | Most connective tissues |
| II | Cartilage, vitreous humor |
| III | Extensible connective tissues, e.g. liver, skin, lung, vascular system |
| IV | Basement membranes |
| V | Tissues containing collagen I |
| VI | Most connective tissues |
| VII | Skin, bladder, oral mucosa, umbilical cord, amnion |
| VIII | Many tissues, especially endothelium |
| XIII | Endothelial cells, skin, eye, heart, skeletal muscle |
| XIV | Vessel, bone, skin, cartilage, eye, nerve, tendon, uterus |
| XXI | Vessel, heart, stomach, kidney, skeletal muscle, placenta |

Type I collagen is the most abundant collagen and is found in most connective tissues. It is especially important for the structure of bone and skin where the major collagenous components are type I and III collagens[10].

Collagen type I and III are the major components of liver and lung in a 1:1 ratio in healthy tissue. In addition, collagen type IV and VI are found in the basement membranes in most tissues. The most common localization of type V collagen is within the characteristic collagen fibrils, in association with the collagen type I and III[10].

Some collagens have a restricted tissue distribution: for example, type II, which is found almost exclusively in cartilage[11].

During fibrogenesis the net amount of collagens increases[12-4]. Table 3 shows by way of example the collagen increase during liver fibrosis.

TABLE 3

Changes of the composition of collagen from normal to cirrhotic human liver[15].

| Collagen type | Chains | Collagen normal liver (mg/g) | Collagen cirrhotic liver (mg/g) | Times increased | Distribution normal liver (%) | Distribution cirrhotic liver (%) |
|---|---|---|---|---|---|---|
| I | $\alpha_1$ (I) | | 16 | 8 | 37 | 42 |
| | $\alpha_2$ (I) | 2 | | | | |
| III | $\alpha_1$ (III) | 2 | 8 | 4 | 37 | 21 |
| IV | $\alpha_1$ (IV) | 0.5 | 7 | 14 | 9 | 18 |
| | $\alpha_2$ (IV) | | | | | |
| V | $\alpha_1$ (V) | 0.9 | 7 | 8 | 17 | 18 |
| | $\alpha_2$ (V) | | | | | |
| | $\alpha_3$ (V) | | | | | |
| VI | $\alpha_1$ (VI) | 0.01 | 0.1 | 10 | 0.2 | 0.3 |
| | $\alpha_2$ (VI) | | | | | |

Type V collagen has been documented to be critically important for the formation of collagen fibrils (123), exemplified by an almost virtual lack of collagen fibril formation in the col5a1−/− mice. In alignment, the heterozygous mice, was associated with a 50% reduction in fibril number and dermal collagen content. This indicates a central role for type V collagen in the life dependent regulation of fibrillogenesis, suggesting this collagen type to be of pivotal interest in many connective diseases. However, there is still a conceptual lack of understanding of the role of type V collagen turnover in connective diseases that may in part may be due to the technical inabilities for investigation of collagen type V degradation and turnover. Interesting, very recently a limited diverse set of proteins were found to bind type V collagen, beginning to elucidate the molecular function of this molecule in more details, of which MMP-2 was one of them (124). In addition to the molecular characterization, more evidence is emerging that type V collagen directly affects different cellular phenotypes by inducing dynamic motility and other cellular activities, suggesting that this proteins may be more than a passive component of the ECM (125, 126). In direct support of this, we recently described a very strong correlation to liver fibrosis with the formation of type V collagen in two separate animal models of liver fibrosis (127), suggesting a central role of type V collagen formation in excessive tissue turnover.

Type V collagen is a fibril-forming collagen, together with type I, II, III and XI (11), and is formed as heterotrimers of three different α-chains (α1, α2, α3). It typically forms heterofibrils with type I and III collagens and contributes to the organic bone matrix, corneal stroma and the interstitial matrix of muscles, liver, lungs and placenta (128). Type V collagen mutation results in a range of connective tissue diseases, of which the Ehlers-Danlos syndrome (EDS) the best described. EDS is a heterogeneous group of heritable disorders characterized by joint hypermobility, skin changes (e.g. hyperextensibility, thinness and fragility). The disease can be divided into different subtypes, EDS1 & II. EDS types I and II are characterized by atrophic scars, skin hyper extensibility and joint laxity. It is evident that both subtypes result from mutations in the COL5A1 and COL5A2 genes that encode two of the polypeptide chains of type V collagen (129-131). This highlights the importance of type V collagen in connective tissues diseases.

Elastin

Elastin is a protein present in many connective tissues, primarily those that are elastic. It has a very high content of the amino acids glycine, valine, alanine, and proline, and has a molecular weight of 64 to 66 kDa. It is organised in an irregular or random coil conformation made up of 830 amino acids. Elastin is made by linking many soluble tropoelastin protein molecules, in a reaction catalyzed by lysyl oxidase, to make a massive insoluble, durable cross-linked array.

Elastin serves an important function in arteries as a medium for pressure wave propagation to help blood flow and is particularly abundant in large elastic blood vessels such as the aorta. Elastin is also very important in the lungs, elastic ligaments and the skin.

Despite much efforts devoted to the understanding of elastin synthesis and turnover, neo-epitopes originating from the proteolytic cleavage of this matrix molecules have until now not been associated with disease development in fibrosis.

Vimentin

Vimentin is a member of the intermediate filament family of proteins. Intermediate filaments are an important structural feature of eukaryotic cells. They, along with microtubules and actin microfilaments, make up the cytoskeleton. Although most intermediate filaments are stable structures, in fibroblasts, vimentin exists as a dynamic structure. This filament is used as a marker for mesodermally derived tissues, and as such has been used used as an immunohistochemical marker for sarcomas.

Hertig and coworkers (Hertig et al., J Am Soc Nephrol. 2008 August; 19(8):1584-91) investigated if epithelial-to-mesenchymal transition in renal tubular epithelial cells of subjects with chronic allograft nephropathy could predict the progression of fibrosis in the allograft and measured vimentin expression in 83 biopsies from these. They did find an association between elevated vimentin expression and the intestinal fibrosis score at 1 year after surgery.

In another study of hepatic fibrosis, Meriden and colleagues (Meriden et al., Clin Gastro & Hepatol 2010; 8:289-296) found a significant association between vimentin expression (in biopsies obtained at F0 stage) and fibrosis progression, with elevated levels predicting rapid progression of the hepatic fibrosis.

Accordingly, we wanted to investigate if circulating fragments of vimentin could serve as sensitive and specific biomarkers of fibrosis.

Proteoglycans

Proteoglycans are a diverse group of macromolecules, which covalently link a variable number of glycosaminoglycan (GAG) side chains to a core protein[16]. These GAGs are polymers of disaccharide repeats (e.g. N-acetyl glucosamine or N-acetyl galactosamine), which are acidic (negatively charged) due to hydroxyl, carboxylated and sulfated side groups on the disaccharide units. This makes them highly hydrophilic, thus aiding the diffusion of water and positive ions (e.g. sodium from extracellular fluids)[17]. Furthermore, GAGS have the ability to form non-covalent links with for example hyaluronic acid chains to form even larger molecular complexes[16]. Table 4 lists the most studied proteoglycans associated with connective tissue.

TABLE 4

Proteoglycans of the extracellular matrix of connective tissue

| Group | Proteoglycans | Origin | Function |
|---|---|---|---|
| Large extracellular proteoglycans (aggregating and hyaluronan-binding) | Aggrecan [18] | Articular cartilage chondrocytes, intervertebral disc, nasal cartilage | Extracellular matrix stability (hyaluronan binding) |
| | Versican [19, 20] | Connective tissue: fibroblast, keratinocytes, smooth muscle cells, mesangial cells | Cell-cell and cell-matrix interactions Binding of sugars in Ca-dependent manner |
| | Neurocan [21] | Nervous tissue | Binds to neural cell adhesion molecules |
| | Brevican [22] | Nervous tissue | Extracellular matrix stability |
| Small Leucine-rich proteoglycans (collagen-binding) | Decorin [23] | Connective tissue, cartilage, bone | Binds to and connect collagen molecules (matrix stabilization and thickness) Organogenesis Binding of TGFβ |
| | Biglycans [24] | Capillary endothelium, skin (keratinocytes), epithelium of kidney | Cell differentiation Binds and connect collagen fibrils |
| | Fibromodulin [17] | Connective tissue, bone, cartilage | Regulate orientation of collagen fibers |
| | Lumican [23] | Cornea, muscle, cartilage, kidney, lung, intestine | Controls spacing and thickness of collagen fibers |
| Cell-associated proteoglycans | Serglycins [25] | Widely distributed to endothelium - intercellular compartments | Hemopoietic cell differentiation Adhesion and activation of lymphoid cells |
| | Syndecans [26] | Widely distributed - often cell membrane bound | Binds collagens, fibronectin, thrombospondin, tenascin and bFGF |
| | Betaglycan [27] | Widely distributed | TGFβ receptor and signaling Possible reservoir of TGFβ |
| Basement membrane proteoglycans | Perlecan [28] | All basement membranes | Selective barrier for macromolecules Cell-adhesion |

C-Reactive Protein

C-reactive protein (CRP) is an acute phase serum protein produced by the liver in response to different clinical conditions such as, inflammation, infection, or trauma[29]. The production of CRP is induced by cytokines such as IL-6, released from the affected or damaged tissues. The physiological role of CRP is yet unknown and discussions on its pro- or anti-inflammatory actions are ongoing.

Apolipoprotein E

Apolipoprotein E (APOE) is a class of apolipoprotein found in the chylomicron (large lipoprotein particles) and intermediate-density lipoprotein particles that binds to specific receptors on liver cells and peripheral cells. It is essential for the normal catabolism of triglyceride-rich lipoprotein constituents. APOE is 299 amino acids long and transports lipoproteins, fat-soluble vitamins, and cholesterol into the lymph system and then into the blood. It is synthesized principally in the liver, but has also been found in other tissues such as the brain, kidneys, and spleen. APOE is essential for the normal catabolism of triglyceride-rich lipoprotein constituents. APOE was initially recognized for its importance in lipoprotein metabolism and cardiovascular disease.

Elastin

Elastin is the extracellular matrix molecule responsible for resilience of tissues and was first thought to be restricted to that role. It is now established that elastin degradation may lead to the production of bioactive peptides influencing cell chemotaxis, cell proliferation, and proteases synthesis in a broad panel of normal and tumor cells.

LAMC1, LAMA2, LAMB1, and LAMA5

Laminins, a family of extracellular matrix glycoproteins, are the major noncollagenous constituent of basement membranes. They have been implicated in a wide variety of biological processes including cell adhesion, differentiation, migration, signaling, neurite outgrowth and metastasis. Laminins are composed of 3 non-identical chains: laminin alpha, beta and gamma (formerly A, B1, and B2, respectively) and they form a cruciform structure consisting of 3 short arms, each formed by a different chain, and a long arm composed of all 3 chains. Each laminin chain is a multidomain protein encoded by a distinct gene. Several isoforms of each chain have been described. Different alpha, beta and gamma chain isomers combine to give rise to different heterotrimeric laminin isoforms which are designated by Arabic numerals in the order of their discovery. The biological functions of the different chains and trimer molecules are largely unknown, but some of the chains have been shown to differ with respect to their tissue distribution, presumably reflecting diverse functions in vivo.

LAMC1 (formerly LAMB2) is the laminin subunit gamma-1.
LAMA2 is the laminin subunit alpha-2
LAMB1 is the laminin subunit beta-1
LAMA5 is the laminin subunit alpha-5

Proteases

The imbalance between synthesis and degradation of ECM during fibrogenesis, results from conversion of the low-density subendothelial matrix into matrix rich in interstitial collagens. The increase in collagen and proteoglycans may be due to one or both of (1) a decrease in protein production and (2) impaired protein degradation, and hence less matrix degradation. The decreased protein degradation has recently received increased attention. In the regulation of this process matrix metalloproteinases (MMPs) and their tissue inhibitors (TIMPs) play important roles, as well as other proteases and their inhibitors, such as cystein proteases and the cystatins.

MMPs

MMPs are a large group of endopeptidases, capable of degrading most if not all components of the ECM. Presently, more than 25 MMPs have been found. MMPs are characterized by an active site containing a metal atom, typically zinc, and are secreted as zymogens. Different MMPs are expressed in different tissues. In Table 5 MMPs in the liver are shown.

TABLE 5

MMPs in the liver[30-32]

| Family | Protease | Source | Substrate |
| --- | --- | --- | --- |
| Collagenases | MMP-1 | HSC | I, II, III, VII, VIII, X, gelatin |
| | MMP-8 | Neutrophil | I, II, III, V, VII, X, gelatin |
| | MMP-13 | HSC, MFB, KC | I, II, III, VII, X, gelatin |
| Stromelysins | MMP-3 | HSC | III, IV, V, IX, X, XI, gelatin, laminin, fibronectin, proteoglycans, glycoproteins, elastin, pro-MMP-1/13 |
| | MMP-10 | HSC | III, IV, V, gelatin, elastin, aggrecan |
| | MMP-11 | HC | PAI-1, week activity against matrix proteins |
| Gelatinases | MMP-2 | HSC, MBF | I, II, III, IV, V, VII, X, XI, gelagin, elastin, laminin |
| | MMP-9 | KC, HSC, HC | I, II, III, IV, V, VII, X, XI, gelagin, elastin, laminin |
| | MMP-7 | HSC | Entactin, gelatin, elastin, fibronectin, vitronectin, laminin, fibrinogen |
| Metalloelastase | MMP-12 | Macrophages | Elastin, gelatins, IV, laminin, fibronectin, entactin, vitronectin, proteoglycan, myelin basic protein, α1-antitripsin |
| MT-MMPs | MMP-14 | HSC, MFB, KC | I, II, III, gelatin, fibronectin, vitronectin, laminin, fibrinogen, pro-MMP-2, pro-MMP-13 |
| | MMP-15 | HC, BDEC | Pro-MMP-2, fibronectin, tenascin, laminin, aggrecan, perlecan |

TIMPs block MMPs' proteolytic activity by binding in a substrate- and tissue-specific manner to MMP and membrane-type 1 metalloproteinase in a trimolecular complex (Table 6). During fibrosis TIMP levels increase dramatically, and MMP levels increase modestly or remain relatively static (except MMP-2) which in all gives a decrease in degradation of collagens.

TABLE 6

TIMPs in the liver[31]

| Name | Sources | Metalloproteinase inhibited |
| --- | --- | --- |
| TIMP-1 | HSC, MFB, KC, HC | Pro-MMP-9, MMP-1, MMP-2, MMP-3, MMP-13 |
| TIMP-2 | KC, HSC | MT-MMP-1, MT-MMP-2, proMMP-2, MMP-3, MMP-13, MMP-7 |
| TIMP-3 | HC | MT-MMP-1, MT-MMP-2, TACE, MMP-13 |

Fibroblast Activation Protein

Fibroblast Activation Protein alpha subunit (FAPa or FAP, alpha) is an integral membrane gelatinase belonging to the serine protease family. FAPa is the alpha subunit and DPP4 (CD26) the beta subunit of a heterodimeric membrane-bound proteinase complex also known as 170 kDa Melanoma Membrane Gelatinase, Integral Membrane Serine Proteinase and Seprase. Some cells make only FAPa homodimers, some only DPP4 homodimers. The monomer is inactive. FAP, alpha is selectively expressed in reactive stromal fibroblasts of epithelial cancers, granulation tissue of healing wounds, and malignant cells of bone and soft tissue sarcomas[33]. This protein is thought to be involved in the control of fibroblast growth or epithelial-mesenchymal interactions during development, tissue repair, and epithelial carcinogenesis. It has been shown that expression of FAP increase with the stage of fibrosis[35].

ADAMTS

ADAMTS (A Disintegrin And Metalloproteinase with Thrombospondin Motifs) is a family of peptidases, and until now 19 members of this family have been identified in humans. Known functions of the ADAMTS proteases include processing of procollagens and von Willebrand factor as well as cleavage of aggrecan, versican, brevican and neurocan. They have been demonstrated to have important roles in connective tissue organization, coagulation, inflammation, arthritis, angiogenesis and cell migration.

Cathepsins

There are approximately a dozen members of the cathepsins family of proteases, which are distinguished by their structure, catalytic mechanism, and which proteins they cleave. Most of the members become activated at the low pH found in lysosomes. Thus, the activity of this family lies almost entirely within those organelles (although there are many exceptions). Such as cathepsin K which (among other activities) works extracellularly after secretion by osteoclasts in bone resorption.

Cathepsin K (CAT K) and Cathepsin S (CAT S) are both cysteine proteases.

Fibrosis Biomarkers

A number of biochemical markers have been suggested for fibrotic diseases, although not specific product of the disease. In Table 7 is an example of biochemical markers of liver fibrosis used in clinical trial. In addition there are a lot of examples of biomarkers of other fibrotic diseases[12, 36-42].

Table 7 summarizes some of the known markers of liver fibrosis.

| Biomarker | Parameters | Chronic liver disease | Reference |
|---|---|---|---|
| One parameter | | | |
| CRP | | NASH | 43 |
| Hyaluronan | | HCV | 44-47 |
| IGF-I | | HCV | 48 |
| Leptin | | HCV | 49 |
| PIIIP | | HCV | 50 |
| Several parameters | | | |
| MP3 | PIIINP, MMP1 | HCV | 51, 52 |
| Zheng et al index | HA, PIIICP, PIIINP, Laminin, C-IV | Chronic hepatitis | 53 |
| Lebensztjen et al index | Laminin-2, C-IV, MMP2, MMP9-TIMP1 index | HBV | 54 |
| | Tenascin, hyaluronana, Colalegn VI, TIMP-1 | HBV | 55 |
| Tsochatzis et al index | Leptin, adiponectin, resistin | HCV, HBC, NASH | 56 |
| Patel et al index | Hyaluronan, TIMP-1, $\alpha_2$-macroglobulin | HCV | 57 |
| | TIMP-1, tenascin, collagen IV, PIIINP, MMP2, laminin, Hyaluronan | NASH | 58 |
| Forns-index (76, 77) | Age, platelet count, γGT, cholesterol | HCV HIV/HCV | 51, 59-62 |
| FibroTest (76, 78) | Haptoglobin, $\alpha_2$-macroglobulin, apolipoprotein A1, γGT, bilirubin | HCV HIV/HCV NAFLD NAFLD in diabetes patients | 45, 51, 60, 61, 63-75 |
| Actitest | FibroTest + ALT | HCV | 65, 76-78 |
| APRI (Wai-index) | AST, platelet count | HIV/HCV HCV NAFLD | 45, 51, 60, 61, 64, 66, 79-87 |
| Hepascore | Bilirubin, γGT, hyaluronan, $\alpha_2$-macroglobulin, age, gender | HCV HIV/HCV | 51, 61, 64, 66, 88 |
| FIB-4 | Platelet count, AST, ALT, age | HIV/HCV | 61, 83 |
| SHASTA | Hyaluronan, albumin, AST | HIV/HCV | 61 |
| Fibroindex | FORN + APRI | HCV | 89 |
| Fibrometer test | Platelet count, prothrombin index, AST, $\alpha_2$-macroglobulin, hyaluronan, urea, age | HIV/HCV HCV NAFLD | 51, 61, 64, 66, 81 |

-continued

| Biomarker | Parameters | Chronic liver disease | Reference |
|---|---|---|---|
| NFSA | Age, hyperglycaemia, body mass index, platelets, albumin, AST/ALT | NAFLD | 81 |
| Ultrasound + APRI | | HCV | 82 |
| Metwally et al index | Platelet count, albumin, AST, history of blood transfusion, HBV core antibody | HCV | 90 |
| Mohamadnejad et al index | Age, HBV DNA levels, alkaline phosphatase, albumin, platelet counts, AST | HCV | 91 |
| FibroSpect II | Hyaluronan, TIMP-1, $\alpha_2$-macroglobulin | HCV | 85, 92, 93 |
| Stepwise combination algorithms | Combination of APRI and Fibrotest | HCV | 94 |
| Imbert-Bismut index | $\alpha_2$ macroglobulin, AST, ALT $\gamma$GT, total bilirubin, albumin, $\alpha_1$ globulin, $\alpha_2$ globulin, $\beta$ globulin, $\gamma$ globulin, apolipoprotein $A_1$ | HCV | 95 |
| Nunes et al | Age, Platelets, INR, CD4, AST/ALT, Hyaluronan, YKL-40, PIIINP | HCV/HIV HCV | 96 |
| Fibroscan+++ | Fibroscan, Fibrotest, APRI, | HCV | 97 |

U.S. Pat. No. 5,387,504 describes the neo-epitope VDIPEN released by the action of stromelysin at the aggrecan site $N_{341}$-$F_{342}$ and an RIA assay employing a monoclonal antibody specific for this neo-epitope. More generally the use of monospecific antibodies specific for fragments of aggrecan, generated by specific stromelysin cleavage are described. Elevations of stromelysin occur in osteoarthritis, rheumatoid arthritis, atherosclerotic lesions, gout, inflammatory bowel disease (IBD), idiopathic pulmonary fibrosis (IPF), certain cancers, joint injuries, and numerous inflammatory diseases. Stromelysin is reported to be elevated in idiopathic pulmonary fibrosis, and it is alleged that the assay can be conducted on blood or other biological fluids to detect stromelysin cleavage products of aggrecan and that quantitation of such fragments can be used diagnostically in respect of IPF as well as other conditions. However, no evidence for this is provided and there have to our knowledge been no subsequent publications validating this prediction. Such RIA assays have been commercially available for many years and no reports of their successful use in diagnosing or monitoring any fibrotic disease have appeared.

U.S. Pat. No. 7,225,080 discloses a method for diagnosis of an inflammatory, a fibrotic or a cancerous disease in a patient by measuring the values of at least four biochemical markers selected from the group consisting of $\alpha_2$-macroglobulin, AST (aspartate aminotransferase), ALT (alanine aminotransferase), GGT (gammaglutamyl transpeptidase), $\gamma$-globulin, total bilirubin, albumin, $\alpha_1$-globulin, $\alpha_2$-globulin, haptoglobin, $\beta$-globulin, apoA1, IL-10, TGF-$\beta$1, apoA2, and apoB in the serum or plasma of said patient, and subsequently combining said values in order to determine the presence of liver fibrosis and/or liver necroinflammatory lesions in said patient. The patent does not teach the quantitative measurement of peptide fragment carrying neo-epitopes generated during fibrotic disease.

U.S. Pat. No. 6,060,255 describes a method for diagnosing the degree of liver fibrosis, comprising the steps of measuring the concentration of type IV collagen high molecular weight form in a sample using an antibody that specifically binds to type IV collagen, and relating the measurement to the degree of liver fibrosis. Again, no use is made of neo-epitopes produced by proteolytic enzymes acting in the body. The sample is actually digested with pepsin, which may obscure the natural pattern of collagen cleavage in the sample.

U.S. Pat. No. 4,628,027 (Gay) discloses the production of antibodies specific for connective tissue proteins and, more particularly, the production of monoclonal antibodies by fused cell hybrids against human collagens and enzymes involved in collagen degradation. The use of monoclonal antibodies against connective tissue proteins to establish the collagen profile of histological, cytological and biological fluid samples is described. However, the patent does not describe the measurement of connective tissue proteins based on the binding of antibodies to neo-epitopes on said connective tissue proteins.

Guañabens N et al, J Bone Miner Res, 1998[98] evaluated the bone turnover markers N-telopeptide of type I collagen (NTX), C-telopeptide of type I collagen (CTX) and N-terminal pro-peptide of collagen type I (PINP) in patients with primary biliary cirrhosis, a disease with increased hepatic fibrosis. The level of NTX, CTX and PINP were elevated in patients compared to controls and correlated with the histological stage of the disease. The antibodies employed in the NTX were raised against a cathepsin K cleaved site in the N-terminal of collagen type I and are dependent on the neoepitope YDGKGVG↓ SEQ ID NO 302. The antibodies employed in the CTX were raised against a cathepsin K cleaved site in the C-terminal of collagen type I and are dependent on the neoepitope EKAHDGGR↓ SEQ ID NO 303. These markers are located in telopeptides of collagen type I and not in the internal part (the triple helical part) of collagen type I. The monoclonal antibodies employed for the PINP assay were raised against an internal epitope in the PINP sequence which is not a neo-epitope.

Møller S et al, Gut., 1999[99] demonstrated that the C-terminal cross linked telopeptide of type I collagen (ICTP) was elevated in alcoholic cirrhosis patients compared to controls. The study described showed that a biochemical marker can reflect hepatic fibrosis. The ICTP polyclonal antibody has been raised against trypsin and collagenase cleaved collagen type I. However, the antibodies are not binding to a neo-epitope.

Rosen H N et al, Calcif Tissue Int, 2004[100] assessed the bone turnover markers N-telopeptide of type I collagen (NTX) and C-telopeptide of type I collagen (CTX) in women receiving hormone replacement treatment (HRT). In the study it was observed that the bone turnover markers decreased with treatment. The antibodies employed in the NTX were raised against a cathepsin K cleaved site in the N-terminal of collagen type I and are dependent on the neoepitope YDGKGVG↓ SEQ ID NO 302. The antibodies employed in the CTX were raised against a cathepsin K cleaved site in the C-terminal of collagen type I and are dependent on the neoepitope EKAHDGGR↓ SEQ ID NO 303. In contrast to the present invention, these antibodies were used for evaluation of bone metabolism and not fibrosis.

Lein M et al, Eur Urol, 2007[101] evaluated the use of the neo-epitope specific bone turnover markers N-telopeptide of type I collagen (NTX) and C-telopeptide of type I collagen (CTX) in prostate cancer patients receiving zoledronic acid. In the study it was observed that the bone turnover markers decreased with treatment. The antibodies employed in the NTX were raised against a cathepsin K cleaved site in the N-terminal of collagen type I and are dependent on the neoepitope YDGKGVG↓ SEQ ID NO 302. The antibodies employed in the CTX were raised against a cathepsin K cleaved site in the C-terminal of collagen type I and are dependent on the neoepitope EKAHDGGR↓ SEQ ID NO 303. In contrast to the present invention, these antibodies were used for evaluation of the bone metabolism during invasion of bone metastases and not fibrosis.

PIIINP has been used in a number of studies to assess the severity of fibrotic disease[102] in patients with skin fibrosis following severe burn trauma[103], for disease progression in noncirrhotic primary biliary cirrhosis[104] in primary biliary cirrhosis and chronic viral hepatitis C[105].

PIIINP and ICTP were measured in patients with fibrosis of the myocardium[106].

Many reports combine a set of biochemical markers to improve the predictive value of the biochemical index. Eleven different serum markers were measured in 205 patients with fibrotic staging from F0 to F4, and the most informative markers were alpha2 macroglobulin, alpha2 globulin (or haptoglobin), gamma globulin, apolipoprotein A1, gamma glutamyltranspeptidase, and total bilirubin[107]. An index of these markers had a negative predictive value (100% certainty of absence of F2, F3, or F4) was obtained for scores ranging from zero to 0.10 (12% [41] of all patients), and high positive predictive value (>90% certainty of presence of F2, F3, or F4) for scores ranging from 0.60 to 1.00 (34% [115] of all patients).

WO2010/115749 discloses numerous neoepitopes of some of the proteins described above as fibrosis biomarkers and WO2009/059972 discloses numerous neoepitopes of some of the proteins described above as biomarkers of cardiovascular disease.

However, in none of the above mentioned reports is it suggested that measurements of peptide fragments based on antibodies binding to neo-epitopes as now claimed might be useful for the assessment of patients with fibrotic disease or inflammatory disease.

Figure 2:
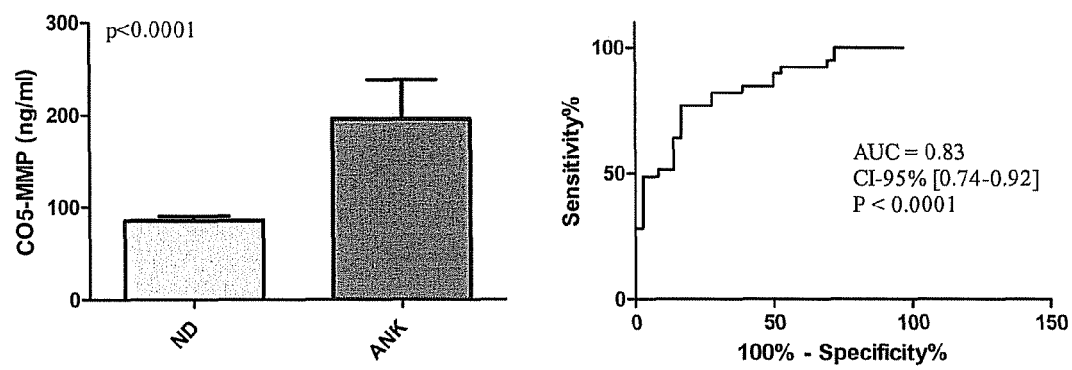

The invention will be further described and illustrated with reference to the following drawing in which:

FIG. 1 in panels A and B shows the results of investigating the specificity of a monoclonal antibody according to the invention; and FIG. 2 shows the results of investigating the amount of Collagen V neo-epitope bearing fragments in human serum from ankylosing spondylitis patients.

The present invention now provides a method of bioassay comprising, conducting an immunoassay to measure neo-epitope containing protein fragments naturally present in a patient biofluid sample, wherein said immunoassay is conducted by a method comprising:

contacting protein fragments naturally present in said sample with an immunological binding partner reactive with a neo-epitope formed by cleavage of a protein by a proteinase and measuring the extent of binding of peptide fragments to said immunological binding partner to measure therein protein fragments comprising said neo-epitope, wherein said neo-epitope is formed by cleavage of a said protein at any one of the cleavage sites shown in the following table:

TABLE 8

| Collagen Type I | |
|---|---|
| Protease | Cleavage sites marked '.'; SEQ ID NO in ( ) |
| FAP | Q.GAPGLQGMPG.E (1) |
| FAP | D.RGEPGPPGPAGFAGPPGAD.G (2) |
| FAP | D.GVRGLTGPIGPPGPAGAPGD.K (3) |
| FAP | A.GLPGAKGLTGSPGSPGPDGK.T (4) |
| FAP | D.AGPVGPPGPPGPPGPPGPPSAG.F (5) |
| FAP | D.GLNGLPGPIGPPGPRGRTGD.A (6) |
| FAP | S.PGKDGVRGLTGPIGPPGPAGAP.G (7) |
| FAP | L.PGPPGPPGPPGPPGLGGNFAPQ.L (8) |
| FAP | L.PGPPGPPGPPGPPGLGGNFAPQ.L (9) |
| FAP | P.GPPGPPGPPGLGGNFAPQLSY.G (10) |

TABLE 8-continued

| | |
|---|---|
| FAP | P.GPPGPPGPPGPPGLGGNFAPQL.S (11) |
| FAP | F.PGARGPSGPQGPGGPPGPKGNSG.E (12) |
| FAP | G.LPGPPGPPGPPGLGGNFAPQ.L (13) |
| FAP | G.LPGPPGPPGPPGLGGNFAPQ.L (14) |
| FAP | G.LPGPPGPPGPPGLGGNFAPQ.L (15) |
| FAP | D.AGPVGPPGPPGPPGPPGPPSAGFD.F (16) |
| FAP | D.GLNGLPGPIGPPGPRGRTGDAGPVGPPGPPGPPGPPGPPSAG.F (17) |
| FAP | P.GPPGPPGPPGPPGLGGNFAPQLSYGYDEKSTGGISVPGPMGP.S (18) |
| FAP | D.GLNGLPGPIGPPGPRGRTGDAGPVGPPGPPGPPGPPGPPSAGFD.F (19) |
| MMP9 + FAP | D.RGEPGPPGPAGFAGPPGAD.G (20) |
| MMP9 + FAP | D.GVRGLTGPIGPPGPAGAPGD.K (21) |
| MMP9 + FAP | D.AGPVGPPGPPGPPGPPSAG.F (22) |
| MMP9 + FAP | D.GLNGLPGPIGPPGPRGRTGD.A (23) |
| MMP9 + FAP | D.AGPVGPPGPPGPPGPPSAGF.D (24) |
| MMP9 + FAP | L.PGPPGPPGPPGPPGLGGNFAPQ.L (25) |
| MMP9 + FAP | P.GPPGPPGPPGLGGNFAPQLSY.G (26) |
| MMP9 + FAP | P.GPPGPPGPPGPPGLGGNFAPQL.S (27) |
| MMP9 + FAP | G.LPGPPGPPGPPGPPGLGGNFAPQ.L (28) |
| MMP9 + FAP | L.PGPPGPPGPPGPPGLGGNFAPQL.S (29) |
| MMP9 + FAP | P.GPPGPPGPPGPPSAGFDFSFLPQPPQEKAHDGGRYYR.A (30) |
| MMP9 + FAP | D.GLNGLPGPIGPPGPRGRTGDAGPVGPPGPPGPPGPPGPPSAGFD.F (19) |
| MMP9 | G.AAGPPGP.T (31) |
| MMP9 | P.VGPVGARGP.A (32) |
| MMP9 | P.AGPVGPVGARGP.A (33) |
| MMP9 | P.RGLPGPPGAPGP.Q (34) |
| MMP9 | G.EAGRPGEAGLPG.A (35) |
| MMP9 | Q.DGRPGPPGPPGA.R (36) |
| MMP9 | K.DGLNGLPGPIGPPGP.R (37) |
| MMP9 | G.AKGEPGPVGVQGPPGP.A (38) |
| MMP9 | P.AGARGNDGATGAAGPPGP.T (39) |
| MMP9 | P.VGPPGPPGPPGPPGPPSAGF.D (40) |
| MMP9 | A.GAPGKDGLNGLPGPIGPPGP.R (41) |
| MMP9 | D.AGPVGPPGPPGPPGPPGPPSAG.F (42) |
| MMP9 | S.AGAPGKDGLNGLPGPIGPPGP.R (43) |
| MMP9 | G.PPGPPGPPGLGGNFAPQLSYG.Y (44) |
| MMP9 | P.GPPGPPGPPGPPGLGGNFAPQL.S (45) |
| MMP9 | G.LPGPPGPPGPPGPPGLGGNFAPQ.L (46) |
| MMP9 | G.ERGPPGPMGPPGLAGPPGESGREGAPGAEGSPG.R (47) |
| FAP | 853'.IGNVGAPGAK'862 (alpha 2 chain) (48) |

TABLE 8-continued

| | |
|---|---|
| FAP | 462'.AGKEGPVGLP'471 (alpha 2 chain) (49) |
| FAP | 249'.IGSAGPPGFP'258 (alpha 2 chain) (50) |
| FAP | 1153'.DGLNGLPGPI'1162 (alpha 1 chain) (51) |
| FAP | 1153'.D(β)GLNGLPGPI'1162 (alpha 1 chain) (52) |
| FAP | 751'.KGADGSPGKD'760 (alpha 1 chain) (53) |
| FAP | 171'STGGISVPGP.'180 (alpha 1 chain) (54) |
| FAP | 167'.YDEKSTGGIS'176 (alpha 1 chain) (55) |

Collagen Type III

| Protease | Cleavage sites marked '.' SEQ ID NO in ( ) |
|---|---|
| FAP | E.AGIPGVPGAK.G (56) |
| FAP | P.KGDPGPPGIP.G (57) |
| FAP | G.PQGPKGDPGPP.G (58) |
| FAP | G.PGMRGMPGSPGGP.G (59) |
| FAP | D.GPPGPAGNTGAPGSPGVSGPKGD.A (60) |
| FAP | H.AGAQGPPGPPGINGSPGGKGEMGPAGIP.G (61) |
| FAP | D.GPRGPTGPIGPPGPAGQPGD.K (62) |
| MMP9 | D.GPPGPAGNTGAPGSPGVSGPKGD.A (63) |
| MMP9 | P.GSPGPAGQQGAIGSPGPAGPRGP.V (64) |
| MMP9 | G.ERGRPGLP.G (65) |
| MMP9 | G.KGDRGENGSPG.A (66) |
| MMP9 | E.PGKNGAKGEPGP.R (67) |
| MMP9 | S.PGERGETGPPGP.A (68) |
| MMP9 | P.GGPGADGVPGKDGP.R (69) |
| MMP9 | G.PPGKDGTSGHPGP.I (70) |
| MMP9 | R.GLPGPPGIKGPAGIPG.F (71) |
| MMP9 | L.PGENGAPGPMGPRGAPGE.R (72) |
| MMP9 | G.APGAPGGKGDAGAPGERGPP.G (73) |
| MMP9 | A.PGLKGENGLPGENGAPGPMGPRGAPG.E (74) |
| MMP9 | G.IAGITGARGLAGPPGMPGPRGSPGPQ.G (75) |
| MMP9 | G.SPGAKGEVGPAGSPGSNGAPGQRGEPGP.Q (76) |
| MMP9 | G.LKGENGLPGENGAPGPMGPRGAPGERGRPGLPGAA.G (77) |
| MMP9 + FAP | D.GPPGPAGNTGAPGSPGVSGPKGD.A (78) |
| ADAMTS-4 | 267'.GFDGRNGEKG'276 (79) |
| FAP | 533'.PGMRGMPGSP'542 (alpha 1 chain) (80) |
| Unknown | 642'.GLPGTGGPPG'651 (81) |
| Unknown | 652'ENGKPGEPGP.'661 (82) |
| Unknown | 861'.GERGSPGGPG'870 (83) |
| unknown | 899'PGKDGPPGPA.'908 (alpha 1 chain) (84) |
| MMP9, ADAMTS-4 | 442'.GLPGTGGPPG'451 (85) |

TABLE 8-continued

Collagen Type IV

| Protease | Cleavage sites marked '.' SEQ ID NO in ( ) |
|---|---|
| MMP9 | 333'.IVIGTGPLGE'342 (alpha 1 chain) (86) |
| MMP9 | 328'PGPPGIVIGT.'337 (alpha 1 chain) (87) |

Collagen Type V

| Protease | Cleavage sites marked '.' SEQ ID NO in ( ) |
|---|---|
| MMP2 | 920'ERGPRGITGK.'929 (alpha 1 chain) (88) |
| MMP2/9 | 1584'.RRNIDASQLL'1593 (alpha 1 chain) (89) |
| MMP2/9 | 229'.QQGGAGPTGP'238 (alpha 2 chain) (90) |
| MMP2/9 | 355'.QRGAHGMPGK'364 (alpha 2 chain) (91) |
| MMP9 | 525'.RVGKMGRPGA'534 (alpha 3 chain) (92) |
| MMP2/9 | 1317'.HMGREGREGE'1326 (alpha 3 chain) (93) |

Collagen Type VI

| Protease | Cleavage sites marked '.' |
|---|---|
| MMP8 | 873'.RIAVAQYSDD'883 (94) |
| MMP8 | 1192'.QLGTVQQVIS'1202 (95) |
| MMP12 | 1231'.RDVVFLIDGS'1241 (96) |

ApoE

| Protease | Cleavage sites marked '.' SEQ ID NO in ( ) |
|---|---|
| MMP9 | 81'.LMDETM'86 (97) |
| Cat K | 246'RLDEVK.'251 (98) |
| MMP9 | 101'TPVAEE.'106 (99) |
| Cat K | 126'.MEEMGS'131 (100) |

Biglycan

| Protease | Cleavage sites marked '.' SEQ ID NO in ( ) |
|---|---|
| MMP3 | 219'.KLTGIPKDLP'228 (101) |
| MMP3 | 226'DLPETLNELH.'235 (102) |
| MMP12 | 220'LTGIPKDLPE.'229 (103) |
| MMP13 | 329'.RAYYNGISLF'338 (104) |
| MMP13 | 334'GISLFNNPVP.'343 (105) |
| MMP12 | 87'.EISPDTTLLD'96 (106) |
| MMP12 | 97'LQNNDISELR.'106 (107) |
| MMP9 | 188'.IEMGGNPLENS'198 (108) |
| MMP9 | 200'FEPGAFDGLK.'209 (109) |
| MMP9 | 148'.NHLVEIPPNL'157 (110) |
| MMP9 | 151'VEIPPNLPSS.'160 (111) |
| MMP9 | 232'.NELHLDHNK' 240 (112) |
| MMP9 | 344'.YWEVQPATFR' 353 (113) |
| MMP9, MMP12 | 241'.IQAIELEDLL' 250 (114) |

TABLE 8-continued

Decorin

| Protease | Cleavage sites marked '.' SEQ ID NO in ( ) |
|---|---|
| ADAM-TS4 | 75'.VPKDLPPDTT'84 (115) |

Versican

| Protease | Cleavage sites marked '.' SEQ ID NO in ( ) |
|---|---|
| Cathepsin K | 3247'.YENWRPNQPD'3256 (116) |
| Cathepsin K | 3255'PDSFFSAGED.'3264 (117) |
| Cathepsin K | 3221'.HDYQWIGLN'3229 (118) |
| MMP8 | 3306'.KTFGKMKPRY'3316 (119) |
| MMP8 | 486'.SVTQIEQIEV'495 (120) |
| MMP8 | 491'EQIEVGPLVT.'500 (121) |

CRP

| Protease | Cleavage sites marked '.' SEQ ID NO in ( ) |
|---|---|
| Signal peptide | 013'LSHAFG.'018 (122) |
| MMP3/8/9, Cat S/K | 011'TSLSHA.'016 (123) |

Elastin

| Protease | Cleavage sites marked '.' SEQ ID NO in ( ) |
|---|---|
| Signal peptide | 21'LHPSRP.'26 (124) |
| ADAMTS1/4/8 MMP8/9 | 379'KAAKYG.'384 (125) |
| MMP9/12 | 547'GIGPGG.'552 (126) |

Lumican

| Protease | Cleavage sites marked '.' SEQ ID NO in ( ) |
|---|---|
| MMP9 | 75'NNQIDHIDEK.'84 (127) |

LAMC1

| Protease | Cleavage sites marked '.' SEQ ID NO in ( ) |
|---|---|
| MMP2/9 | 664'SAGYLDDVTL.'673 (128) |
| MMP9 | 1232'LNRKYEQAKN.'1241 (129) |

LAMA2

| Protease | Cleavage sites marked '.' SEQ ID NO in ( ) |
|---|---|
| MMP2 | 1240'.QFEGKKLMAY'1249 (130) |
| MMP2/9 | 2314'.GLWNFREKEG'2323 (131) |

LAMB1

| Protease | Cleavage sites marked '.' SEQ ID NO in ( ) |
|---|---|
| MMP9 | 209'ALDPAFKIED.'218 (132) |
| MMP2/9 | 1629'.SIESETAASE'1638 (133) |
| MMP2/9 | 1639'ETLFNASQRI.'1648 (134) |

TABLE 8-continued

| | LAMA5 | |
|---|---|---|
| Protease | Cleavage sites marked '.' SEQ ID NO in ( ) | |
| MMP9 | 2402'.NSRNQERLEE'2411 | (135) |
| MMP2/9 | 2901'EMDTLNEEVV.'2910 | (136) |
| MMP9 | 3056'DLELADAYYL.'3065 | (137) |

In amino acid sequences throughout this specification, P indicates hydroxyproline, M indicates oxidised methionine, and K indicates hydroxylysine.

The invention includes a method of bioassay comprising, conducting an immunoassay to measure neo-epitope containing protein fragments naturally present in a patient biofluid sample, wherein said immunoassay is conducted by a method comprising contacting protein fragments naturally present in said sample with an immunological binding partner reactive with a neo-epitope formed by cleavage of a protein by a proteinase and measuring the extent of binding of peptide fragments to said immunological binding partner to measure therein protein fragments comprising said neo-epitope, wherein said protein is ApoE, or a laminin. These proteins are preferably human and the samples are preferably human but the samples and/or the proteins may be mammalian including especially rodent, for instance mouse or rat, or may be dog or primate including monkey.

The method may include associating an elevation of said measure in said patient above a normal level with the presence of fibrosis, or inflammatory disease.

Optionally, an elevated result in an immunoassay according to this invention is associated with skin fibrosis, lung fibrosis, or liver fibrosis or cardiovascular disease. Optionally, an elevated result in an immunoassay according to the invention may be associated with an inflammatory condition, such as ankylosing spondylitis. The method may comprise the preliminary step of obtaining a patient biofluid sample.

Said immunological binding partner may have specific binding affinity for peptide fragments comprising a C-terminal neoepitope or an N-terminal neoepitope.

Specific reactivity with or immunological affinity for a neo-epitope will imply that the relevant immunological binding partner is not reactive with intact protein from which the neo-epitope derives. Preferably, said immunological binding partner is not reactive with a neo-epitope sequence, such as a sequence listed below, if the sequence is prolonged past the respective cleavage site.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

Preferably, the neo-epitope sequence to which the immunological binding partner binds is not found in any other protein or is not found in any of the other proteins to which the method of the invention relates.

Several candidate proteases may be responsible for the digestion of proteins in the fibrotic tissues. Most likely, this is the result of the large range of complicated processes resulting in different neo-epitope profiles dependent on the levels of disease.

Collagen Assays
Collagen type I

We have determined that the enzymes listed in the following table cleave type I collagen at least the following cleavage sites (marked "."):

TABLE 9

Collagen type I cleavage sites.

| Protease | Cleavage sites marked '.' |
|---|---|
| FAP | Q.GAPGLQGMPG.E |
| FAP | D.RGEPGPPGPAGFAGPPGAD.G |
| FAP | D.GVRGLTGPIGPPGPAGAPGD.K |
| FAP | A.GLPGAKGLTGSPGSPGPDGK.T |
| FAP | D.AGPVGPPGPPGPPGPPGPPSAG.F |
| FAP | D.GLNGLPGPIGPPGPRGRTGD.A |
| FAP | S.PGKDGVRGLTGPIGPPGPAGAP.G |
| FAP | L.PGPPGPPGPPGPPGLGGNFAPQ.L |
| FAP | L.PGPPGPPGPPGPPGLGGNFAPQ.L |
| FAP | P.GPPGPPGPPGLGGNFAPQLSY.G |
| FAP | P.GPPGPPGPPGPPGLGGNFAPQL.S |
| FAP | F.PGARGPSGPQGPGGPPGPKGNSG.E |
| FAP | G.LPGPPGPPGPPGPPGLGGNFAPQ.L |

TABLE 9-continued

Collagen type I cleavage sites.

| Protease | Cleavage sites marked '.' |
|---|---|
| FAP | G.LPGPPGPPGPPGPPGLGGNFAPQ.L |
| FAP | G.LPGPPGPPGPPGPPGLGGNFAPQ.L |
| FAP | D.AGPVGPPGPPGPPGPPGPPSAGFD.F |
| FAP | D.GLNGLPGPIGPPGPRGRTGDAGPVGPPGPPGPPGPPGPPSAG.F |
| FAP | D.GLNGLPGPIGPPGPRGRTGDAGPVGPPGPPGPPGPPGPPSAG.F |
| FAP | P.GPPGPPGPPGPPGLGGNFAPQLSYGYDEKSTGGISVPGPMGP.S |
| FAP | D.GLNGLPGPIGPPGPRGRTGDAGPVGPPGPPGPPGPPGPPSAGFD.F |
| MMP9 + FAP | D.RGEPGPPGPAGFAGPPGAD.G |
| MMP9 + FAP | D.GVRGLTGPIGPPGPAGAPGD.K |
| MMP9 + FAP | D.AGPVGPPGPPGPPGPPGPPSAG.F |
| MMP9 + FAP | D.GLNGLPGPIGPPGPRGRTGD.A |
| MMP9 + FAP | D.AGPVGPPGPPGPPGPPGPPSAGF.D |
| MMP9 + FAP | L.PGPPGPPGPPGPPGPPGLGGNFAPQ.L |
| MMP9 + FAP | P.GPPGPPGPPGLGGNFAPQLSY.G |
| MMP9 + FAP | P.GPPGPPGPPGPPGLGGNFAPQL.S |
| MMP9 + FAP | G.LPGPPGPPGPPGPPGLGGNFAPQ.L |
| MMP9 + FAP | L.PGPPGPPGPPGPPGLGGNFAPQL.S |
| MMP9 + FAP | P.GPPGPPGPPGPPSAGFDFSFLPQPPQEKAHDGGRYYR.A |
| MMP9 + FAP | D.GLNGLPGPIGPPGPRGRTGDAGPVGPPGPPGPPGPPGPPSAGFD.F |
| MMP9 | G.AAGPPGP.T |
| MMP9 | P.VGPVGARGP.A |
| MMP9 | P.AGPVGPVGARGP.A |
| MMP9 | P.RGLPGPPGAPGP.Q |
| MMP9 | G.EAGRPGEAGLPG.A |
| MMP9 | Q.DGRPGPPGPPGA.R |
| MMP9 | K.DGLNGLPGPIGPPGP.R |
| MMP9 | G.AKGEPGPVGVQGPPGP.A |
| MMP9 | P.AGARGNDGATGAAGPPGP.T |
| MMP9 | P.VGPPGPPGPPGPPGPPSAGF.D |
| MMP9 | A.GAPGKDGLNGLPGPIGPPGP.R |
| MMP9 | D.AGPVGPPGPPGPPGPPGPPSAG.F |
| MMP9 | S.AGAPGKDGLNGLPGPIGPPGP.R |
| MMP9 | G.PPGPPGPPGLGGNFAPQLSYG.Y |
| MMP9 | P.GPPGPPGPPGPPGLGGNFAPQL.S |
| MMP9 | G.LPGPPGPPGPPGPPGLGGNFAPQ.L |
| MMP9 | G.ERGPPGPMGPPGLAGPPGESGREGAPGAEGSPG.R |
| FAP | P.IGNVGAPGAK (alpha 1 chain) |
| FAP | P.AGKEGPVGLP (alpha 2 chain) |

TABLE 9-continued

Collagen type I cleavage sites.

| Protease | Cleavage sites marked '.' |
|---|---|
| FAP | P.IGSAGPPGFP (alpha 2 chain) |
| FAP | 853'.IGNVGAPGAK'862 (alpha 2 chain) |
| FAP | 462'.AGKEGPVGLP'471 (alpha 2 chain) |
| FAP | 249'.IGSAGPPGFP'258 (alpha 2 chain) |
| FAP | 1153'.DGLNGLPGPI'1162 (alpha 1 chain) |
| FAP | 1153'.D(β)GLNGLPGPI'1162 (alpha 1 chain) |
| FAP | 751'.KGADGSPGKD'760 (alpha 1 chain) |
| FAP | 171'STGGISVPGP.'180 (alpha 1 chain) |
| FAP | 167'.YDEKSTGGIS'176 (alpha 1 chain) |
| FAP | Q.GAPGLQGMPG.E |
| FAP | D.RGEPGPPGPAGFAGPPGAD.G |
| FAP | D.GVRGLTGPIGPPGPAGAPGD.K |
| FAP | A.GLPGAKGLTGSPGSPGPDGK.T |
| FAP | D.AGPVGPPGPPGPPPGPPGPPSAG.F |
| FAP | D.GLNGLPGPIGPPGPRGRTGD.A |
| FAP | S.PGKDGVRGLTGPIGPPGPAGAP.G |
| FAP | L.PGPPGPPGPPGPPGLGGNFAPQ.L |
| FAP | L.PGPPGPPGPPGPPGLGGNFAPQ.L |
| FAP | P.GPPGPPGPPGLGGNFAPQLSY.G |
| FAP | P.GPPGPPGPPGPPGLGGNFAPQL.S |
| FAP | F.PGARGPSGPQGPGGPPGPKGNSG.E |
| FAP | G.LPGPPGPPGPGPPGLGGNFAPQ.L |
| FAP | G.LPGPPGPPGPPGPPGLGGNFAPQ.L |
| FAP | G.LPGPPGPPGPPGPPGLGGNFAPQ.L |
| FAP | D.AGPVGPPGPPGPPPGPPGPPSAGFD.F |
| FAP | D.GLNGLPGPIGPPGPRGRTGDAGPVGPPGPPGPPPGPPGPPSAG.F |
| FAP | D.GLNGLPGPIGPPGPRGRTGDAGPVGPPGPPGPPPGPPGPPSAG.F |
| FAP | P.GPPGPPGPPGPPGLGGNFAPQLSYGYDEKSTGGISVPGMGP.S |
| FAP | D.GLNGLPGPIGPPGPRGRTGDAGPVGPPGPPGPPPGPPGPPSAGFD.F |
| MMP9 + FAP | D.RGEPGPPGPAGFAGPPGAD.G |
| MMP9 + FAP | D.GVRGLTGPIGPPGPAGAPGD.K |
| MMP9 + FAP | D.AGPVGPPGPPGPPGPPSAG.F |
| MMP9 + FAP | D.GLNGLPGPIGPPGPRGRTGD.A |
| MMP9 + FAP | D.AGPVGPPGPPGPPGPPGPPSAGF.D |
| MMP9 + FAP | L.PGPPGPPGPPGPPGLGGNFAPQ.L |
| MMP9 + FAP | P.GPPGPPGPPGLGGNFAPQLSY.G |
| MMP9 + FAP | P.GPPGPPGPPGPPGLGGNFAPQL.S |
| MMP9 + FAP | G.LPGPPGPPGPPGPPGLGGNFAPQ.L |

TABLE 9-continued

Collagen type I cleavage sites.

| Protease | Cleavage sites marked '.' |
|---|---|
| MMP9 + FAP | L.PGPPGPPGPPGPPGLGGNFAPQL.S |
| MMP9 + FAP | P.GPPGPPGPPGPPSAGFDFSFLPQPPQEKAHDGGRYYR.A |
| MMP9 + FAP | D.GLNGLPGPIGPPGPRGRTGDAGPVGPPGPPGPPGPPGPPSAGFD.F |
| MMP9 | G.AAGPPGP.T |
| MMP9 | P.VGPVGARGP.A |
| MMP9 | P.AGPVGPVGARGP.A |
| MMP9 | P.RGLPGPPGAPGP.Q |
| MMP9 | G.EAGRPGEAGLPG.A |
| MMP9 | Q.DGRPGPPGPPGA.R |
| MMP9 | K.DGLNGLPGPIGPPGP.R |
| MMP9 | G.AKGEPGPVGVQGPPGP.A |
| MMP9 | P.AGARGNDGATGAAGPPGP.T |
| MMP9 | P.VGPPGPPGPPGPPGPPSAGF.D |
| MMP9 | A.GAPGKDGLNGLPGPIGPPGP.R |
| MMP9 | D.AGPVGPPGPPGPPGPPGPPSAG.F |
| MMP9 | S.AGAPGKDGLNGLPGPIGPPGP.R |
| MMP9 | G.PPGPPGPPGLGGNFAPQLSYG.Y |
| MMP9 | P.GPPGPPGPPGPPGLGGNFAPQL.S |
| MMP9 | G.LPGPPGPPGPPGPPGLGGNFAPQ.L |
| MMP9 | G.ERGPPGPMGPPGLAGPPGESGREGAPGAEGSPG.R |
| FAP | P.IGNVGAPGAK (alpha 1 chain) |
| FAP | P.AGKEGPVGLP (alpha 2 chain) |
| FAP | P.IGSAGPPGFP (alpha 2 chain) |

Suitable immunological binding partners may therefore be specifically reactive with any of the following sequences at the N terminal of a peptide:

TABLE 10

N-terminal sequences of protease generated peptide fragments of Collagen type I. (The symbol '.' indicates the cleavage site)
Cleavage sites marked '.'/SEQ ID NO ( )

| | |
|---|---|
| .AAGPPG | (138) |
| .AGPVGP | (139) |
| .DGRPGP | (140) |
| .EAGRPG | (141) |
| .GAPGLQ | (142) |
| .GLNGLP | (143) |
| .GLNGLP | (144) |
| .GLPGAK | (145) |
| .GPPGPP | (146) |
| .GPPGPP | (147) |
| .GVRGLT | (148) |
| .LPGPPG | (149) |
| .LPGPPG | (150) |
| .PGARGP | (151) |
| .PGKDGV | (152) |
| .PGPPGP | (153) |
| .PGPPGP | (154) |

TABLE 10-continued

N-terminal sequences of protease generated peptide fragments of Collagen type I. (The symbol '.' indicates the cleavage site) Cleavage sites marked '.'/SEQ ID NO ( )

| Sequence | SEQ ID NO |
|---|---|
| .PGPPGP | (155) |
| .RGEPGP | (156) |
| .RGLPGP | (157) |
| .VGPVGA | (158) |
| .DGLNGL | (159) |
| .AKGEPG | (160) |
| .AGARGN | (161) |
| .VGPPGP | (162) |
| .GAPGKD | (163) |
| .IGSAGP | (164) |
| .AGAPGK | (165) |
| .PPGPPG | (166) |
| .GPPGPP | (167) |
| .YDEKST | (168) |
| .ERGPPG | (169) |
| .IGNVGA | (170) |
| .AGKEGP | (171) |
| .KGADGS | (172) |
| .D(β)GLNGLP | (173) |

Alternatively, suitable immunological binding partners may be specifically reactive with any of the following sequences at the C terminal of a peptide:

TABLE 11

C-terminal sequences of protease generated peptide fragments of Collagen type I (The symbol '.' indicates the cleavage site). Cleavage sites marked '.'/SEQ ID NO ( )

| Sequence | SEQ ID NO |
|---|---|
| AEGSPG. | (174) |
| AGAPGD. | (175) |
| AGPPGP. | (176) |
| AGPPGP. | (177) |
| APQLSY. | (178) |
| APQLSY. | (179) |
| EAGLPG. | (180) |
| GGRYYR. | (181) |
| GNFAPQ. | (182) |
| GNFAPQ. | (183) |
| GPAGAP. | (184) |
| GPPGAD. | (185) |
| GPPSAG. | (186) |
| IGPPGP. | (187) |
| IGPPGP. | (188) |
| IGPPGP. | (189) |
| ISVPGP. | (190) |
| LQGMPG. | (191) |
| NFAPQL. | (192) |
| PGAPGP. | (193) |
| PGPDGK. | (194) |
| PGPMGP. | (195) |
| PGPPGA. | (196) |
| PKGNSG. | (197) |
| PPSAGF. | (198) |
| PQLSYG. | (199) |
| PSAGFD. | (200) |
| QGPPGP. | (201) |
| RGRTGD. | (202) |
| VGARGP. | (203) |

Collagen type III

We have determined that the enzymes listed in the following table cleave type III collagen at least the following cleavage sites (marked *):

TABLE 12

Cleavage sites in collagen type III.

| Protease | Cleavage sites marked '.' |
|---|---|
| FAP | E.AGIPGVPGAK.G |
| FAP | P.KGDPGPPGIP.G |
| FAP | G.PQGPKGDPGPP.G |
| FAP | G.PGMRGMPGSPGGP.G |
| FAP | D.GPPGPAGNTGAPGSPGVSGPKGD.A |
| FAP | H.AGAQGPPGPPGINGSPGGKGEMGPAGIP.G |
| FAP | D.GPRGPTGPIGPPGPAGQPGD.K |
| MMP9 | D.GPPGPAGNTGAPGSPGVSGPKGD.A |
| MMP9 | P.GSPGPAGQQGAIGSPGPAGPRGP.V |
| MMP9 | G.ERGRPGLP.G |
| MMP9 | G.KGDRGENGSPG.A |
| MMP9 | E.PGKNGAKGEPGP.R |
| MMP9 | S.PGERGETGPPGP.A |

TABLE 12-continued

Cleavage sites in collagen type III.

| Protease | Cleavage sites marked '.' |
|---|---|
| MMP9 | P.GGPGADGVPGKDGP.R |
| MMP9 | G.PPGKDGTSGHPGP.I |
| MMP9 | R.GLPGPPGIKGPAGIPG.F |
| MMP9 | L.PGENGAPGPMGPRGAPGE.R |
| MMP9 | G.APGAPGGKGDAGAPGERGPP.G |
| MMP9 | A.PGLKGENGLPGENGAPGPMGPRGAPG.E |
| MMP9 | G.IAGITGARGLAGPPGMPGPRGSPGPQ.G |
| MMP9 | G.SPGAKGEVGPAGSPGSNGAPGQRGEPGP.Q |
| MMP9 | G.LKGENGLPGENGAPGPMGPRGAPGERGRPGLPGAA.G |
| MMP9 + FAP | D.GPPGPAGNTGAPGSPGVSGPKGD.A |
| ADAMTS-4 | 267'.GFDGRNGEKG'276 |
| FAP | 533'.PGMRGMPGSP'542 (alpha 1 chain) |
| Unknown | 642'.GLPGTGGPPG'651 |
| Unknown | 652'ENGKPGEPGP.'661 |
| Unknown | 861'.GERGSPGGPG'870<br>697'GAGPPGPEGG'706 (alpha 1 chain)<br>804'GPPGPAGFPG'813 (alpha 1 chain)<br>899'PGKDGPPGPA.'908 (alpha 1 chain)<br>1008'GEPGRDGNPG'1017 (alpha 1 chain) |
| MMP9, ADAMTS-4 | 442'.GLPGTGGPPG'451 |

The immunological binding partner may be one specifically reactive with a C-terminal or N-terminal neoepitope formed by cleavage of type III collagen.

Suitable immunological binding partners may therefore be specifically reactive with any of the following sequences at the N terminal of a peptide:

TABLE 13

N-terminal sequences of protease generated peptide fragments of Collagen type III. Cleavage sites marked '.'/SEQ ID NO ( )

| Sequence | SEQ ID NO |
|---|---|
| .AGAQGP | (204) |
| .AGIPGV | (205) |
| .APGAPG | (206) |
| .ERGRPG | (207) |
| .GERGSP | (208) |
| .GFDGRN | (209) |
| .GGPGAD | (210) |
| .GLPGPP | (211) |
| .GLPGTG | (212) |
| .GPPGPA | (213) |
| .GPRGPT | (214) |
| .GSPGPA | (215) |
| .IAGITG | (216) |
| .KGDPGP | (217) |
| .KGDRGE | (218) |
| .LKGENG | (219) |
| .PGENGA | (220) |
| .PGERGE | (221) |
| .PGKNGA | (222) |
| .PGLKGE | (223) |
| .PGMRGM | (224) |
| .PPGKDG | (225) |
| .PQGPKG | (226) |
| .SPGAKG | (227) | or with any of the following sequences at the C-terminal of a peptide:

TABLE 14

C-terminal sequences of protease generated peptide fragments of Collagen type III. Cleavage sites marked '.'/SEQ ID NO ( )

| Sequence | SEQ ID NO |
|---|---|
| AGQPGD. | (228) |
| ENGSPG. | (229) |
| GDPGPP. | (230) |
| GERGPP. | (231) |
| GLPGAA. | (232) |
| GPAGIP. | (233) |
| GPPGIP. | (234) |
| GPPGPA. | (235) |
| GRPGLP. | (236) |
| GSPGGP. | (237) |
| GSPGPQ. | (238) |
| GVPGAK. | (239) |
| KGEPGP. | (240) |
| PAGIPG. | (241) |
| AGPRGP. | (242) |
| PGEPGP. | (243) |
| PGKDGP. | (244) |
| PRGAPG. | (245) |
| RGAPGE. | (246) |
| RGEPGP. | (247) |

TABLE 14-continued

C-terminal sequences of protease generated peptide
fragments of Collagen type III.
Cleavage sites marked '.'/SEQ ID NO ( )

| | |
|---|---|
| SGHPGP. | (248) |
| SGPKGD. | (249) |
| TGPPGP. | (250) |

Collagen IV

We have determined that the enzymes listed in the following table cleave type IV collagen at least the following cleavage sites (marked "."):

TABLE 15

Cleavage fragments of collagen type IV

| Protease | Cleavage sites marked '.' |
|---|---|
| MMP9 | 333'.IVIGTGPLGE'342 (alpha 1 chain) |
| MMP9 | 328'PGPPGIVIGT.'337 (alpha 1 chain) |

The immunological binding partner may be one specifically reactive with a C-terminal or N-terminal neoepitope formed by cleavage of type IV collagen.

Suitable immunological binding partners may therefore be specifically reactive with the following sequence at the N terminal of a peptide:

TABLE 16

N-terminal sequence of protease generated peptide
fragments of Collagen type IV.
Cleavage site marked '.'/SEQ ID NO ( )

| | |
|---|---|
| .IVIGTG | (251) | or with the following sequence at the C-terminal of a peptide:

TABLE 17

C-terminal sequences of protease generated peptide
fragments of Collagen type IV.
Cleavage site marked '.'/SEQ ID NO ( )

| | |
|---|---|
| GIVIGT. | (252) |

Collagen V

We have determined that the enzymes listed in the following table cleave type V collagen at least the following cleavage sites (marked "." or in the absence of a at the end of the sequence):

TABLE 18

Cleavage fragments of collagen type V

| Protease | Cleavage sites marked '.' |
|---|---|
| MMP2 | 920'ERGPRGITGK.'929 (alpha 1 chain) |
| MMP2/9 | 1584'.RRNIDASQLL'1593 (alpha 1 chain) |
| MMP2/9 | 229'.QQGGAGPTGP'238 (alpha 2 chain) |
| MMP2/9 | 355'.QRGAHGMPGK'364 (alpha 2 chain) |

TABLE 18-continued

Cleavage fragments of collagen type V

| Protease | Cleavage sites marked '.' |
|---|---|
| MMP9 | 525'.RVGKMGRPGA'534 (alpha 3 chain) |
| MMP2/9 | 1317'.HMGREGREGE'1326 (alpha 3 chain) |

The immunological binding partner may be one specifically reactive with a C-terminal or N-terminal neoepitope formed by cleavage of type V collagen.

Suitable immunological binding partners may therefore be specifically reactive with any of the following sequences at the N terminal of a peptide:

TABLE 19

N-terminal sequences of protease generated peptide
fragments of Collagen type V.
Cleavage sites marked '.'/SEQ ID NO ( )

| | |
|---|---|
| .RRNIDA | (253) |
| .QQGGAG | (254) |
| .QRGAHG | (255) |
| .RVGKMG | (256) |
| .HMGREG | (257) | or with the following sequence at the C-terminal of a peptide:

TABLE 20

C-terminal sequence of a protease generated
peptide fragment of Collagen type V.
Cleavage sites marked '.'/SEQ ID NO ( )

| | |
|---|---|
| RGITGK. | (258) |

Collagen VI

We have determined that the enzymes listed in the following table cleave type VI collagen at least the following cleavage sites (marked "." or in the absence of a '.', at the end of the sequence):

TABLE 21

Cleavage fragments of collagen type VI

| Protease | Cleavage sites marked '.' |
|---|---|
| MMP8 | 873'. RIAVAQYSDD 883' |
| MMP8 | 1192'. QLGTVQQVIS 1202' |
| MMP12 | 1231'.RDVVFLIDGS 1241' |

The immunological binding partner may be one specifically reactive with an N-terminal neoepitope formed by cleavage of type VI collagen.

Suitable immunological binding partners may therefore be specifically reactive with any of the following sequences at the N terminal of a peptide:

TABLE 22

N-terminal sequences of protease generated peptide fragments of Collagen type VI. Cleavagesites marked '.'/SEQ ID NO ( )

| | |
|---|---|
| .RIAVAQ | (259) |
| .QLGTVQ | (260) |
| .RDVVFL | (261) |

Proteoglycans

In another aspect of the invention, said peptide fragments are fragments of proteoglycans versican, lumican, biglycan and decorin, which are all identified in fibrotic tissue.

Several candidate proteases may be responsible for the digestion of proteoglycans in fibrotic lesions We have determined that the enzymes listed in Table 23 generate biglycan fragments, resulting in at least following cleavage products:

Biglycan

TABLE 23

Cleavage fragments of biglycan

| Protease | Cleavage sites marked '.' |
|---|---|
| MMP3 | 219'.KLTGIPKDLP'228 |
| MMP3 | 226'DLPETLNELH.'235 |
| MMP12 | 220'LTGIPKDLPE.'229 |
| MMP13 | 329'.RAYYNGISLF'338 |
| MMP13 | 334'GISLFNNPVP.'343 |
| MMP12 | 87'.EISPDTTLLD'96 |
| MMP12 | 97'LQNNDISELR.'106 |
| MMP9 | 188'.IEMGGNPLENS'198 |
| MMP9 | 200'FEPGAFDGLK.'209 |
| MMP9 | 148'.NHLVEIPPNL'157 |
| MMP9 | 151'VEIPPNLPSS.'160 |
| MMP9 | 232'.NELHLDHNK'240 |
| MMP9 | 344'.YWEVQPATFR'353 |
| MMP9, MMP12 | 241'.IQAIELEDLL'250 |

The immunological binding partner may be one specifically reactive with a C-terminal or N-terminal neo-epitope formed by cleavage of type biglycan.

Suitable immunological binding partners may therefore be specifically reactive with any of the following at the N terminal of a peptide:

TABLE 24

N-terminal sequences of protease generated peptide fragments of biglycan. Cleavage sites marked '.'/SEQ ID NO ( )

| | |
|---|---|
| .KLTGIP | (262) |
| .RAYYNG | (263) |
| .EISPDT | (264) |

TABLE 24-continued

N-terminal sequences of protease generated peptide fragments of biglycan. Cleavage sites marked '.'/SEQ ID NO ( )

| | |
|---|---|
| .IEMGGN | (265) |
| .NHLVEI | (266) |
| .NELHLD | (267) |
| .YWEVQP | (268) |
| .IQAIEL | (269) | or with the following sequences in Table 25, at the C-terminal of a peptide:

TABLE 25

C-terminal sequence of protease generated peptide fragment of biglycan. Cleavage sites marked '.'/SEQ ID NO ( )

| | |
|---|---|
| TLNELH. | (270) |
| PKDLPE. | (271) |
| FNNPVP. | (272) |
| DISELR. | (273) |
| AFDGLK. | (274) |
| PNLPSS. | (275) |

Decorin

TABLE 26

Cleavage fragment of decorin

| Protease | Cleavage site marked '.' |
|---|---|
| ADAM-TS4 | 75'.VPKDLPPDTT'84 |

The immunological binding partner may be one specifically reactive with an N-terminal neo-epitope formed by cleavage, of decorin.

Suitable immunological binding partners may therefore be specifically reactive with the following at the N terminal of a peptide:

TABLE 27

N-terminal sequence of protease generated peptide fragments of decorin. Cleavage sites marked '.'/SEQ ID NO ( )

| | |
|---|---|
| .VPKDLP | (276) |

Versican

TABLE 28

Cleavage fragments of versican

| Protease | Cleavage sites marked '.' |
|---|---|
| Cathepsin K | 3247'.YENWRPNQPD'3256 |
| Cathepsin K | 3255'PDSFFSAGED.'3264 |

TABLE 28-continued

Cleavage fragments of versican

| Protease | Cleavage sites marked '.' |
|---|---|
| Cathepsin K | 3221'.HDYQWIGLN'3229 |
| MMP8 | 3306'.KTFGKMKPRY'3316 |
| MMP8 | 486'.SVTQIEQIEV'495 |
| MMP8 | 491'EQIEVGPLVT.'500 |

The immunological binding partner may be one specifically reactive with a C-terminal or N-terminal neo-epitope formed by cleavage of type versican.

Suitable immunological binding partners may therefore be specifically reactive with any of the following at the N terminal of a peptide:

TABLE 29

N-terminal sequences of protease generated peptide fragments of versican.
Cleavage sites marked '.'/SEQ ID NO ( )

| | |
|---|---|
| .YENWRP | (277) |
| .HDYQWI | (278) |
| .KTFGKM | (279) |
| .SVTQIE | (304) | or with either of the following sequences in Table 30, at the C-terminal of a peptide:

TABLE 30

C-terminal sequences of protease generated peptide fragments of versican.
Cleavage sites marked '.'/SEQ ID NO ( )

| | |
|---|---|
| FSAGED. | (280) |
| VGPLVT. | (281) |

Lumican

TABLE 31

Cleavage fragment of lumican

| Protease | Cleavage sites marked '.' |
|---|---|
| MMP9 | 75'NNQIDHIDEK.'84 |

The immunological binding partner may be one specifically reactive with an N-terminal neo-epitope formed by cleavage of type lumican.

Suitable immunological binding partners may therefore be specifically reactive with the following sequence at the C-terminal of a peptide:

TABLE 32

C-terminal sequences of protease generated peptide fragment of lumican.
Cleavage sites marked '.'/SEQ ID NO ( )

| | |
|---|---|
| DHIDEK. | (282) |

CRP

Several candidate proteases may be responsible for the digestion of CRP in fibrotic tissue the literature reports many different proteases in fibrotic tissue. Most likely, this is the result of the large range of complicated processes eventually leading to fibrosis. However, in our assessment, early phases may consist of a range of MMPs, whereas later stages may rely more on cathepsin K degradation of the matrix, resulting in different neo-epitope profiles dependent on the levels of disease. We have through a range of in vitro cleavages of pure native proteins determined that the enzymes listed in the following tables of cleaved CRP at least following cleavage sites marked '.' in Table 33.

TABLE 33

CRP fragments generated by specific proteases.

| Protease | Cleavage sites marked '.' |
|---|---|
| Unknown | 013'LSHAFG.'018 |
| MMP3/8/9, Cat S/K | 011'TSLSHA.'016 |

Accordingly, in a method of the invention, said peptide fragments preferably comprise a neo-epitope formed by cleavage of CRP by a protease at a site marked by the sign in either one of the above partial sequences of CRP in Table 33.

The immunological binding partner may be one specifically reactive with an N-terminal neo-epitope formed by cleavage of CRP. Suitable immunological binding partners may therefore be specifically reactive with either of the following sequences at the C-terminal of a peptide:

TABLE 34

C-terminal sequences of protease generated peptide fragments of CRP.
Cleavage sites marked '.'/SEQ ID NO ( )

| | |
|---|---|
| LSHAFG. | (283) |
| TSLSHA. | (284) |

Elastin

Several candidate proteases may be responsible for the digestion of elastin in fibrotic tissue. We have through a range of in vitro cleavages of pure native proteins determined that the enzymes listed in the following table cleaved elastin at least at the cleavage sites at each end of the following sequences or at the cleavage sites marked '.':

TABLE 35

Elastin* fragments generated by specific proteases.

| Protease | Cleavage sites marked '.' |
|---|---|
| Signal peptide | 21'LHPSRP.'26 |
| ADAMTS1/4/8 MMP8/9 | 379'KAAKYG.'384 |
| MMP9/12 | 547'GIGPGG.'552 |

*Aminoacid residue numbers are from the human elastin sequence

Accordingly, in a method of the invention, said peptide fragments preferably comprise a neo-epitope formed by cleavage of elastin by a protease at a C-terminal site, in any one of the partial sequences of elastin in Table 35.

The immunological binding partner may be one specifically reactive with a C-terminal neo-epitope formed by cleavage of elastin.

Suitable immunological binding partners may therefore be specifically reactive with any of the following sequences at the C-terminal of a peptide:

TABLE 36

C-terminal sequences of protease generated peptide fragments of Elastin.
Cleavage sites marked '.'/SEQ ID NO ( )

| | |
|---|---|
| LHPSRP. | (285) |
| KAAKYG. | (286) |
| GIGPGG. | (287) |

ApoE

Several candidate proteases may be responsible for the digestion of ApoE in fibrotic tissue. We have through a range of in vitro cleavages of pure native proteins determined that the enzymes listed in the following table cleaved ApoE at least at the cleavage sites at each end of the following sequences or at the cleavage sites marked '.':

TABLE 37

Cleavage sites of ApoE

| Protease | Cleavage sites marked '.' |
|---|---|
| MMP9 | 81'.LMDETM'86 |
| Cat K | 246'RLDEVK.'251 |
| MMP9 | 101'TPVAEE.'106 |
| Cat K | 126'.MEEMGS'131 |

Accordingly, in a method of the invention, said peptide fragments preferably comprise a neo-epitope formed by cleavage of ApoE by a protease at an N- or C-terminal site, or where indicated a site marked by the sign in any one of the partial sequences of ApoE in Table 37.

The immunological binding partner may be one specifically reactive with a C-terminal or N-terminal neo-epitope formed by cleavage of ApoE.

Suitable immunological binding partners may therefore be specifically reactive with either of the following sequences at the N terminal of a peptide:

TABLE 38

N-terminal sequences of protease generated peptide fragments of ApoE.
Cleavage sites marked '.'/SEQ ID NO ( )

| | |
|---|---|
| .LMDETM | (288) |
| .MEEMGS | (289) | or with either of the following sequences at the C-terminal of a peptide:

TABLE 39

C-terminal sequences of protease generated peptide fragments of ApoE.
Cleavage sites marked '.'/SEQ ID NO ( )

| | |
|---|---|
| RLDEVK. | (290) |
| TPVAEE. | (291) |

LAMC1

Several candidate proteases may be responsible for the digestion of LAMC1 in fibrotic tissue. We have through a range of in vitro cleavages of pure native proteins determined that enzymes cleave LAMC1 at least at the cleavage sites at each end of the following sequences or at the cleavage sites marked '.':

TABLE 40

Cleavage sites of LAMC1

| Protease | Cleavage sites marked '.' |
|---|---|
| MMP2/9 | 664'SAGYLDDVTL.'673 |
| MMP9 | 1232'LNRKYEQAKN.'1241 |

Accordingly, in a method of the invention, said peptide fragments preferably comprise a neo-epitope formed by cleavage of LAMC1 by a protease at a C-terminal site in either one of the partial sequences of LAMC1 in Table 40.

The immunological binding partner may be one specifically reactive with a C-terminal or N-terminal neo-epitope formed by cleavage of LAMC1.

Suitable immunological binding partners may therefore be specifically reactive with any of the following sequences at the C-terminal of a peptide:

TABLE 41

C-terminal sequences of protease generated peptide fragments of LAMC1.
Cleavage sites marked '.'/SEQ ID NO ( )

| | |
|---|---|
| LDDVTL. | (292) |
| YEQAKN. | (293) |

LAMA2

Several candidate proteases may be responsible for the digestion of LAMA2 in fibrotic tissue. We have through a range of in vitro cleavages of pure native proteins determined that enzymes cleave LAMA2 at least at the cleavage sites at each end of the following sequences or at the cleavage sites marked '.':

TABLE 42

Cleavage sites of LAMA2

| Protease | Cleavage sites marked '.' |
|---|---|
| MMP2 | 1240'.QFEGKKLMAY'1249 |
| MMP2/9 | 2314'.GLWNFREKEG'2323 |

Accordingly, in a method of the invention, said peptide fragments preferably comprise a neo-epitope formed by cleavage of LAMA2 by a protease at an N-terminal site, in either one of the partial sequences of LAMA2 in Table 42.

The immunological binding partner may be one specifically reactive with a C-terminal or N-terminal neo-epitope formed by cleavage of LAMA2.

Suitable immunological binding partners may therefore be specifically reactive with any of the following sequences at the N terminal of a peptide:

TABLE 43

N-terminal sequences of protease generated peptide fragments of LAMA2.

| Protease | Cleavage sites marked '.'/SEQ ID NO ( ) |
|---|---|
| MMP2 | .QFEGKK (294) |
| MMP2/9 | .GLWNFR (295) |

LAMB1

Several candidate proteases may be responsible for the digestion of LAMB1 in fibrotic tissue. We have through a range of in vitro cleavages of pure native proteins determined that enzymes cleave LAMB1 at least at the cleavage sites at each end of the following sequences or at the cleavage sites marked '.':

TABLE 44

Cleavage sites of LAMB1

| Protease | Cleavage sites marked '.' |
|---|---|
| MMP9 | 209'ALDPAFKIED.'218 |
| MMP2/9 | 1629'.SIESETAASE'1638 |
| MMP2/9 | 1639'ETLFNASQRI.'1648 |

Accordingly, in a method of the invention, said peptide fragments preferably comprise a neo-epitope formed by cleavage of LAMB1 by a protease at an N- or C-terminal site, in any one of the partial sequences of LAMB1 in Table 44.

The immunological binding partner may be one specifically reactive with a C-terminal or N-terminal neo-epitope formed by cleavage of LAMB1.

Suitable immunological binding partners may therefore be specifically reactive with the following sequence at the N terminal of a peptide:

TABLE 45

N-terminal sequence of protease generated peptide fragment of LAMB1.
Cleavage site marked '.'/SEQ ID NO ( )

| .SIESET | (296) |
|---|---| or with either of the following sequence at the C-terminal of a peptide:

TABLE 46

C-terminal sequences of protease generated peptide fragments of LAMB1.
Cleavage sites marked '.'/SEQ ID NO ( )

| AFKIED. | (297) |
|---|---|
| NASQRI. | (298) |

LAMA5

Several candidate proteases may be responsible for the digestion of LAMA5 in fibrotic tissue. We have through a range of in vitro cleavages of pure native proteins determined that enzymes cleave LAMA5 at least at the cleavage sites at each end of the following sequences or at the cleavage sites marked '.':

TABLE 47

Cleavage sites of LAMA5

| Protease | Cleavage sites marked '.' |
|---|---|
| MMP9 | 2402'.NSRNQERLEE'2411 |
| MMP2/9 | 2901'EMDTLNEEVV.'2910 |
| MMP9 | 3056'DLELADAYYL.'3065 |

Accordingly, in a method of the invention, said peptide fragments preferably comprise a neo-epitope formed by cleavage of LAMA5 by a protease at an N- or C-terminal site, or where indicated a site marked by the sign '.' in any one of the partial sequences of LAMA5 in Table 24.

The immunological binding partner may be one specifically reactive with a C-terminal or N-terminal neo-epitope formed by cleavage of LAMA5.

Suitable immunological binding partners may therefore be specifically reactive with the following sequences at the N terminal of a peptide:

TABLE 48

N-terminal sequence of protease generated peptide fragment of LAMA5.
Cleavage sites marked '.'/SEQ ID NO ( )

| .NSRNQE | (299) |
|---|---| or with either of the following sequences at the C-terminal of a peptide:

TABLE 49

C-terminal sequences of protease generated peptide fragments of LAMA5.
Cleavage sites marked '.'/SEQ ID NO ( )

| LNEEVV. | (300) |
|---|---|
| ADAYYL. | (301) |

Further cleavage sites defining neo-epitopes that may be assayed in a similar manner can be identified by exposing collagens, elastin, CRP and proteoglycans or other tissue proteins referred to above to any of the enzymes described herein and isolating and sequencing peptides thereby produced. Furthermore, assays may be based on the neo-epitopes generated adjacent the illustrated cleavage sites, i.e. in the C-terminal sequences that lead up to the N-terminal epitopes given above and the N-terminal sequences that connect to the C-terminal epitopes described.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be (1) a synthetic peptide derived from the sequence of collagen type I, III, IV, V, or VI, or from CRP, or from any of the proteoglycans versican, lumican, decorin and biglycan peptide, ApoE, lumican, LAMC1, LAMB1, or LAMA5 or a competition agent derived from (2) a purified native protein named above cleaved by proteases to reveal said neo-epitope.

One suitable method could be a competition immunoassay using monoclonal antibodies or antibody binding fragments binding to neo-epitopes of an above named protein. Appropriately selected synthetic peptides coated onto the solid surface of a microtitre plate could compete with the sample for binding to the monoclonal antibodies or binding fragments. Alternatively, purified, native protein fragments carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin.

The sample may be a sample of serum, blood, or plasma or an other type, e.g. fibrotic tissue biopsy.

Assays may be conducted as sandwich assays using a first immunological binding partner specifically reactive with a said neo-epitope and a second immunological binding partner reactive with the relevant protein to which the neo-epitope belongs. Optionally, said second immunological binding partner is directed to a second neo-epitope of the same protein.

In certain preferred methods the method further comprises comparing the determined level of said binding of said peptide fragments with values characteristic of (a) comparable healthy individuals and/or (b) a pathological condition and optionally associating a higher level of the measured peptide (normally indicated by a higher level of binding) with a more severe degree of a said condition. Said condition may be a fibrotic condition or may be an inflammatory condition.

An aspect of the present invention relates to the development of monoclonal antibodies recognising neo-epitopes as described above. This can be achieved by immunising mice with synthetic peptides originating from the amino acid sequence of molecules of a named protein (including the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-prolongated form of the immunising peptide (for a C-terminal neo-epitope) or an N-terminal prolongated form of the immunising peptide (for an N-terminal neo-epitope). Antibodies for neo-epitopes may also be evaluated to establish a lack of binding capacity to native protein. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of the relevant protein by a protease at a end-site in any one of the partial sequences set out above, and may be for instance a monoclonal antibody or a binding fragment thereof.

The invention includes a cell line producing a monoclonal antibody against a C-terminal or N-terminal neo-epitope formed by cleavage of a relevant protein at the end-sites of sequences in any one of the partial sequences set out above.

The invention further provides a peptide comprising a C-terminal or N-terminal neo-epitope formed by cleavage of a relevant protein in any one of the partial sequences of these proteins set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of a relevant protein in any one of the partial sequences set out above.

The invention further comprises a vector comprising a nucleic acid sequence comprising an expression signal and a coding sequence which codes for the expression of a peptide comprising a C-terminal or N-terminal neo-epitope formed by cleavage of a relevant protein in any one of the partial sequences set out above and further includes a host cell transformed with such a vector and expressing a said peptide.

Yet another aspect of the invention relates to kits, which can be used conveniently for carrying out the methods described above. Such kits may include (1) a microtitre plate coated with synthetic peptide; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native protein fragments; (2) a monoclonal antibody recognising a neo-epitope on the relevant fragments and reactive with said purified protein fragments; and (3) a labelled anti-mouse IgG immunoglobulin. Alternatively, such kits may include (1) a microtitre plate coated with streptavidin; (2) a synthetic peptide linked to biotin; (3) a monoclonal antibody recognising a neo-epitope on protein fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin; (3) a monoclonal antibody recognising a neo-epitope on relevant protein fragments (and reactive with said synthetic peptide) and conjugated to horseradish peroxidase.

Thus, the invention includes an immunoassay kit comprising an immunological binding partner as described herein and a competition agent which binds said immunological binding partner, and optionally one or more of a wash reagent, a buffer, a stopping reagent, an enzyme label, an enzyme label substrate, calibration standards, an anti-mouse antibody and instructions.

The assays described herein are useful in the diagnosis of fibrosis or inflammatory conditions in patients. In addition, the tests are useful for the assessment of disease progression, and the monitoring of response to therapy. The immunological binding partners of the invention may also be used in immunostaining to show the presence or location of the disclosed protein cleavage products.

Example 1

Identification of Type V Collagen Fragments by Enzyme Cleavage

Reagents

All reagents used for the experiments were standard high-quality chemicals from companies such as Merck (Whitehouse Station, N.J., USA) and Sigma Aldrich (St. Louis, Mo., USA). The synthetic peptides used for monoclonal antibody production were purchased from the Chinese Peptide Company, Beijing, China.

In Vitro Cleavage

Purified type V collagen from human placenta (cat. no. ab7537, Abcam, Cambridge, UK) was cleaved with pro-MMP-2 or pro-MMP-9 (cat. no. 444213; 444231; Calbiochem, Merck, Whitehouse Station, N.J., USA). Fifty µg MMP-2 or MMP-9 was activated with 20 µl 1 mM 4-aminophenylmercuric acetate (APMA) in dimethyl sulfoxide and incubated at 37° C. for 3 hours. Type V collagen was delivered dissolved in 0.5M acetic acid. To facilitate MMP cleavage, the protein was dialyzed for two days to remove the acetic acid. The liquid was filtered to remove proteins below 10 kDa (Microcon Ultracel YM-10, cat. no. 42407, Millipore, Billerica, Mass., USA). Each MMP cleavage was performed separately by mixing 100 µg type V collagen and 1 µg of either MMP-2 or MMP-9 in MMP buffer (100 mM Tris-HCl, 100 mM NaCl, 10 mM $CaCl_2$, 2 mM Zn acetate, pH 8.0). As control, 100 µg of collagen was mixed with MMP buffer alone. The solutions were incubated for 2 hours at 37° C. The cleavage reaction was stopped using 50 µM ethylenediaminetetraacetic acid (EDTA) to a final concentration of 1 µM. Cleavage was verified by visualization using the SilverXpress® Silver Staining Kit (cat. no. LC6100, Invitrogen, Carlsbad, Calif., USA) according to the manufacturer's instructions.

Peptide Identification

Peptide fragments in the in vitro cleaved samples were identified using liquid chromatography (LC) coupled to electrospray ionization (ESI) tandem mass spectrometry (LC-MS/MS). LC-MS samples were ultra-filtrated to remove proteins above 10 kDa, the pH was adjusted to 2.0 using formic acid, and a 4 µL sample was analyzed by LC-MS/MS. LC was performed on a nanoACQUITY HPLC BEH $C_{18}$ column (Waters, Milford, Mass., USA) using a formic acid/acetonitrile gradient. MS and MS/MS were performed on a Synapt High Definition Mass Spectrometry quadruple time of flight MS (QUAD-TOF; Waters, Milford, Mass., USA), with an acquisition range of 350-1600 m/z in MS and 50-2000 m/z, in MS/MS. The software "ProteinLynx Global SERVER (PLGS)" (Waters, Milford, Mass., USA) was used to analyze spectra and generate peak lists. To identify peptide, MS and MS/MS data was searched against a type V collagen (FASTA) protein database using the Mascot 2.2 (Matrix Science, Boston, Mass., USA) software with the ESI-QUAD-TOF settings and carbamidomethyl (C), oxidation of methionine (M), oxidation of lysine (K) and oxidation of proline (P) as variable modifications.

The six amino acids in the N- or C-terminal of the peptides identified by MS were regarded as a neo-epitope generated by the protease in question. All protease-generated sequences were analyzed for homology and distance to other cleavage sites and tested for homology using NPS@: network protein sequence analysis (Combet C, Blanchet C, Geourjon C, Deleage G. NPS@:network protein sequence analysis. Trends Biochem Sci 2000; 25: 147-50).

Example 2

Development of an ELISA Assay for Identified Fragments

Peptide Conjugation

The peptide conjugation was performed using the Maleidide Activated Immunogen Conjugation Kit (Sigma-Aldrich, Mo., USA). Briefly, the cysteine-containing immunogenic neo-epitope (HMGREGREGE-GGC, 400 µl peptide at 5 mg/ml) with one free sulfhydryl (—SH) group was mixed in conjugation buffer with the maleimide-activated ovalbumin (OVA) (180 µl OVA at 10 mg/ml) as a carrier protein with an available maleimide group that could react with sulfhydryl-containing peptides and incubated for 2 hours at room temperature. Conjugated products were cleared of EDTA and sodium azide by desalting or dialysis for two days. For the biotin-conjugated peptides, the biotin-conjugated lysine was added in the solid-phase peptide synthesis procedure.

Monoclonal Antibody Development 4-6 weeks-old Balb/C mice were immunized subcutaneously with about 200 µl emulsified antigen and 50 µg of the neo-epitope CO5-MMP (HMGREGREGE-GGC-OVA). Consecutive immunizations were performed at 2-week intervals until stable sera titer levels were reached in Freund's incomplete adjuvant. Blood samples were collected from the $2^{nd}$ immunization. At each blood sampling, the serum titer was determined and the mouse with highest anti-serum titer was selected for fusion. After the $4^{th}$ immunization, this mouse was rested for 1 month and then boosted intravenously with 50 µg CO5-MMP in 100 µl 0.9% sodium chloride solution three days before isolation of the spleen for cell fusion.

Fusion and Antibody Screening

The fusion procedure performed as described by Gefter et al[132]. Briefly, mouse spleen cells were fused with SP2/0 myeloma fusion partner cells. The hybridoma cells were cloned using a semi-solid medium method and transferred into 96-well microtiter plates for further growth and incubated in a $CO_2$-incubater. Standard limited dilution was used to promote monoclonal growth. Supernatants were screened using an indirect ELISA with streptavidin-coated microtitre plates and HMGREGREGE-K-Biotin as a capture peptide.

Characterization of Clones

Native reactivity and peptide binding of the monoclonal antibodies was evaluated by displacement of native samples (human/rat/mouse serum, plasma and urine) in a preliminary ELISA using 10 ng/mL biotinylated peptide coater on a streptavidin-coated microtitre plate and the supernatant from the growing monoclonal hybridoma. Specificities of the clones to a free peptide (HMGREGREGE), a non-sense peptide, and an elongated peptide (GHMGREGREG) were tested. Isotyping of the monoclonal antibodies was performed using the Clonotyping System-HRP kit, cat. no. 5300-05 (Southern Biotech, Birmingham, Ala., USA). The selected clones were purified using protein G columns according to manufacturer's instructions (GE Healthcare Life Science, Little Chalfont, Buckinghamshire, UK). Selected monoclonal antibodies were labeled with horseradish peroxidase (HRP) using the Lightning link HRP labeling kit according to the instructions of the manufacturer (Innovabioscience, Babraham, Cambridge, UK).

CO5-MMP ELISA Methodology

In preliminary experiments, we optimized the reagents, their concentrations and the incubation periods by performing several checkerboard analyses. The CO5-MMP ELISA was developed as follows: A 96-well streptavidin plate was coated with 5 ng/mL biotinylated synthetic peptide HMGREGREGE-K-Biotin dissolved in assay buffer (25 mM Tris, 1% BSA, 0.1% Tween-20, pH 7.4) and incubated 30 minutes at 20° C. by constant shaking at 300 rpm. Twenty µl of peptide calibrator or sample dissolved in assay buffer were added to appropriate wells, followed by 100 µL of conjugated monoclonal antibody (125 ng/mL) and incubated 1 hour at 4° C. by constant shaking at 300 rpm. Finally, 100 µL tetramethylbenzinidine (TMB) (Kem-En-Tec cat. no. 4380H) was added and the plate was incubated 15 minutes at 20° C. in the dark and shaking at 300 rpm. After each incubation step the plate was washed five times in washing buffer (20 mM Tris, 50 mM NaCl, pH 7.2). The TMB reaction was stopped by adding 100 µl stopping solution (1% HCL) and measured spectrophotometrically at 450 nm with 650 nm as the reference. A standard curve was performed by serial dilution of the CO5-MMP peptide (HMGREGREGE) and plotted using a 4-parametric mathematical fit model. Standard concentrations were 0, 15.625, 31.25, 62.5, 125, 250, 500, 1000 ng/mL.

Technical Evaluation

From 2-fold dilutions of pooled serum samples, linearity was calculated as a percentage of recovery of the 100% sample. The lower detection limit (LDL) was calculated from 21 determinations of the lowest standard (the zero standard) and calculated as the mean+3× standard deviation. The inter- and intra-assay variation was determined by 10 independent runs of 5° C. samples, with each run consisting of two replicas of double determinations of the samples. Finally, for each assay, a master calibrator prepared from synthetic peptides accurately quantified by amino acid analysis was used for calibration purposes.

The analyte stability was determined for three human serum samples for 10 freeze and thaw cycles.

Example 3

ELISA Characterization

The developed CO5-MMP ELISA was evaluated using 20 µl of the samples: intact type V collagen, type V collagen cleaved with MMP-2, type V collagen cleaved with MMP-9, type V collagen cleaved with MMP-13, and an elongated CO5-MMP amino acid sequence (<u>G</u>HMGREGREG). Cross reactivity was tested using in vitro cleaved collagen type I.

Results are shown in FIG. 1, panels A and B, showing percent inhibition of the signal of: A) Free-peptide (HMGREGREGE), Intact type V collagen, MMP-9 cleaved type V collagen, MMP-2 cleaved type V collagen; B) Free-peptide (HMGREGREGE), MMP-13 cleaved type V collagen, MMP-9 cleaved type I collagen, elongated peptide (<u>G</u>HMGREGREG). It can be seen in panel A that the antibody is not substantially reactive with intact collagen type V but is reactive with cleaved collagen type V, and in panel B that the antibody is not reactive with the N-terminal extended peptide. The antibody is thus shown to be specifically reactive with the N-terminal neo-epitope produced by enzyme cleavage.

Example 4

Clinical Utility

Healthy Subjects and AS Patients

The biochemical markers were assessed in serum from patients diagnosed with Ankylosing Spondylitis (AS, according to the modified New York criteria) and compared to sex and age matched non-diseased serum samples from the Department of Medicine 3 of the University of Erlangen-Nuremberg. The non-disease group consisted of 21 healthy females and 19 healthy males with a mean age of 43.0 years, range 18 to 66. The AS group consisted of 19 females and 21 males with a mean age of 42.5 years, range 29 to 63 years.

Statistics

The serum levels of CO5-MMP between the two groups were measured using the ELISA (results shown in FIG. 2) and compared using two-sided non-parametric Mann-Whitney test. In FIG. 2, bars indicate mean levels±standard error of the mean (SEM). Area under the curve was measured on ROC. Odds-ratios was extrapolated from contingency table were all subjects were classified as having low (within 2SD of the mean of the normal population) or high (>SD) levels of the biomarker. Results were considered significant when P<0.05.

These results strongly suggest that the measured neo-epitope of collagen Type V is a valuable marker for AS.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCE LIST

1. World Health Organization. Reducing Risks, Promoting Healthy Life. Peducing Risks, Promoting Healthy Life, Geneva: WHO, 2002:1-230.
2. Wynn T A. Cellular and molecular mechanisms of fibrosis. J Pathol 2008; 214:199-210.
3. Friedman S L. Mechanisms of disease: Mechanisms of hepatic fibrosis and therapeutic implications. Nat Clin Pract Gastroenterol Hepatol 2004; 1:98-105.
4. Tomasek J J, Gabbiani G, Hinz B, Chaponnier C, Brown R. Myofibroblasts and mechano-regulation of connective tissue remodelling. Nat Rev Mol Cell Biol 2002; 3:349-363.
5. Wynn T A. Common and unique mechanisms regulate fibrosis in various fibroproliferative diseases. J Clin Invest 2007; 117:524-529.
6. Marcellin P, Asselah T, Boyer N. Fibrosis and disease progression in hepatitis C. Hepatology 2002; 36:S47-S56.
7. Gagliano N, Arosio B, Grizzi F, Masson S, Tagliabue J, Dioguardi N, Vergani C, Annoni G. Reduced collagenolytic activity of matrix metalloproteinases and development of liver fibrosis in the aging rat. Mech Ageing Dev 2002; 123:413-425.
8. Laurent G J. Dynamic state of collagen: pathways of collagen degradation in vivo and their possible role in regulation of collagen mass. Am J Physiol 1987; 252:C1-C9.
9. Mays P K, McAnulty R J, Campa J S, Laurent G J. Age-related changes in collagen synthesis and degradation in rat tissues. Importance of degradation of newly synthesized collagen in regulating collagen production. Biochem J 1991; 276 (Pt 2):307-313.
10. Garrone R, Lethias C, Le Guellec D. Distribution of minor collagens during skin development. Microsc Res Tech 1997; 38:407-412.
11. Gelse K, Poschl E, Aigner T. Collagens—structure, function, and biosynthesis. Adv Drug Deliv Rev 2003; 55:1531-1546.
12. Phan S H, Thrall R S. Pulmonary Fibrosis. Lung Biology in Health and Disease. 80 ed. New York: Marcel Dekker, Inc., 1995.
13. Martinez-Hernandez A, Amenta P S. The hepatic extracellular matrix. II. Ontogenesis, regeneration and cirrhosis. Virchows Arch A Pathol Anat Histopathol 1993; 423:77-84.
14. Gilliam A. Scleroderma. Curr Dir Autoimmun 2008; 10:258-279.

15. Gressner A M, Weiskirchen R. Modern pathogenetic concepts of liver fibrosis suggest stellate cells and TGF-beta as major players and therapeutic targets. J Cell Mol Med 2006; 10:76-99.
16. Heinegard D, Oldberg A. Structure and biology of cartilage and bone matrix noncollagenous macromolecules. FASEB J 1989; 3:2042-2051.
17. Svensson L, Oldberg A, Heinegard D. Collagen binding proteins. Osteoarthritis and Cartilage 2001; 9:S23-S28.
18. Kiani C, Chen L, Wu Y J, Yee A J, Yang B B. Structure and function of aggrecan. Cell Res 2002; 12:19-32.
19. Krusius T, Gehlsen K R, Ruoslahti E. A fibroblast chondroitin sulfate proteoglycan core protein contains lectin-like and growth factor-like sequences. J Biol Chem 1987; 262:13120-13125.
20. Yang B L, Zhang Y, Cao L, Yang B B. Cell adhesion and proliferation mediated through the G1 domain of versican. J Cell Biochem 1999; 72:210-220.
21. Rauch U, Karthikeyan L, Maurel P, Margolis R U, Margolis R K. Cloning and primary structure of neurocan, a developmentally regulated, aggregating chondroitin sulfate proteoglycan of brain. J Biol Chem 1992; 267:19536-19547.
22. Yamada H, Watanabe K, Shimonaka M, Yamaguchi Y. Molecular cloning of brevican, a novel brain proteoglycan of the aggrecan/versican family. J Biol Chem 1994; 269: 10119-10126.
23. Blochberger T C, Cornuet P K, Hassell J R. Isolation and partial characterization of lumican and decorin from adult chicken corneas. A keratan sulfate-containing isoform of decorin is developmentally regulated. J Biol Chem 1992; 267:20613-20619.
24. Fisher L W, Termine J D, Young M F. Deduced protein sequence of bone small proteoglycan I (biglycan) shows homology with proteoglycan II (decorin) and several non-connective tissue proteins in a variety of species. J Biol Chem 1989; 264:4571-4576.
25. Toyama-Sorimachi N, Sorimachi H, Tobita Y, Kitamura F, Yagita H, Suzuki K, Miyasaka M. A novel ligand for CD44 is serglycin, a hematopoietic cell lineage-specific proteoglycan. Possible involvement in lymphoid cell adherence and activation. J Biol Chem 1995; 270:7437-7444.
26. Bartlett A H, Hayashida K, Park P W. Molecular and cellular mechanisms of syndecans in tissue injury and inflammation. Mol Cells 2007; 24:153-166.
27. Lopez-Casillas F, Wrana J L, Massague J. Betaglycan presents ligand to the TGF beta signaling receptor. Cell 1993; 73:1435-1444.
28. Olsen B R. Life without perlecan has its problems. J Cell Biol 1999; 147:909-912.
29. Gabay C, Kushner I. Acute-phase proteins and other systemic responses to inflammation. N Engl J Med 1999; 340:448-454.
30. Benyon R C, Arthur M J. Extracellular matrix degradation and the role of hepatic stellate cells. Semin Liver Dis 2001; 21:373-384.
31. Guo J, Friedman S L. Hepatic fibrogenesis. Semin Liver Dis 2007; 27:413-426.
32. Iredale J P, Benyon R C, Arthur M J, Ferris W F, Alcolado R, Winwood P J, Clark N, Murphy G. Tissue inhibitor of metalloproteinase-1 messenger RNA expression is enhanced relative to interstitial collagenase messenger RNA in experimental liver injury and fibrosis. Hepatology 1996; 24:176-184.
33. Lee K N, Jackson K W, Christiansen V J, Lee C S, Chun J G, McKee P A. Antiplasmin-cleaving enzyme is a soluble form of fibroblast activation protein. Blood 2006; 107: 1397-1404.
34. Acharya P S, Zukas A, Chandan V, Katzenstein A L, Pure E. Fibroblast activation protein: a serine protease expressed at the remodeling interface in idiopathic pulmonary fibrosis. Hum Pathol 2006; 37:352-360.
35. Levy M T, McCaughan G W, Marinos G, Gorrell M D. Intrahepatic expression of the hepatic stellate cell marker fibroblast activation protein correlates with the degree of fibrosis in hepatitis C virus infection. Liver 2002; 22:93-101.
36. Meyer O. Prognostic markers for systemic sclerosis. Joint Bone Spine 2006; 73:490-494.
37. Hummers L K. Microvascular damage in systemic sclerosis: detection and monitoring with biomarkers. Curr Rheumatol Rep 2006; 8:131-137.
38. McHugh N J, Distler O, Giacomelli R, Riemekasten G. Non organ based laboratory markers in systemic sclerosis. Clin Exp Rheumatol 2003; 21:532-S38.
39. Muller-Quernheim J. Serum markers for the staging of disease activity of sarcoidosis and other interstitial lung diseases of unknown etiology. Sarcoidosis Vasc Diffuse Lung Dis 1998; 15:22-37.
40. Gressner O A, Weiskirchen R, Gressner A M. Biomarkers of liver fibrosis: clinical translation of molecular pathogenesis or based on liver-dependent malfunction tests. Clin Chim Acta 2007; 381:107-113.
41. Gressner O A, Weiskirchen R, Gressner A M. Biomarkers of hepatic fibrosis, fibrogenesis and genetic pre-disposition pending between fiction and reality. J Cell Mol Med 2007; 11:1031-1051.
42. Mariat C. [Diagnosis and follow-up of chronic kidney graft dysfunction: from DFG to new biomarkers]. Nephrol Ther 2008; 4 Suppl 3:S204-S207.
43. Yoneda M, Mawatari H, Fujita K, Iida H, Yonemitsu K, Kato S, Takahashi H, Kirikoshi H, Inamori M, Nozaki Y, Abe Y, Kubota K, Saito S, Iwasaki T, Terauchi Y, Togo S, Maeyama S, Nakajima A. High-sensitivity C-reactive protein is an independent clinical feature of nonalcoholic steatohepatitis (NASH) and also of the severity of fibrosis in NASH. J Gastroenterol 2007; 42:573-582.
44. Wong V S, Hughes V, Trull A, Wight D G, Petrik J, Alexander G J. Serum hyaluronic acid is a useful marker of liver fibrosis in chronic hepatitis C virus infection. J Viral Hepat 1998; 5:187-192.
45. Parise E R, Oliveira A C, Figueiredo-Mendes C, Lanzoni V, Martins J, Nader H, Ferraz M L. Noninvasive serum markers in the diagnosis of structural liver damage in chronic hepatitis C virus infection. Liver Int 2006; 26:1095-1099.
46. McHutchison J G, Blatt L M, de Medina M, Craig J R, Conrad A, Schiff E R, Tong M J. Measurement of serum hyaluronic acid in patients with chronic hepatitis C and its relationship to liver histology. Consensus Interferon Study Group. J Gastroenterol Hepatol 2000; 15:945-951.
47. Camacho V R, Silveira T R, Oliveira J R, Barros S G, Cerski C T. Relationship between serum concetrations of type III procollagen, hyluronic acid and histopathological findings in the liver of HCV-positive blood donors. Arq Gastroenterol 2007; 44:118-122.
48. Lorenzo-Zuniga V, Bartoli R, Masnou H, Montoliu S, Morillas R M, Planas R. Serum concentrations of insulin-like growth factor-I (igf-I) as a marker of liver fibrosis in patients with chronic hepatitis C. Dig Dis Sci 2007; 52:3245-3250.

49. Manolakopoulos S, Bethanis S, Liapi C, Stripeli F, Sklavos P, Margeli A, Christidou A, Katsanika A, Vogiatzakis E, Tzourmakliotis D, Theocharis S. An assessment of serum leptin levels in patients with chronic viral hepatitis: a prospective study. BMC Gastroenterol 2007; 7:17.

50. Camacho V R, Silveira T R, Oliveira J R, Barros S G, Cerski C T. Relationship between serum concetrations of type III procollagen, hyluronic acid and histopathological findings in the liver of HCV-positive blood donors. Arq Gastroenterol 2007; 44:118-122.

51. Leroy V, Hilleret M N, Sturm N, Trocme C, Renversez J C, Faure P, Morel F, Zarski J P. Prospective comparison of six non-invasive scores for the diagnosis of liver fibrosis in chronic hepatitis C. J Hepatol 2007; 46:775-782.

52. Trocme C, Leroy V, Sturm N, Hilleret M N, Bottari S, Morel F, Zarski J P. Longitudinal evaluation of a fibrosis index combining MMP-1 and PIIINP compared with MMP-9, TIMP-1 and hyaluronic acid in patients with chronic hepatitis C treated by interferon-alpha and ribavirin. J Viral Hepat 2006; 13:643-651.

53. Zheng M, Cai W M, Weng H L, Liu R H. ROC curves in evaluation of serum fibrosis indices for hepatic fibrosis. World J Gastroenterol 2002; 8:1073-1076.

54. Lebensztejn D M, Sobaniec-Lotowska M E, Bauer M, Kaczmarski M, Voelker M, Schuppan D. Serum fibrosis markers as predictors of an antifibrotic effect of interferon alfa in children with chronic hepatitis B. Eur J Gastroenterol Hepatol 2005; 17:843-848.

55. Lebensztejn D M, Sobaniec-Lotowska M E, Kaczmarski M, Voelker M, Schuppan D. Matrix-derived serum markers in monitoring liver fibrosis in children with chronic hepatitis B treated with interferon alpha. World J Gastroenterol 2006; 12:3338-3343.

56. Tsochatzis E, Papatheodoridis G V, Hadziyannis E, Georgiou A, Kafiri G, Tiniakos D G, Manesis E K, Archimandritis A J. Serum adipokine levels in chronic liver diseases: association of resistin levels with fibrosis severity. Scand J Gastroenterol 2008; 43:1128-1136.

57. Patel K, Gordon S C, Jacobson I, Hezode C, Oh E, Smith K M, Pawlotsky J M, McHutchison J G. Evaluation of a panel of non-invasive serum markers to differentiate mild from moderate-to-advanced liver fibrosis in chronic hepatitis C patients. J Hepatol 2004; 41:935-942.

58. Lieber C S, Weiss D G, Paronetto F. Value of fibrosis markers for staging liver fibrosis in patients with precirrhotic alcoholic liver disease. Alcohol Clin Exp Res 2008; 32:1031-1039.

59. Forns X, Ampurdanes S, Llovet J M, Aponte J, Quinto L, Martinez-Bauer E, Bruguera M, Sanchez-Tapias J M, Rodes J. Identification of chronic hepatitis C patients without hepatic fibrosis by a simple predictive model. Hepatology 2002; 36:986-992.

60. Bourliere M, Penaranda G, Renou C, Botta-Fridlund D, Tran A, Portal I, Lecomte L, Castellani P, Rosenthal-Allieri M A, Gerolami R, Ouzan D, Deydier R, Degott C, Halfon P. Validation and comparison of indexes for fibrosis and cirrhosis prediction in chronic hepatitis C patients: proposal for a pragmatic approach classification without liver biopsies. J Viral Hepat 2006; 13:659-670.

61. Cacoub P, Carrat F, Bedossa P, Lambert J, Penaranda G, Perronne C, Pol S, Halfon P. Comparison of non-invasive liver fibrosis biomarkers in HIV/HCV co-infected patients: the fibrovic study—ANRS HC02. J Hepatol 2008; 48:765-773.

62. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.

63. Grigorescu M, Rusu M, Neculoiu D, Radu C, Serban A, Catanas M, Grigorescu M D. The FibroTest value in discriminating between insignificant and significant fibrosis in chronic hepatitis C patients. The Romanian experience. J Gastrointestin Liver Dis 2007; 16:31-37.

64. Halfon P. Bacq Y, De M A, Penaranda G, Bourliere M, Ouzan D, Tran A, Botta D, Renou C, Brechot M C, Degott C, Paradis V. Comparison of test performance profile for blood tests of liver fibrosis in chronic hepatitis C. J Hepatol 2007; 46:395-402.

65. Halfon P, Bourliere M, Deydier R, Botta-Fridlund D, Renou C, Tran A, Portal I, Allemand I, Bertrand J J, Rosenthal-Allieri A, Rotily M, Sattonet C, Benderitter T, Saint Paul M C, Bonnot H P, Penaranda G, Degott C, Masseyeff M F, Ouzan D. Independent prospective multicenter validation of biochemical markers (fibrotest-actitest) for the prediction of liver fibrosis and activity in patients with chronic hepatitis C: the fibropaca study. Am J Gastroenterol 2006; 101:547-555.

66. Leroy V, Halfon P, Bacq Y, Boursier J, Rousselet M C, Bourliere M, De M A, Sturm N, Hunault G, Penaranda G, Brechot M C, Trocme C, Cales P. Diagnostic accuracy, reproducibility and robustness of fibrosis blood tests in chronic hepatitis C: a meta-analysis with individual data. Clin Biochem 2008; 41:1368-1376.

67. Ratziu V, Massard J, Charlotte F, Messous D, Imbert-Bismut F, Bonyhay L, Tahiri M, Munteanu M, Thabut D, Cadranel J F, Le B B, de L, V, Poynard T. Diagnostic value of biochemical markers (FibroTest-FibroSURE) for the prediction of liver fibrosis in patients with non-alcoholic fatty liver disease. BMC Gastroenterol 2006; 6:6.

68. Poynard T, Imbert-Bismut F, Ratziu V, Chevret S, Jardel C, Moussalli J, Messous D, Degos F. Biochemical markers of liver fibrosis in patients infected by hepatitis C virus: longitudinal validation in a randomized trial. J Viral Hepat 2002; 9:128-133.

69. Poynard T, Munteanu M, Imbert-Bismut F, Charlotte F, Thabut D, Le C S, Messous D, Thibault V, Benhamou Y, Moussalli J, Ratziu V. Prospective analysis of discordant results between biochemical markers and biopsy in patients with chronic hepatitis C. Clin Chem 2004; 50:1344-1355.

70. Poynard T, Morra R, Halfon P, Castera L, Ratziu V, Imbert-Bismut F, Naveau S, Thabut D, Lebrec D, Zoulim F, Bourliere M, Cacoub P, Messous D, Munteanu M, de L, V. Meta-analyses of FibroTest diagnostic value in chronic liver disease. BMC Gastroenterol 2007; 7:40.

71. Ngo Y, Munteanu M, Messous D, Charlotte F, Imbert-Bismut F, Thabut D, Lebray P, Thibault V, Benhamou Y, Moussalli J, Ratziu V, Poynard T. A prospective analysis of the prognostic value of biomarkers (FibroTest) in patients with chronic hepatitis C. Clin Chem 2006; 52:1887-1896.

72. Naveau S, Raynard B, Ratziu V, Abella A, Imbert-Bismut F, Messous D, Beuzen F, Capron F, Thabut D, Munteanu M, Chaput J C, Poynard T. Biomarkers for the prediction of liver fibrosis in patients with chronic alcoholic liver disease. Clin Gastroenterol Hepatol 2005; 3:167-174.

73. Myers R P, Tainturier M H, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003; 39:222-230.

74. Jacqueminet S, Lebray P, Morra R, Munteanu M, Devers L, Messous D, Bernard M, Hartemann-Heurtier A, Imbert- Bismut F, Ratziu V, Grimaldi A, Poynard T. Screening for liver fibrosis by using a noninvasive biomarker in patients with diabetes. Clin Gastroenterol Hepatol 2008; 6:828-831.
75. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.
76. Poynard T, Zoulim F, Ratziu V, Degos F, Imbert-Bismut F, Deny P, Landais P, El H A, Slama A, Blin P, Thibault V, Parvaz P, Munteanu M, Trepo C. Longitudinal assessment of histology surrogate markers (FibroTest-ActiTest) during lamivudine therapy in patients with chronic hepatitis B infection. Am J Gastroenterol 2005; 100:1970-1980.
77. Poynard T, Munteanu M, Imbert-Bismut F, Charlotte F, Thabut D, Le C S, Messous D, Thibault V, Benhamou Y, Moussalli J, Ratziu V. Prospective analysis of discordant results between biochemical markers and biopsy in patients with chronic hepatitis C. Clin Chem 2004; 50:1344-1355.
78. Myers R P, Tainturier M H, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003; 39:222-230.
79. Carvalho-Filho R J, Schiavon L L, Narciso-Schiavon J L, Sampaio J P, Lanzoni V P, Ferraz M L, Silva A E. Optimized cutoffs improve performance of the aspartate aminotransferase to platelet ratio index for predicting significant liver fibrosis in human immunodeficiency virus/hepatitis C virus co-infection. Liver Int 2008; 28:486-493.
80. Al-Mohri H, Cooper C, Murphy T, Klein M B. Validation of a simple model for predicting liver fibrosis in HIV/hepatitis C virus-coinfected patients. HIV Med 2005; 6:375-378.
81. dales P, Laine F, Boursier J, Deugnier Y, Moal V, Oberti F, Hunault G, Rousselet M C, Hubert I, Laafi J, Ducluzeaux P H, Lunel F. Comparison of blood tests for liver fibrosis specific or not to NAFLD. J Hepatol 2008.
82. Paggi S, Colli A, Fraquelli M, Vigano M, Del P P, Facciotto C, Colombo M, Ronchi G, Conte D. A non-invasive algorithm accurately predicts advanced fibrosis in hepatitis C: a comparison using histology with internal-external validation. J Hepatol 2008; 49:564-571.
83. Trang T, Petersen J R, Snyder N. Non-invasive markers of hepatic fibrosis in patients co-infected with HCV and HIV: comparison of the APRI and FIB-4 index. Clin Chim Acta 2008; 397:51-54.
84. Snyder N, Gajula L, Xiao S Y, Grady J, Luxon B, Lau D T, Soloway R, Petersen J. APRI: an easy and validated predictor of hepatic fibrosis in chronic hepatitis C. J Clin Gastroenterol 2006; 40:535-542.
85. Snyder N, Nguyen A, Gajula L, Soloway R, Xiao S Y, Lau D T, Petersen J. The APRI may be enhanced by the use of the FIBROSpect II in the estimation of fibrosis in chronic hepatitis C. Clin Chim Acta 2007; 381:119-123.
86. Hongbo L, Xiaohui L, Hong K, Wei W, Yong Z. Assessing routine and serum markers of liver fibrosis in CHB patients using parallel and serial interpretation. Clin Biochem 2007; 40:562-566.
87. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.
88. Adams L A, Bulsara M, Rossi E, DeBoer B, Speers D, George J, Kench J, Farrell G, McCaughan G W, Jeffrey G P. Hepascore: an accurate validated predictor of liver fibrosis in chronic hepatitis C infection. Clin Chem 2005; 51:1867-1873.
89. Koda M, Matunaga Y, Kawakami M, Kishimoto Y, Suou T, Murawaki Y. FibroIndex, a practical index for predicting significant fibrosis in patients with chronic hepatitis C. Hepatology 2007; 45:297-306.
90. Metwally M A, Zein C O, Zein N N. Predictors and noninvasive identification of severe liver fibrosis in patients with chronic hepatitis C. Dig Dis Sci 2007; 52:582-588.
91. Mohamadnejad M, Montazeri G, Fazlollahi A, Zamani F, Nasiri J, Nobakht H, Forouzanfar M H, Abedian S, Tavangar S M, Mohamadkhani A, Ghoujeghi F, Estakhri A, Nouri N, Farzadi Z, Najjari A, Malekzadeh R. Noninvasive markers of liver fibrosis and inflammation in chronic hepatitis B-virus related liver disease. Am J Gastroenterol 2006; 101:2537-2545.
92. Zaman A, Rosen H R, Ingram K, Corless C L, Oh E, Smith K. Assessment of FIBROSpect II to detect hepatic fibrosis in chronic hepatitis C patients. Am J Med 2007; 120:280-14.
93. Patel K, Nelson D R, Rockey D C, Afdhal N H, Smith K M, Oh E, Hettinger K, Vallee M, Dev A, Smith-Riggs M, McHutchison J G. Correlation of FIBROSpect II with histologic and morphometric evaluation of liver fibrosis in chronic hepatitis C. Clin Gastroenterol Hepatol 2008; 6:242-247.
94. Sebastiani G, Vario A, Guido M, Noventa F, Plebani M, Pistis R, Ferrari A, Alberti A. Stepwise combination algorithms of non-invasive markers to diagnose significant fibrosis in chronic hepatitis C. J Hepatol 2006; 44:686-693.
95. Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-1075.
96. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.
97. Castera L, Vergniol J, Foucher J, Le B B, Chanteloup E, Haaser M, Darriet M, Couzigou P, de L, V. Prospective comparison of transient elastography, Fibrotest, APRI, and liver biopsy for the assessment of fibrosis in chronic hepatitis C. Gastroenterology 2005; 128:343-350.
98. Guanabens N, Pares A, Alvarez L, Martinez de Osaba M J, Monegal A, Peris P, Ballesta A M, Rodes J. Collagen-related markers of bone turnover reflect the severity of liver fibrosis in patients with primary biliary cirrhosis. J Bone Miner Res 1998; 13:731-738.
99. Moller S, Hansen M, Hillingso J, Jensen J E, Henriksen J H. Elevated carboxy terminal cross linked telopeptide of type I collagen in alcoholic cirrhosis: relation to liver and kidney function and bone metabolism. Gut 1999; 44:417-423.
100. Rosen H N, Parker R A, Greenspan S L, Iloputaife I D, Bookman L, Chapin D, Perlmutter I, Kessel B, Qvist P, Rosenblatt M. Evaluation of ability of biochemical markers of bone turnover to predict a response to increased doses of HRT. Calcif Tissue Int 2004; 74:415-423.

101. Lein M, Wirth M, Miller K, Eickenberg H U, Weissbach L, Schmidt K, Haus U, Stephan C, Meissner S, Loening S A, Jung K. Serial Markers of Bone Turnover in Men with Metastatic Prostate Cancer Treated with Zoledronic Acid for Detection of Bone Metastases Progression. Eur Urol 2007.

102. Attallah A M, Toson E A, Shiha G E, Omran M M, bdel-Aziz M M, El-Dosoky I. Evaluation of serum procollagen aminoterminal propeptide III, laminin, and hydroxyproline as predictors of severe fibrosis in patients with chronic hepatitis C. J Immunoassay Immunochem 2007; 28:199-211.

103. Ulrich D, Noah E M, von H D, Pallua N. TIMP-1, MMP-2, MMP-9, and PIIINP as serum markers for skin fibrosis in patients following severe burn trauma. Plast Reconstr Surg 2003; 111:1423-1431.

104. Farkkila M, Rautiainen H, Karkkainen P, Karvonen A L, Nurmi H, Niemela O. Serological markers for monitoring disease progression in noncirrhotic primary biliary cirrhosis on ursodeoxycholic acid therapy. Liver Int 2008; 28:787-797.

105. Guechot J, Poupon R E, Giral P, Balkau B, Giboudeau J, Poupon R. Relationship between procollagen III aminoterminal propeptide and hyaluronan serum levels and histological fibrosis in primary biliary cirrhosis and chronic viral hepatitis C. J Hepatol 1994; 20:388-393.

106. Klappacher G, Franzen P, Haab D, Mehrabi M, Binder M, Plesch K, Pacher R, Grimm M, Pribill I, Eichler H G., Measuring extracellular matrix turnover in the serum of patients with idiopathic or ischemic dilated cardiomyopathy and impact on diagnosis and prognosis. Am J Cardiol 1995; 75:913-918.

107. Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-1075.

108. Suzuki, K., Enghild, J. J., Morodomi, T., Salvesen, G., and Nagase, H. 1990. Mechanisms of activation of tissue procollagenase by matrix metalloproteinase 3 (stromelysin). Biochemistry 29:10261-10270.

109. Lijnen, H. R. 2001. Plasmin and matrix metalloproteinases in vascular remodeling. Thromb. Haemost. 86:324-333.

110. Tam L S, Cu J, Yu D. Pathogenesis of ankylosing spondylitis. Nat Rev Rheumatol 2010 July; 6(7):399-405.

111. Braun J, Pincus T. Mortality, course of disease and prognosis of patients with ankylosing spondylitis. Clin Exp Rheumatol 2002 November; 20(6 Suppl 28):S16-S22.

112. Kumar VAAKFN. Tissue renewal and repair: regeneration, healing, and fibrosis. Pathologic basis of disease. Philadelphia, Pa., USA: Elsevier Saunders, 2005.87-118.

113. Schuppan D, Ruehl M, Somasundaram R, Hahn E G. Matrix as a modulator of hepatic fibrogenesis. Semin Liver Dis 2001 August; 21(3):351-372.

114. Lochter A, Bissell M J. An odyssey from breast to bone: multi-step control of mammary metastases and osteolysis by matrix metalloproteinases. APMIS 1999 January; 107 (1):128-136.

115. Karsdal M A, Madsen S H, Christiansen C, Henriksen K, Fosang A J, Sondergaard B C. Cartilage degradation is fully reversible in the presence of aggrecanase but not matrix metalloproteinase activity. Arthritis Res Ther 2008; 10(3):R63.

116. Karsdal M A, Henriksen K, Leeming D J, Mitchell P, Duffin K, Barascuk N, et al. Biochemical markers and the FDA Critical Path: how biomarkers may contribute to the understanding of pathophysiology and provide unique and necessary tools for drug development. Biomarkers 2009 May; 14(3):181-202.

117. Bay-Jensen A C, Hoegh-Madsen S, Dam E, Henriksen K, Sondergaard B C, Pastoureau P, et al. Which elements are involved in reversible and irreversible cartilage degradation in osteoarthritis? Rheumatol Int 2010 February; 30(4):435-442.

118. Zhen E Y, Brittain I J, Laska D A, Mitchell P G, Sumer E U, Karsdal M A, et al. Characterization of metalloprotease cleavage products of human articular cartilage. Arthritis Rheum 2008 August; 58(8):2420-2431.

119. Boeker K H, Haberkorn C I, Michels D, Flemming P, Manns M P, Lichtinghagen R. Diagnostic potential of circulating TIMP-1 and MMP-2 as markers of liver fibrosis in patients with chronic hepatitis C. Clin Chim Acta 2002 February; 316(1-2):71-81.

120. Hemmann S, Graf J, Roderfeld M, Roeb E. Expression of MMPs and TIMPs in liver fibrosis—a systematic review with special emphasis on anti-fibrotic strategies. J Hepatol 2007 May; 46(5):955-975.

121. Kirimlioglu H, Kirimlioglu V, Yilmaz S. Expression of matrix metalloproteinases 2 and 9 in donor liver, cirrhotic liver, and acute rejection after human liver transplantation. Transplant Proc 2008 December; 40(10):3574-3577.

122. Schaller S, Henriksen K, Hoegh-Andersen P, Sondergaard B C, Sumer E U, Tanko L B, et al. In vitro, ex vivo, and in vivo methodological approaches for studying therapeutic targets of osteoporosis and degenerative joint diseases: how biomarkers can assist? Assay Drug Dev Technol 2005 October; 3(5):553-580.

123. Wenstrup R J, Florer J B, Brunskill E W, Bell S M, Chervoneva I, Birk D E. Type V collagen controls the initiation of collagen fibril assembly. J Biol Chem 2004 Dec. 17; 279(51):53331-53337.

124. Symoens S, Renard M, Bonod-Bidaud C, Syx D, Vaganay E, Malfait F, et al. Identification of binding partners interacting with the alpha1-N-propeptide of type V collagen. Biochem J 2010 Dec. 22; 433(2):371-381.

125. Berendsen A D, Bronckers A L, Smit T H, Walboomers X F, Everts V. Collagen type V enhances matrix contraction by human periodontal ligament fibroblasts seeded in three-dimensional collagen gels. Matrix Biol 2006 October; 25(8):515-522.

126. Murasawa Y, Hayashi T, Wang P C. The role of type V collagen fibril as an ECM that induces the motility of glomerular endothelial cells. Exp Cell Res 2008 Dec. 10; 314(20):3638-3653.

127. Vassiliadis E, Veidal S S, Simonsen H, Larsen D V, Vainer B, Chen X, et al. Immunological detection of the type V collagen propeptide fragment, PVCP-1230, in connective tissue remodeling associated with liver fibrosis. Biomarkers 2011 May 25.

128. Birk D E, Fitch J M, Babiarz J P, Linsenmayer T F. Collagen type I and type V are present in the same fibril in the avian corneal stroma. J Cell Biol 1988 March; 106(3): 999-1008.

129. Wenstrup R J, Florer J B, Willing M C, Giunta C, Steinmann B, Young F, et al. COL5A1 haploinsufficiency is a common molecular mechanism underlying the classical form of EDS. Am J Hum Genet. 2000 June; 66(6):1766-1776.

130. Schwarze U, Atkinson M, Hoffman G G, Greenspan D S, Byers P H. Null alleles of the COL5A1 gene of type V collagen are a cause of the classical forms of Ehlers-Danlos syndrome (types I and II). Am J Hum Genet. 2000 June; 66(6):1757-1765.

131. Michalickova K, Susic M, Willing M C, Wenstrup R J, Cole W G. Mutations of the alpha2(V) chain of type V collagen impair matrix assembly and produce ehlers-danlos syndrome type I. Hum Mol Genet. 1998 February; 7(2):249-255.

132. Gefter M L, Margulies D H, Scharff M D. A simple method for polyethylene glycol-promoted hybridization of mouse myeloma cells. Somatic Cell Genet. 1977 March; 3(2):231-236.

The invention claimed is:

1. A method of diagnosis or of quantitation of fibrosis comprising:

obtaining a patient biofluid sample, conducting an immunoassay to measure an aggregate amount of N- or C-terminal neo-epitope containing protein fragments naturally present in said biofluid sample, and associating an elevation of said measure in said patient above a normal level with the presence or extent of fibrosis, wherein said immunoassay is conducted by a method comprising;

contacting the N- or C-terminal neo-epitope containing protein fragments, formed by cleavage of an intact protein by a proteinase, that are naturally present in said sample with an immunological binding partner specifically reactive with the N- or C-terminal neo-epitope, but not reactive with the intact protein, and measuring the extent of binding of the N- or C-terminal neo-epitope protein fragments to said immunological binding partner to measure therein protein fragments comprising said neo-epitope, wherein said immunological binding partner is raised against a synthetic peptide corresponding to an N- or C-terminal neo-epitope amino acid sequence formed by cleavage of an intact protein by a proteinase and specifically binds a neo-epitope constituted by said N- or C-terminal amino acid sequence, said N- or C-terminal amino acid being formed by cleavage of said intact protein at any one of the cleavage sites shown in the following table:

| Protease | Collagen Type I<br>Cleavage sites marked '.';<br>SEQ ID NO in ( ) |
|---|---|
| FAP | Q.GAPGLQGMPG.E (1) |
| FAP | D.RGEPGPPGPAGFAGPPGAD.G (2) |
| FAP | D.GVRGLTGPIGPPGPAGAPGD.K (3) |
| FAP | A.GLPGAKGLTGSPGSPGPDGK.T (4) |
| FAP | D.AGPVGPPGPPGPPGPPGPPSAG.F (5) |
| FAP | D.GLNGLPGPIGPPGPRGRTGD.A (6) |
| FAP | S.PGKDGVRGLTGPIGPPGPAGAP.G (7) |
| FAP | L.PGPPGPPGPPGPPGLGGNFAPQ.L (8) |
| FAP | L.PGPPGPPGPPGPPGLGGNFAPQ.L (9) |
| FAP | P.GPPGPPGPPGPPGLGGNFAPQLSY.G (10) |
| FAP | P.GPPGPPGPPGPPGLGGNFAPQL.S (11) |
| FAP | F.PGARGPSGPQGPGGPPGPKGNSG.E (12) |
| FAP | G.LPGPPGPPGPPGPPGLGGNFAPQ.L (13) |
| FAP | G.LPGPPGPPGPPGPPGLGGNFAPQ.L (14) |
| FAP | G.LPGPPGPPGPPGPPGLGGNFAPQ.L (15) |

| Collagen Type I | |
|---|---|
| Protease | Cleavage sites marked '.'; SEQ ID NO in ( ) |
| FAP | D.AGPVGPPGPPGPPGPPGPPGPPSAGFD.F (16) |
| FAP | D.GLNGLPGPIGPPGPRGRTGDAGPVGPPGPPGPPGPPGPPGPPSAG.F (17) |
| FAP | P.GPPGPPGPPGPPGLGGNFAPQLSYGYDEKSTGGISVPGPMGP.S (18) |
| FAP | D.GLNGLPGPIGPPGPRGRTGDAGPVGPPGPPGPPGPPGPPGPPSAGFD.F(19) |
| MMP9 + FAP | D.RGEPGPPGPAGFAGPPGAD.G (20) |
| MMP9 + FAP | D.GVRGLTGPIGPPGPAGAPGD.K (21) |
| MMP9 + FAP | D.AGPVGPPGPPGPPGPPGPPSAG.F (22) |
| MMP9 + FAP | D.GLNGLPGPIGPPGPRGRTGD.A (23) |
| MMP9 + FAP | D.AGPVGPPGPPGPPGPPGPPSAGF.D (24) |
| MMP9 + FAP | L.PGPPGPPGPPGPPGLGGNFAPQ.L (25) |
| MMP9 + FAP | P.GPPGPPGPPGLGGNFAPQLSY.G (26) |
| MMP9 + FAP | P.GPPGPPGPPGPPGLGGNFAPQL.S (27) |
| MMP9 + FAP | G.LPGPPGPPGPPGPPGLGGNFAPQ.L (28) |
| MMP9 + FAP | L.PGPPGPPGPPGPPGLGGNFAPQL.S (29) |
| MMP9 + FAP | P.GPPGPPGPPGPPSAGFDFSFLPQPPQEKAHDGGRYYR.A (30) |
| MMP9 + FAP | D.GLNGLPGPIGPPGPRGRTGDAGPVGPPGPPGPPGPPGPPGPPSAGFD.F (19) |
| MMP9 | G.AAGPPGP.T (31) |
| MMP9 | P.VGPVGARGP.A (32) |
| MMP9 | P.AGPVGPVGARGP.A (33) |
| MMP9 | P.RGLPGPPGAPGP.Q (34) |
| MMP9 | G.EAGRPGEAGLPG.A (35) |
| MMP9 | Q.DGRPGPPGPPGA.R (36) |
| MMP9 | K.DGLNGLPGPIGPPGP.R (37) |
| MMP9 | G.AKGEPGPVGVQGPPGP.A (38) |
| MMP9 | P.AGARGNDGATGAAGPPGP.T (39) |
| MMP9 | P.VGPPGPPGPPGPPGPPSAGF.D (40) |
| MMP9 | A.GAPGKDGLNGLPGPIGPPGP.R (41) |
| MMP9 | D.AGPVGPPGPPGPPGPPGPPSAG.F (42) |
| MMP9 | S.AGAPGKDGLNGLPGPIGPPGP.R (43) |
| MMP9 | G.PPGPPGPPGLGGNFAPQLSYG.Y (44) |
| MMP9 | P.GPPGPPGPPGLGGNFAPQL.S (45) |
| MMP9 | G.LPGPPGPPGPPGPPGLGGNFAPQ.L (46) |
| MMP9 | G.ERGPPGPMGPPGLAGPPGESGREGAPGAEGSPG.R (47) |
| FAP | 853'.IGNVGAPGAK'862 (alpha 2 chain) (48) |
| FAP | 462'.AGKEGPVGLP'471 (alpha 2 chain) (49) |
| FAP | 249'.IGSAGPPGFP'258 (alpha 2 chain) (50) |
| FAP | 1153'.DGLNGLPGPI'1162 (alpha 1 chain) (51) |
| FAP | 1153'.D(β)GLNGLPGPI'1162 (alpha 1 chain) (52) |
| FAP | 751'.KGADGSPGKD'760 (alpha 1 chain) (53) |
| FAP | 171'STGGISVPGP.'180 (alpha 1 chain) (54) |
| FAP | 167'.YDEKSTGGIS'176 (alpha 1 chain) (55) |

| Collagen Type III | |
|---|---|
| Protease | Cleavage sites marked '.' |
| FAP | E.AGIPGVPGAK.G (56) |
| FAP | P.KGDPGPPGIP.G (57) |
| FAP | G.PQGPKGDPGPP.G (58) |
| FAP | G.PGMRGMPGSPGGP.G (59) |
| FAP | D.GPPGPAGNTGAPGSPGVSGPKGD.A (60) |
| FAP | H.AGAQGPPGPPGINGSPGGKGEMGPAGIP.G (61) |
| FAP | D.GPRGPTGPIGPPGPAGQPGD.K (62) |
| MMP9 | D.GPPGPAGNTGAPGSPGVSGPKGD.A (63) |
| MMP9 | P.GSPGPAGQQGAIGSPGPAGPRGP.V (64) |
| MMP9 | G.ERGRPGLP.G (65) |
| MMP9 | G.KGDRGENGSPG.A (66) |
| MMP9 | E.PGKNGAKGEPGP.R (67) |
| MMP9 | S.PGERGETGPPGP.A (68) |
| MMP9 | P.GGPGADGVPGKDGP.R (69) |
| MMP9 | G.PPGKDGTSGHPGP.I (70) |
| MMP9 | R.GLPGPPGIKGPAGIPG.F (71) |
| MMP9 | L.PGENGAPGPMGPRGAPGE.R (72) |
| MMP9 | G.APGAPGGKGDAGAPGERGPP.G (73) |
| MMP9 | A.PGLKGENGLPGENGAPGPMGPRGAPG.E (74) |
| MMP9 | G.IAGITGARGLAGPPGMPGPRGSPGPQ.G (75) |
| MMP9 | G.SPGAKGEVGPAGSPGSNGAPGQRGEPGP.Q (76) |
| MMP9 | G.LKGENGLPGENGAPGPMGPRGAPGERGRPGLPGAA.G (77) |

Collagen Type III

| Protease | Cleavage sites marked '.' |
|---|---|
| MMP9 + FAP | D.GPPGPAGNTGAPGSPGVSGPKGD.A (78) |
| ADAMTS-4 | 267'.GFDGRNGEKG'276 (79) |
| FAP | 533'.PGMRGMPGSP'542 (alpha 1 chain) (80) |
| Unknown | 642'.GLPGTGGPPG'651 (81) |
| Unknown | 652'ENGKPGEPGP.'661 (82) |
| Unknown | 861'.GERGSPGGPG'870 (83) |
| unknown | 899'PGKDGPPGPA.'908 (alpha 1 chain) (84) |
| MMP9, ADAMTS-4 | 442'.GLPGTGGPPG'451 (85) |

Collagen Type IV

| Protease | Cleavage sites marked '.' |
|---|---|
| MMP9 | 333'.IVIGTGPLGE'342 (alpha 1 chain) (86) |
| MMP9 | 328'PGPPGIVIGT.'337 (alpha 1 chain) (87) |

Collagen Type V

| Protease | Cleavage sites marked '.' |
|---|---|
| MMP2 | 920'ERGPRGITGK.'929 (alpha 1 chain) (88) |
| MMP2/9 | 1584'.RRNIDASQLL'1593 (alpha 1 chain) (89) |
| MMP2/9 | 229'.QQGGAGPTGP'238 (alpha 2 chain) (90) |
| MMP2/9 | 355'.QRGAHGMPGK'364 (alpha 2 chain) (91) |
| MMP9 | 525'.RVGKMGRPGA'534 (alpha 3 chain) (92) |
| MMP2/9 | 1317'.HMGREGREGE'1326 (alpha 3 chain) (93) |

Collagen Type VI

| Protease | Cleavage sites marked '.' |
|---|---|
| MMP8 | 873'.RIAVAQYSDD'883 (94) |
| MMP8 | 1192'.QLGTVQQVIS'1202 (95) |
| MMP12 | 1231'.RDVVFLIDGS'1241 (96) |

ApoE

| Protease | Cleavage sites marked '.' |
|---|---|
| MMP9 | 81'.LMDETM'86 (97) |
| Cat K | 246'RLDEVK.'251 (98) |

ApoE

| Protease | Cleavage sites marked '.' |
|---|---|
| MMP9 | 101'TPVAEE.'106 (99) |
| Cat K | 126'.MEEMGS'131 (100) |

Biglycan

| Protease | Cleavage sites marked '.' |
|---|---|
| MMP3 | 219'.KLTGIPKDLP'228 (101) |
| MMP3 | 226'DLPETLNELH.'235 (102) |
| MMP12 | 220'LTGIPKDLPE.'229 (103) |
| MMP13 | 329'.RAYYNGISLF'338 (104) |
| MMP13 | 334'GISLFNNPVP.'343 (105) |
| MMP12 | 87'.EISPDTTLLD'96 (106) |
| MMP12 | 97'LQNNDISELR.'106 (107) |
| MMP9 | 188'.IEMGGNPLENS'198 (108) |
| MMP9 | 200'FEPGAFDGLK.'209 (109) |
| MMP9 | 148'.NHLVEIPPNL'157 (110) |
| MMP9 | 151'VEIPPNLPSS.'160 (111) |
| MMP9 | 232'.NELHLDHNK'240 (112) |
| MMP9 | 344'.YWEVQPATFR'353 (113) |
| MMP9, MMP12 | 241'.IQAIELEDLL'250 (114) |

Decorin

| Protease | Cleavage sites marked '.' |
|---|---|
| ADAM-TS4 | 75'.VPKDLPPDTT'84 (115) |

Versican

| Protease | Cleavage sites marked '.' |
|---|---|
| Cathepsin K | 3247'.YENWRPNQPD'3256 (116) |
| Cathepsin K | 3255'PDSFFSAGED.'3264 (117) |
| Cathepsin K | 3221'.HDYQWIGLN'3229 (118) |
| MMP8 | 3306'.KTFGKMKPRY'3316 (119) |
| MMP8 | 486'.SVTQIEQIEV'495 (120) |
| MMP8 | 491'EQIEVGPLVT.'500 (121) |

| CRP | |
|---|---|
| Protease | Cleavage sites marked '.' |
| Signal peptide | 013'LSHAFG.'018 (122) |
| MMP3/8/9, /Cat S/K | 011'TSLSHA.'016 (123) |

| Elastin | |
|---|---|
| Protease | Cleavage sites marked '.' |
| Signal peptide | 21'LHPSRP.'26 (124) |
| ADAMTS1/4/8 MMP8/9 | 379'KAAKYG.'384 (125) |
| MMP9/12 | 547'GIGPGG.'552 (126) |

| Lumican | |
|---|---|
| Protease | Cleavage sites marked '.' |
| MMP9 | 75'NNQIDHIDEK.'84 (127) |

| LAMC1 | |
|---|---|
| Protease | Cleavage sites marked '.' |
| MMP2/9 | 664'SAGYLDDVTL.'673 (128) |
| MMP9 | 1232'LNRKYEQAKN.'1241 (129) |

| LAMA2 | |
|---|---|
| Protease | Cleavage sites marked '.' |
| MMP2 | 1240'.QFEGKKLMAY'1249 (130) |
| MMP2/9 | 2314'.GLWNFREKEG'2323 (131) |

| LAMB1 | |
|---|---|
| Protease | Cleavage sites marked '.' |
| MMP9 | 209'ALDPAFKIED.'218 (132) |
| MMP2/9 | 1629'.SIESETAASE'1638 (133) |
| MMP2/9 | 1639'ETLFNASQRI.'1648 (134) |

| LAMA5 | |
|---|---|
| Protease | Cleavage sites marked '.' |
| MMP9 | 2402'.NSRNQERLEE'2411 (135) |
| MMP2/9 | 2901'EMDTLNEEVV.'2910 (136) |
| MMP9 | 3056'DLELADAYYL.'3065 (137) | wherein P indicates hydroxyproline, M indicates oxidised methionine, and K indicates hydroxylysine.

2. A method as claimed in claim 1, wherein said immunological binding partner is specifically reactive with any of the following sequences at the N terminal of the protein fragment:

| Collagen Type I Cleavage sites marked '.'/SEQ ID NO ( ) | |
|---|---|
| .AAGPPG | (138) |
| .AGPVGP | (139) |
| .DGRPGP | (140) |
| .EAGRPG | (141) |
| .GAPGLQ | (142) |
| .GLNGLP | (143) |
| .GLNGLP | (144) |
| .GLPGAK | (145) |
| .GPPGPP | (146) |
| .GPPGPP | (147) |
| .GVRGLT | (148) |
| .LPGPPG | (149) |
| .LPGPPG | (150) |
| .PGARGP | (151) |
| .PGKDGV | (152) |
| .PGPPGP | (153) |
| .PGPPGP | (154) |
| .PGPPGP | (155) |
| .RGEPGP | (156) |
| .RGLPGP | (157) |
| .VGPVGA | (158) |
| .DGLNGL | (159) |
| .AKGEPG | (160) |
| .AGARGN | (161) |
| .VGPPGP | (162) |
| .GAPGKD | (163) |
| .IGSAGP | (164) |
| .AGAPGK | (165) |
| .PPGPPG | (166) |
| .GPPGPP | (167) |
| .YDEKST | (168) |
| .ERGPPG | (169) |
| .IGNVGA | (170) |
| .AGKEGP | (171) |
| .KGADGS | (172) |

.D(β)GLNGLP (173)

Collagen Type III
Cleavage sites marked '.'/SEQ ID NO ( )

| | |
|---|---|
| .AGAQGP | (204) |
| .AGIPGV | (205) |
| .APGAPG | (206) |
| .ERGRPG | (207) |
| .GERGSP | (208) |
| .GFDGRN | (209) |
| .GGPGAD | (210) |
| .GLPGPP | (211) |
| .GLPGTG | (212) |
| .GPPGPA | (213) |
| .GPRGPT | (214) |
| .GSPGPA | (215) |
| .IAGITG | (216) |
| .KGDPGP | (217) |
| .KGDRGE | (218) |
| .LKGENG | (219) |
| .PGENGA | (220) |
| .PGERGE | (221) |
| .PGKNGA | (222) |
| .PGLKGE | (223) |
| .PGMRGM | (224) |
| .PPGKDG | (225) |
| .PQGPKG | (226) |
| .SPGAKG | (227) |

Collagen Type IV
Cleavage site marked '.'/SEQ ID NO ( )

| | |
|---|---|
| .IVIGTG | (251) |

Collagen Type V
Cleavage sites marked '.'/SEQ ID NO ( )

| | |
|---|---|
| .RRNIDA | (253) |
| .QQGGAG | (254) |
| .QRGAHG | (255) |
| .RVGKMG | (256) |
| .HMGREG | (257) |

Collagen Type VI
Cleavage sites marked '.'/SEQ ID NO ( )

| | |
|---|---|
| .RIAVAQ | (259) |
| .QLGTVQ | (260) |
| .RDVVFL | (261) |

Biglycan
Cleavage sites marked '.'/SEQ ID NO ( )

| | |
|---|---|
| .KLTGIP | (262) |
| .RAYYNG | (263) |
| .EISPDT | (264) |
| .IEMGGN | (265) |
| .NHLVEI | (266) |
| .NELHLD | (267) |
| .YWEVQP | (268) |
| .IQAIEL | (269) |

Decorin
Cleavage sites marked '.'/SEQ ID NO ( )

| | |
|---|---|
| .VPKDLP | (276) |

Versican
Cleavage sites marked '.'/SEQ ID NO ( )

| | |
|---|---|
| .YENWRP | (277) |
| .HDYQWI | (278) |
| .KTFGKM | (279) |
| SVTQIE | (304) |

ApoE
Cleavage sites marked '.'/SEQ ID NO ( )

| | |
|---|---|
| .LMDETM | (288) |
| .MEEMGS | (289) |

LAMA2
Cleavage sites marked '.'/SEQ ID NO ( )

| | |
|---|---|
| .QFEGKK | (294) |
| .GLWNFR | (295) |

LAMB1
Cleavage site marked '.'/SEQ ID NO ( )

| | |
|---|---|
| .SIESET | (296) |

LAMA5
Cleavage sites marked '.'/SEQ ID NO ( )

| | |
|---|---|
| .NSRNQE | (299) . |

3. A method as claimed in claim 1, wherein said immunological binding partner is specifically reactive with any of the following sequences at the C terminal of the protein fragment:

| Collagen Type I Cleavage sites marked '.'/SEQ ID NO ( ) | |
|---|---|
| AEGSPG. | (174) |
| AGAPGD. | (175) |
| AGPPGP. | (176) |
| AGPPGP. | (177) |
| APQLSY. | (178) |
| APQLSY. | (179) |
| EAGLPG. | (180) |
| GGRYYR. | (181) |
| GNFAPQ. | (182) |
| GNFAPQ. | (183) |
| GPAGAP. | (184) |
| GPPGAD. | (185) |
| GPPSAG. | (186) |
| IGPPGP. | (187) |
| IGPPGP. | (188) |
| IGPPGP. | (189) |
| ISVPGP. | (190) |
| LQGMPG. | (191) |
| NFAPQL. | (192) |
| PGAPGP. | (193) |
| PGPDGK. | (194) |
| PGPMGP. | (195) |
| PGPPGA. | (196) |
| PKGNSG. | (197) |
| PPSAGF. | (198) |
| PQLSYG. | (199) |
| PSAGFD. | (200) |
| QGPPGP. | (201) |
| RGRTGD. | (202) |
| VGARGP. | (203) |

| Collagen Type III Cleavage sites marked '.'/SEQ ID NO ( ) | |
|---|---|
| AGQPGD. | (228) |
| ENGSPG. | (229) |
| GDPGPP. | (230) |
| GERGPP. | (231) |
| GLPGAA. | (232) |
| GPAGIP. | (233) |
| GPPGIP. | (234) |
| GPPGPA. | (235) |
| GRPGLP. | (236) |
| GSPGGP. | (237) |
| GSPGPQ. | (238) |
| GVPGAK. | (239) |
| KGEPGP. | (240) |
| PAGIPG. | (241) |
| AGPRGP. | (242) |
| PGEPGP. | (243) |
| PGKDGP. | (244) |
| PRGAPG. | (245) |
| RGAPGE. | (246) |
| RGEPGP. | (247) |
| SGHPGP. | (248) |
| SGPKGD. | (249) |
| TGPPGP. | (250) |

| Collagen Type IV Cleavage site marked '.'/SEQ ID NO ( ) | |
|---|---|
| GIVIGT. | (252) |

| Collagen Type V Cleavage sites marked '.'/SEQ ID NO ( ) | |
|---|---|
| RGITGK. | (258) |

| Biglycan Cleavage sites marked '.'/SEQ ID NO ( ) | |
|---|---|
| TLNELH. | (270) |
| PKDLPE. | (271) |
| FNNPVP. | (272) |
| DISELR. | (273) |
| AFDGLK. | (274) |
| PNLPSS. | (275) |

| Versican Cleavage sites marked '.'/SEQ ID NO ( ) | |
|---|---|
| FSAGED. | (280) |
| VGPLVT. | (281) |

| Lumican Cleavage sites marked '.'/SEQ ID NO ( ) | |
|---|---|
| DHIDEK. | (282) |

| CRP Cleavage sites marked '.'/SEQ ID NO ( ) | |
|---|---|
| LSHAFG. | (283) |
| TSLSHA. | (284) |

-continued

| Elastin Cleavage sites marked '.'/SEQ ID NO ( ) | |
|---|---|
| LHPSRP. | (285) |
| KAAKYG. | (286) |
| GIGPGG. | (287) |

| ApoE Cleavage sites marked '.'/SEQ ID NO ( ) | |
|---|---|
| RLDEVK. | (290) |
| TPVAEE. | (291) |

| LAMC1 Cleavage sites marked '.'/SEQ ID NO ( ) | |
|---|---|
| LDDVTL. | (292) |
| YEQAKN. | (293) |

| LAMB1 Cleavage sites marked '.'/SEQ ID NO ( ) | |
|---|---|
| AFKIED. | (297) |
| NASQRI. | (298) |

| LAMA5 Cleavage sites marked '.'/SEQ ID NO ( ) | |
|---|---|
| LNEEVV. | (300) |
| ADAYYL. | (301). |

4. A method as claimed in claim 1, wherein said detection of binding is quantitative.

5. A method as claimed in claim 1, wherein the amount of binding is compared to control values established for populations of healthy individuals and of individuals characterised by a fibrotic disease or by an inflammatory condition.

6. A method as claimed in claim 1, conducted as a competition assay such that protein fragments in said sample compete for binding to the immunological binding partner with a known concentration of a binding agent which binds said immunological binding partner.

7. A method of diagnosis of quantitation of fibrosis comprising:
  obtaining a patient biofluid sample,
  conducting an immunoassay to measure an aggregate amount of N- or C-terminal neo-epitope containing protein fragments naturally present in a biofluid sample,
  associating an elevation of said measure in said patient above a normal level with the presence or extent of fibrosis, wherein said immunoassay is conducted by a method comprising:
    contacting protein fragments naturally present in said sample with an immunological binding partner reactive with a neo-epitope formed by cleavage of a protein by a proteinase; and
    measuring the extent of binding of protein fragments to said immunological binding partner to measure therein protein fragments comprising said neo-epitope, wherein said neo-epitope is formed by cleavage of collagen type V at the site 1317'.HMGRE-GREGE shown in SEQ ID NO: 93 and the neo-epitope is contained in the sequence HMGREG and wherein said immunological binding partner is raised against a synthetic peptide having an N-terminal sequence HMGREG shown in SEQ ID NO: 257.

* * * * *

SEQUENCE LISTING

```
<160> NUMBER OF SEQ ID NOS: 304

<210> SEQ ID NO 1
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: /
      hydroxyproline
      /
      /
<220> FEATURE:
<221> NAME/KEY: MOD_RES
<222> LOCATION: 9
<223> OTHER INFORMATION: oxidised methionine

<400> SEQUENCE: 1

Gln Gly Ala Pro Gly Leu Gln Gly Met Pro Gly Glu
1               5                   10

<210> SEQ ID NO 2
<211> LENGTH: 21
<212> TYPE: PRT
<213> ORGANISM: Homo sapiens
<220> FEATURE:
<221> NAME/KEY: SOURCE
<222> LOCATION: 1..21
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline
<220> FEATURE:
<221> NAME/KEY: MOD_RES
<222> LOCATION: 7
<223> OTHER INFORMATION: hydroxyproline
<220> FEATURE:
<221> NAME/KEY: MOD_RES
<222> LOCATION: 17
<223> OTHER INFORMATION: hydroxyproline

<400> SEQUENCE: 2

Asp Arg Gly Glu Pro Gly Pro Pro Gly Pro Ala Gly Phe Ala Gly Pro
1               5                   10                  15

Pro Gly Ala Asp Gly
            20

<210> SEQ ID NO 3
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
```

```
       /organism="Homo sapiens"
<220> FEATURE:
<221> NAME/KEY: MOD_RES
<222> LOCATION: 15
<223> OTHER INFORMATION: hydroxyproline
<220> FEATURE:
<221> NAME/KEY: MOD_RES
<222> LOCATION: 19
<223> OTHER INFORMATION: hydroxyproline

<400> SEQUENCE: 3

Asp Gly Val Arg Gly Leu Thr Gly Pro Ile Gly Pro Pro Gly Pro Ala
1               5                   10                  15

Gly Ala Pro Gly Asp Lys
            20

<210> SEQ ID NO 4
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline
<220> FEATURE:
<221> NAME/KEY: MOD_RES
<222> LOCATION: 7
<223> OTHER INFORMATION: hydroxylysine
<220> FEATURE:
<221> NAME/KEY: MOD_RES
<222> LOCATION: 16
<223> OTHER INFORMATION: hydroxyproline
<220> FEATURE:
<221> NAME/KEY: MOD_RES
<222> LOCATION: 18
<223> OTHER INFORMATION: hydroxyproline

<400> SEQUENCE: 4

Ala Gly Leu Pro Gly Ala Lys Gly Leu Thr Gly Ser Pro Gly Ser Pro
1               5                   10                  15

Gly Pro Asp Gly Lys Thr
            20

<210> SEQ ID NO 5
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 11
<223> OTHER INFORMATION: hydroxyproline
<220> FEATURE:
<221> NAME/KEY: MOD_RES
<222> LOCATION: 13
<223> OTHER INFORMATION: hydroxyproline
<220> FEATURE:
<221> NAME/KEY: MOD_RES
<222> LOCATION: 14
<223> OTHER INFORMATION: hydroxyproline
<220> FEATURE:
<221> NAME/KEY: MOD_RES
<222> LOCATION: 15
<223> OTHER INFORMATION: hydroxyproline
```

<400> SEQUENCE: 5

Asp Ala Gly Pro Val Gly Pro Pro Gly Pro Pro Gly Pro Pro Gly Pro
1               5                   10                  15

Pro Gly Pro Pro Ser Ala Gly Phe
            20

<210> SEQ ID NO 6
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"
<220> FEATURE:
<221> NAME/KEY: MOD_RES
<222> LOCATION: 12
<223> OTHER INFORMATION: hydroxyproline
<220> FEATURE:
<221> NAME/KEY: MOD_RES
<222> LOCATION: 13
<223> OTHER INFORMATION: hydroxyproline
<220> FEATURE:
<221> NAME/KEY: MOD_RES
<222> LOCATION: 15
<223> OTHER INFORMATION: hydroxyproline

<400> SEQUENCE: 6

Asp Gly Leu Asn Gly Leu Pro Gly Pro Ile Gly Pro Pro Gly Pro Arg
1               5                   10                  15

Gly Arg Thr Gly Asp Ala
            20

<210> SEQ ID NO 7
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 17
<223> OTHER INFORMATION: hydroxyproline
<220> FEATURE:
<221> NAME/KEY: MOD_RES
<222> LOCATION: 23
<223> OTHER INFORMATION: hydroxyproline

<400> SEQUENCE: 7

Ser Pro Gly Lys Asp Gly Val Arg Gly Leu Thr Gly Pro Ile Gly Pro
1               5                   10                  15

Pro Gly Pro Ala Gly Ala Pro Gly
            20

<210> SEQ ID NO 8
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES

```
<222> LOCATION: 5
<223> OTHER INFORMATION: hydroxyproline
<220> FEATURE:
<221> NAME/KEY: MOD_RES
<222> LOCATION: 7..8
<223> OTHER INFORMATION: hydroxyproline

<400> SEQUENCE: 8

Leu Pro Gly Pro Pro Gly Pro Pro Gly Pro Pro Gly Pro Pro Gly Leu
1               5                   10                  15

Gly Gly Asn Phe Ala Pro Gln Leu
            20

<210> SEQ ID NO 9
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxyproline
      /
<220> FEATURE:
<221> NAME/KEY: MOD_RES
<222> LOCATION: 4..5
<223> OTHER INFORMATION: hydroxyproline
<220> FEATURE:
<221> NAME/KEY: MOD_RES
<222> LOCATION: 22
<223> OTHER INFORMATION: hydroxyproline
      /

<400> SEQUENCE: 9

Leu Pro Gly Pro Pro Gly Pro Pro Gly Pro Pro Gly Pro Pro Gly Leu
1               5                   10                  15

Gly Gly Asn Phe Ala Pro Gln Leu
            20

<210> SEQ ID NO 10
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /organism="Homo sapiens"
<220> FEATURE:
<221> NAME/KEY: MOD_RES
<222> LOCATION: 6..7
<223> OTHER INFORMATION: hydroxyproline
<220> FEATURE:
<221> NAME/KEY: MOD_RES
<222> LOCATION: 9
<223> OTHER INFORMATION: hydroxyproline

<400> SEQUENCE: 10

Pro Gly Pro Pro Gly Pro Pro Gly Pro Pro Gly Leu Gly Gly Asn Phe
1               5                   10                  15

Ala Pro Gln Leu Ser Tyr Gly
            20

<210> SEQ ID NO 11
<211> LENGTH: 24
<212> TYPE: PRT
```

```
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 6..7
<223> OTHER INFORMATION: hydroxyproline
<220> FEATURE:
<221> NAME/KEY: MOD_RES
<222> LOCATION: 9..10
<223> OTHER INFORMATION: hydroxyproline

<400> SEQUENCE: 11

Pro Gly Pro Pro Gly Pro Pro Gly Pro Pro Gly Pro Pro Gly Leu Gly
1               5                   10                  15

Gly Asn Phe Ala Pro Gln Leu Ser
            20

<210> SEQ ID NO 12
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 10
<223> OTHER INFORMATION: hydroxyproline
<220> FEATURE:
<221> NAME/KEY: MOD_RES
<222> LOCATION: 13
<223> OTHER INFORMATION: hydroxyproline
<220> FEATURE:
<221> NAME/KEY: MOD_RES
<222> LOCATION: 16
<223> OTHER INFORMATION: hydroxyproline
<220> FEATURE:
<221> NAME/KEY: MOD_RES
<222> LOCATION: 20
<223> OTHER INFORMATION: hydroxylysine

<400> SEQUENCE: 12

Phe Pro Gly Ala Arg Gly Pro Ser Gly Pro Gln Gly Pro Gly Gly Pro
1               5                   10                  15

Pro Gly Pro Lys Gly Asn Ser Gly Glu
            20                  25

<210> SEQ ID NO 13
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5..6
<223> OTHER INFORMATION: hydroxyproline
<220> FEATURE:
<221> NAME/KEY: MOD_RES
<222> LOCATION: 23
```

```
<223> OTHER INFORMATION: hydroxyproline

<400> SEQUENCE: 13

Gly Leu Pro Gly Pro Pro Gly Pro Pro Gly Pro Pro Gly Pro Pro Gly
1               5                   10                  15

Leu Gly Gly Asn Phe Ala Pro Gln Leu
            20                  25

<210> SEQ ID NO 14
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 14..15
<223> OTHER INFORMATION: hydroxyproline
<220> FEATURE:
<221> NAME/KEY: MOD_RES
<222> LOCATION: 23
<223> OTHER INFORMATION: hydroxyproline

<400> SEQUENCE: 14

Gly Leu Pro Gly Pro Pro Gly Pro Pro Gly Pro Pro Gly Pro Pro Gly
1               5                   10                  15

Leu Gly Gly Asn Phe Ala Pro Gln Leu
            20                  25

<210> SEQ ID NO 15
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5..6
<223> OTHER INFORMATION: hydroxyproline
<220> FEATURE:
<221> NAME/KEY: MOD_RES
<222> LOCATION: 15
<223> OTHER INFORMATION: hydroxyproline
<220> FEATURE:
<221> NAME/KEY: MOD_RES
<222> LOCATION: 23
<223> OTHER INFORMATION: hydroxyproline

<400> SEQUENCE: 15

Gly Leu Pro Gly Pro Pro Gly Pro Pro Gly Pro Pro Gly Pro Pro Gly
1               5                   10                  15

Leu Gly Gly Asn Phe Ala Pro Gln Leu
            20                  25

<210> SEQ ID NO 16
<211> LENGTH: 26
```

```
<212> TYPE: PRT
<213> ORGANISM: Homo sapiens
<220> FEATURE:
<221> NAME/KEY: SOURCE
<222> LOCATION: 1..26
<223> OTHER INFORMATION: /mol_type="protein"
      /organism="Homo sapiens"
<220> FEATURE:
<221> NAME/KEY: MOD_RES
<222> LOCATION: 11
<223> OTHER INFORMATION: hydroxyproline
<220> FEATURE:
<221> NAME/KEY: MOD_RES
<222> LOCATION: 13..14
<223> OTHER INFORMATION: hydroxyproline
<220> FEATURE:
<221> NAME/KEY: MOD_RES
<222> LOCATION: 16..17
<223> OTHER INFORMATION: hydroxyproline

<400> SEQUENCE: 16

Asp Ala Gly Pro Val Gly Pro Pro Gly Pro Pro Gly Pro Pro Gly Pro
1               5                   10                  15

Pro Gly Pro Pro Ser Ala Gly Phe Asp Phe
            20                  25

<210> SEQ ID NO 17
<211> LENGTH: 44
<212> TYPE: PRT
<213> ORGANISM: Homo sapiens
<220> FEATURE:
<221> NAME/KEY: SOURCE
<222> LOCATION: 1..44
<223> OTHER INFORMATION: /mol_type="protein"
      /organism="Homo sapiens"
<220> FEATURE:
<221> NAME/KEY: MOD_RES
<222> LOCATION: 28
<223> OTHER INFORMATION: hydroxyproline
<220> FEATURE:
<221> NAME/KEY: MOD_RES
<222> LOCATION: 30..31
<223> OTHER INFORMATION: hydroxyproline
<220> FEATURE:
<221> NAME/KEY: MOD_RES
<222> LOCATION: 33..34
<223> OTHER INFORMATION: hydroxyproline
<220> FEATURE:
<221> NAME/KEY: MOD_RES
<222> LOCATION: 36..37
<223> OTHER INFORMATION: hydroxyproline

<400> SEQUENCE: 17

Asp Gly Leu Asn Gly Leu Pro Gly Pro Ile Gly Pro Pro Gly Pro Arg
1               5                   10                  15

Gly Arg Thr Gly Asp Ala Gly Pro Val Gly Pro Pro Gly Pro Pro Gly
                20                  25                  30

Pro Pro Gly Pro Pro Gly Pro Pro Ser Ala Gly Phe
            35                  40

<210> SEQ ID NO 18
<211> LENGTH: 44
<212> TYPE: PRT
<213> ORGANISM: Homo sapiens
<220> FEATURE:
<221> NAME/KEY: SOURCE
<222> LOCATION: 1..44
<223> OTHER INFORMATION: /mol_type="protein"
      /organism="Homo sapiens"
<220> FEATURE:
<221> NAME/KEY: MOD_RES
<222> LOCATION: 6..7
```

```
<223> OTHER INFORMATION: hydroxyproline
<220> FEATURE:
<221> NAME/KEY: MOD_RES
<222> LOCATION: 9..10
<223> OTHER INFORMATION: hydroxyproline
<220> FEATURE:
<221> NAME/KEY: MOD_RES
<222> LOCATION: 30
<223> OTHER INFORMATION: hydroxylysine
<220> FEATURE:
<221> NAME/KEY: MOD_RES
<222> LOCATION: 41
<223> OTHER INFORMATION: oxidised methionine

<400> SEQUENCE: 18

Pro Gly Pro Pro Gly Pro Pro Gly Pro Pro Gly Pro Pro Gly Leu Gly
1               5                   10                  15

Gly Asn Phe Ala Pro Gln Leu Ser Tyr Gly Tyr Asp Glu Lys Ser Thr
            20                  25                  30

Gly Gly Ile Ser Val Pro Gly Pro Met Gly Pro Ser
        35                  40

<210> SEQ ID NO 19
<211> LENGTH: 46
<212> TYPE: PRT
<213> ORGANISM: Homo sapiens
<220> FEATURE:
<221> NAME/KEY: SOURCE
<222> LOCATION: 1..46
<223> OTHER INFORMATION: /mol_type="protein"
      /organism="Homo sapiens"
<220> FEATURE:
<221> NAME/KEY: MOD_RES
<222> LOCATION: 24
<223> OTHER INFORMATION: hydroxyproline
<220> FEATURE:
<221> NAME/KEY: MOD_RES
<222> LOCATION: 27..28
<223> OTHER INFORMATION: hydroxyproline
<220> FEATURE:
<221> NAME/KEY: MOD_RES
<222> LOCATION: 30..31
<223> OTHER INFORMATION: hydroxyproline
<220> FEATURE:
<221> NAME/KEY: MOD_RES
<222> LOCATION: 33..34
<223> OTHER INFORMATION: hydroxyproline
<220> FEATURE:
<221> NAME/KEY: MOD_RES
<222> LOCATION: 36
<223> OTHER INFORMATION: hydroxyproline

<400> SEQUENCE: 19

Asp Gly Leu Asn Gly Leu Pro Gly Pro Ile Gly Pro Pro Gly Pro Arg
1               5                   10                  15

Gly Arg Thr Gly Asp Ala Gly Pro Val Gly Pro Pro Gly Pro Pro Gly
            20                  25                  30

Pro Pro Gly Pro Pro Gly Pro Pro Ser Ala Gly Phe Asp Phe
        35                  40                  45

<210> SEQ ID NO 20
<211> LENGTH: 21
<212> TYPE: PRT
<213> ORGANISM: Homo sapiens
<220> FEATURE:
<221> NAME/KEY: SOURCE
<222> LOCATION: 1..21
<223> OTHER INFORMATION: /mol_type="protein"
      /organism="Homo sapiens"
<220> FEATURE:
<221> NAME/KEY: MOD_RES
```

```
<222> LOCATION: 5
<223> OTHER INFORMATION: hydroxyproline
<220> FEATURE:
<221> NAME/KEY: MOD_RES
<222> LOCATION: 7
<223> OTHER INFORMATION: hydroxyproline
<220> FEATURE:
<221> NAME/KEY: MOD_RES
<222> LOCATION: 17
<223> OTHER INFORMATION: hydroxyproline

<400> SEQUENCE: 20

Asp Arg Gly Glu Pro Gly Pro Pro Gly Pro Ala Gly Phe Ala Gly Pro
1               5                   10                  15

Pro Gly Ala Asp Gly
            20

<210> SEQ ID NO 21
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"
<220> FEATURE:
<221> NAME/KEY: MOD_RES
<222> LOCATION: 13
<223> OTHER INFORMATION: hydroxyproline
<220> FEATURE:
<221> NAME/KEY: MOD_RES
<222> LOCATION: 19
<223> OTHER INFORMATION: hydroxyproline

<400> SEQUENCE: 21

Asp Gly Val Arg Gly Leu Thr Gly Pro Ile Gly Pro Pro Gly Pro Ala
1               5                   10                  15

Gly Ala Pro Gly Asp Lys
            20

<210> SEQ ID NO 22
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 10..11
<223> OTHER INFORMATION: hydroxyproline
<220> FEATURE:
<221> NAME/KEY: MOD_RES
<222> LOCATION: 13..14
<223> OTHER INFORMATION: hydroxyproline

<400> SEQUENCE: 22

Asp Ala Gly Pro Val Gly Pro Pro Gly Pro Pro Gly Pro Pro Gly Pro
1               5                   10                  15

Pro Gly Pro Pro Ser Ala Gly Phe
            20

<210> SEQ ID NO 23
<211> LENGTH: 22
<212> TYPE: PRT
<213> ORGANISM: Homo sapiens
<220> FEATURE:
```

```
<221> NAME/KEY: SOURCE
<222> LOCATION: 1..22
<223> OTHER INFORMATION: /mol_type="protein"
      /organism="Homo sapiens"
<220> FEATURE:
<221> NAME/KEY: MOD_RES
<222> LOCATION: 7
<223> OTHER INFORMATION: hydroxyproline
<220> FEATURE:
<221> NAME/KEY: MOD_RES
<222> LOCATION: 12..13
<223> OTHER INFORMATION: hydroxyproline

<400> SEQUENCE: 23

Asp Gly Leu Asn Gly Leu Pro Gly Pro Ile Gly Pro Pro Gly Pro Arg
1               5                   10                  15

Gly Arg Thr Gly Asp Ala
            20

<210> SEQ ID NO 24
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 13..14
<223> OTHER INFORMATION: hydroxyproline
<220> FEATURE:
<221> NAME/KEY: MOD_RES
<222> LOCATION: 16
<223> OTHER INFORMATION: hydroxyproline

<400> SEQUENCE: 24

Asp Ala Gly Pro Val Gly Pro Pro Gly Pro Pro Gly Pro Pro Gly Pro
1               5                   10                  15

Pro Gly Pro Pro Ser Ala Gly Phe Asp
            20                  25

<210> SEQ ID NO 25
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxyproline
<220> FEATURE:
<221> NAME/KEY: MOD_RES
<222> LOCATION: 13..14
<223> OTHER INFORMATION: hydroxyproline
<220> FEATURE:
<221> NAME/KEY: MOD_RES
<222> LOCATION: 22
<223> OTHER INFORMATION: hydroxyproline

<400> SEQUENCE: 25

Leu Pro Gly Pro Pro Gly Pro Pro Gly Pro Pro Gly Pro Pro Gly Leu
1               5                   10                  15

Gly Gly Asn Phe Ala Pro Gln Leu
            20
```

```
<210> SEQ ID NO 26
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /organism="Homo sapiens"
<220> FEATURE:
<221> NAME/KEY: MOD_RES
<222> LOCATION: 3..4
<223> OTHER INFORMATION: hydroxyproline
<220> FEATURE:
<221> NAME/KEY: MOD_RES
<222> LOCATION: 18
<223> OTHER INFORMATION: hydroxyproline
<220> FEATURE:
<221> NAME/KEY: MOD_RES
<222> LOCATION: 10
<223> OTHER INFORMATION: hydroxyproline

<400> SEQUENCE: 26

Pro Gly Pro Pro Gly Pro Pro Gly Pro Pro Gly Leu Gly Gly Asn Phe
1               5                   10                  15

Ala Pro Gln Leu Ser Tyr Gly
            20

<210> SEQ ID NO 27
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 6..7
<223> OTHER INFORMATION: hydroxyproline
<220> FEATURE:
<221> NAME/KEY: MOD_RES
<222> LOCATION: 9..10
<223> OTHER INFORMATION: hydroxyproline

<400> SEQUENCE: 27

Pro Gly Pro Pro Gly Pro Pro Gly Pro Pro Gly Pro Pro Gly Leu Gly
1               5                   10                  15

Gly Asn Phe Ala Pro Gln Leu Ser
            20

<210> SEQ ID NO 28
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5..6
<223> OTHER INFORMATION: hydroxyproline
<220> FEATURE:
<221> NAME/KEY: MOD_RES
<222> LOCATION: 23
```

<223> OTHER INFORMATION: hydroxyproline

<400> SEQUENCE: 28

Gly Leu Pro Gly Pro Pro Gly Pro Pro Gly Pro Pro Gly Pro Pro Gly
1               5                   10                  15

Leu Gly Gly Asn Phe Ala Pro Gln Leu
            20                  25

<210> SEQ ID NO 29
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline
<220> FEATURE:
<221> NAME/KEY: MOD_RES
<222> LOCATION: 7..8
<223> OTHER INFORMATION: hydroxyproline
<220> FEATURE:
<221> NAME/KEY: MOD_RES
<222> LOCATION: 10..11
<223> OTHER INFORMATION: hydroxyproline

<400> SEQUENCE: 29

Leu Pro Gly Pro Pro Gly Pro Pro Gly Pro Pro Gly Pro Pro Gly Leu
1               5                   10                  15

Gly Gly Asn Phe Ala Pro Gln Leu Ser
            20                  25

<210> SEQ ID NO 30
<211> LENGTH: 39
<212> TYPE: PRT
<213> ORGANISM: Homo sapiens
<220> FEATURE:
<221> NAME/KEY: SOURCE
<222> LOCATION: 1..39
<223> OTHER INFORMATION: /mol_type="protein"
      /organism="Homo sapiens"
<220> FEATURE:
<221> NAME/KEY: MOD_RES
<222> LOCATION: 6..7
<223> OTHER INFORMATION: hydroxyproline
<220> FEATURE:
<221> NAME/KEY: MOD_RES
<222> LOCATION: 9..10
<223> OTHER INFORMATION: hydroxyproline
<220> FEATURE:
<221> NAME/KEY: MOD_RES
<222> LOCATION: 29
<223> OTHER INFORMATION: hydroxylysine

<400> SEQUENCE: 30

Pro Gly Pro Pro Gly Pro Pro Gly Pro Pro Gly Pro Pro Ser Ala Gly
1               5                   10                  15

Phe Asp Phe Ser Phe Leu Pro Gln Pro Pro Gln Glu Lys Ala His Asp
            20                  25                  30

Gly Gly Arg Tyr Tyr Arg Ala
        35

<210> SEQ ID NO 31
<211> LENGTH: 9
<212> TYPE: PRT

```
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 31

Gly Ala Ala Gly Pro Pro Gly Pro Thr
1               5

<210> SEQ ID NO 32
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 32

Pro Val Gly Pro Val Gly Ala Arg Gly Pro Ala
1               5                   10

<210> SEQ ID NO 33
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 33

Pro Ala Gly Pro Val Gly Pro Val Gly Ala Arg Gly Pro Ala
1               5                   10

<210> SEQ ID NO 34
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline
<220> FEATURE:
<221> NAME/KEY: MOD_RES
<222> LOCATION: 8
<223> OTHER INFORMATION: hydroxyproline
<220> FEATURE:
<221> NAME/KEY: MOD_RES
<222> LOCATION: 11
<223> OTHER INFORMATION: hydroxyproline

<400> SEQUENCE: 34

Pro Arg Gly Leu Pro Gly Pro Pro Gly Ala Pro Gly Pro Gln
1               5                   10

<210> SEQ ID NO 35
<211> LENGTH: 14
<212> TYPE: PRT
<213> ORGANISM: Homo sapiens
<220> FEATURE:
<221> NAME/KEY: SOURCE
```

```
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 6
<223> OTHER INFORMATION: hydroxyproline

<400> SEQUENCE: 35

Gly Glu Ala Gly Arg Pro Gly Glu Ala Gly Leu Pro Gly Ala
1               5                   10

<210> SEQ ID NO 36
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline
<220> FEATURE:
<221> NAME/KEY: MOD_RES
<222> LOCATION: 7..8
<223> OTHER INFORMATION: hydroxyproline
<220> FEATURE:
<221> NAME/KEY: MOD_RES
<222> LOCATION: 10..11
<223> OTHER INFORMATION: hydroxyproline

<400> SEQUENCE: 36

Gln Asp Gly Arg Pro Gly Pro Pro Gly Pro Pro Gly Ala Arg
1               5                   10

<210> SEQ ID NO 37
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"
<220> FEATURE:
<221> NAME/KEY: MOD_RES
<222> LOCATION: 8
<223> OTHER INFORMATION: hydroxyproline
<220> FEATURE:
<221> NAME/KEY: MOD_RES
<222> LOCATION: 14
<223> OTHER INFORMATION: hydroxyproline

<400> SEQUENCE: 37

Lys Asp Gly Leu Asn Gly Leu Pro Gly Pro Ile Gly Pro Pro Gly Pro
1               5                   10                  15

Arg

<210> SEQ ID NO 38
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"
<220> FEATURE:
<221> NAME/KEY: MOD_RES
```

```
<222> LOCATION: 6
<223> OTHER INFORMATION: hydroxyproline
<220> FEATURE:
<221> NAME/KEY: MOD_RES
<222> LOCATION: 8
<223> OTHER INFORMATION: hydroxyproline
<220> FEATURE:
<221> NAME/KEY: MOD_RES
<222> LOCATION: 15
<223> OTHER INFORMATION: hydroxyproline

<400> SEQUENCE: 38

Gly Ala Lys Gly Glu Pro Gly Pro Val Gly Val Gln Gly Pro Pro Gly
1               5                   10                  15

Pro Ala

<210> SEQ ID NO 39
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"
<220> FEATURE:
<221> NAME/KEY: MOD_RES
<222> LOCATION: 17
<223> OTHER INFORMATION: hydroxyproline

<400> SEQUENCE: 39

Pro Ala Gly Ala Arg Gly Asn Asp Gly Ala Thr Gly Ala Ala Gly Pro
1               5                   10                  15

Pro Gly Pro Thr
            20

<210> SEQ ID NO 40
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"
<220> FEATURE:
<221> NAME/KEY: MOD_RES
<222> LOCATION: 7..8
<223> OTHER INFORMATION: hydroxyproline
<220> FEATURE:
<221> NAME/KEY: MOD_RES
<222> LOCATION: 10
<223> OTHER INFORMATION: hydroxyproline

<400> SEQUENCE: 40

Pro Val Gly Pro Pro Gly Pro Pro Gly Pro Pro Gly Pro Pro Gly Pro
1               5                   10                  15

Pro Ser Ala Gly Phe Asp
            20

<210> SEQ ID NO 41
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"
<220> FEATURE:
```

```
<221> NAME/KEY: MOD_RES
<222> LOCATION: 4
<223> OTHER INFORMATION: hydroxyproline
<220> FEATURE:
<221> NAME/KEY: MOD_RES
<222> LOCATION: 6
<223> OTHER INFORMATION: hydroxylysine

<400> SEQUENCE: 41

Ala Gly Ala Pro Gly Lys Asp Gly Leu Asn Gly Leu Pro Gly Ile
1               5                   10                  15

Gly Pro Pro Gly Pro Arg
            20

<210> SEQ ID NO 42
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 11
<223> OTHER INFORMATION: hydroxyproline
<220> FEATURE:
<221> NAME/KEY: MOD_RES
<222> LOCATION: 13..14
<223> OTHER INFORMATION: hydroxyproline
<220> FEATURE:
<221> NAME/KEY: MOD_RES
<222> LOCATION: 16
<223> OTHER INFORMATION: hydroxproline

<400> SEQUENCE: 42

Asp Ala Gly Pro Val Gly Pro Pro Gly Pro Pro Gly Pro Pro Gly Pro
1               5                   10                  15

Pro Gly Pro Pro Ser Ala Gly Phe
            20

<210> SEQ ID NO 43
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /organism="Homo sapiens"
<220> FEATURE:
<221> NAME/KEY: MOD_RES
<222> LOCATION: 15
<223> OTHER INFORMATION: hydroxyproline
<220> FEATURE:
<221> NAME/KEY: MOD_RES
<222> LOCATION: 17
<223> OTHER INFORMATION: hydroxyproline
<220> FEATURE:
<221> NAME/KEY: MOD_RES
<222> LOCATION: 20..21
<223> OTHER INFORMATION: hydroxyproline

<400> SEQUENCE: 43

Ser Ala Gly Ala Pro Gly Lys Asp Gly Leu Asn Gly Leu Pro Gly Pro
1               5                   10                  15

Ile Gly Pro Pro Gly Pro Arg
            20
```

```
<210> SEQ ID NO 44
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /organism="Homo sapiens"
<220> FEATURE:
<221> NAME/KEY: MOD_RES
<222> LOCATION: 8..9
<223> OTHER INFORMATION: hydroxyproline
<220> FEATURE:
<221> NAME/KEY: MOD_RES
<222> LOCATION: 17
<223> OTHER INFORMATION: hydroxyproline

<400> SEQUENCE: 44

Gly Pro Pro Gly Pro Pro Gly Pro Pro Gly Leu Gly Gly Asn Phe Ala
1               5                   10                  15

Pro Gln Leu Ser Tyr Gly Tyr
            20

<210> SEQ ID NO 45
<211> LENGTH: 24
<212> TYPE: PRT
<213> ORGANISM: Homo sapiens
<220> FEATURE:
<221> NAME/KEY: SOURCE
<222> LOCATION: 1..24
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline
<220> FEATURE:
<221> NAME/KEY: MOD_RES
<222> LOCATION: 6..7
<223> OTHER INFORMATION: hydroxyproline

<400> SEQUENCE: 45

Pro Gly Pro Pro Gly Pro Pro Gly Pro Pro Gly Pro Pro Gly Leu Gly
1               5                   10                  15

Gly Asn Phe Ala Pro Gln Leu Ser
            20

<210> SEQ ID NO 46
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5..6
<223> OTHER INFORMATION: hydroxyproline
<220> FEATURE:
<221> NAME/KEY: MOD_RES
<222> LOCATION: 23
<223> OTHER INFORMATION: hydroxyproline

<400> SEQUENCE: 46

Gly Leu Pro Gly Pro Pro Gly Pro Pro Gly Pro Pro Gly Pro Pro Gly
```

```
                1               5                  10                 15
Leu Gly Gly Asn Phe Ala Pro Gln Leu
                20                 25

<210> SEQ ID NO 47
<211> LENGTH: 35
<212> TYPE: PRT
<213> ORGANISM: Homo sapiens
<220> FEATURE:
<221> NAME/KEY: SOURCE
<222> LOCATION: 1..35
<223> OTHER INFORMATION: /mol_type="protein"
      /organism="Homo sapiens"
<220> FEATURE:
<221> NAME/KEY: MOD_RES
<222> LOCATION: 9
<223> OTHER INFORMATION: oxidised methionine

<400> SEQUENCE: 47

Gly Glu Arg Gly Pro Pro Gly Pro Met Gly Pro Pro Gly Leu Ala Gly
1               5                  10                  15

Pro Pro Gly Glu Ser Gly Arg Glu Gly Ala Pro Gly Ala Glu Gly Ser
                20                  25                  30

Pro Gly Arg
        35

<210> SEQ ID NO 48
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 48

Ile Gly Asn Val Gly Ala Pro Gly Ala Lys
1               5                  10

<210> SEQ ID NO 49
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 49

Ala Gly Lys Glu Gly Pro Val Gly Leu Pro
1               5                  10

<210> SEQ ID NO 50
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 50

Ile Gly Ser Ala Gly Pro Pro Gly Phe Pro
1               5                  10
```

```
<210> SEQ ID NO 51
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 51

Asp Gly Leu Asn Gly Leu Pro Gly Pro Ile
1               5                   10

<210> SEQ ID NO 52
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: beta bond

<400> SEQUENCE: 52

Asp Gly Leu Asn Gly Leu Pro Gly Pro Ile
1               5                   10

<210> SEQ ID NO 53
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 53

Lys Gly Ala Asp Gly Ser Pro Gly Lys Asp
1               5                   10

<210> SEQ ID NO 54
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 54

Ser Thr Gly Gly Ile Ser Val Pro Gly Pro
1               5                   10

<210> SEQ ID NO 55
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"
```

```
<400> SEQUENCE: 55

Tyr Asp Glu Lys Ser Thr Gly Gly Ile Ser
1               5                   10

<210> SEQ ID NO 56
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 56

Glu Ala Gly Ile Pro Gly Val Pro Gly Ala Lys Gly
1               5                   10

<210> SEQ ID NO 57
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 57

Pro Lys Gly Asp Pro Gly Pro Pro Gly Ile Pro Gly
1               5                   10

<210> SEQ ID NO 58
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 58

Gly Pro Gln Gly Pro Lys Gly Asp Pro Gly Pro Pro Gly
1               5                   10

<210> SEQ ID NO 59
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 59

Gly Pro Gly Met Arg Gly Met Pro Gly Ser Pro Gly Gly Pro Gly
1               5                   10                  15

<210> SEQ ID NO 60
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"
```

<400> SEQUENCE: 60

Asp Gly Pro Pro Gly Pro Ala Gly Asn Thr Gly Ala Pro Gly Ser Pro
1               5                   10                  15

Gly Val Ser Gly Pro Lys Gly Asp Ala
            20                  25

<210> SEQ ID NO 61
<211> LENGTH: 30
<212> TYPE: PRT
<213> ORGANISM: Homo sapiens
<220> FEATURE:
<221> NAME/KEY: SOURCE
<222> LOCATION: 1..30
<223> OTHER INFORMATION: /mol_type="protein"
      /organism="Homo sapiens"

<400> SEQUENCE: 61

His Ala Gly Ala Gln Gly Pro Pro Gly Pro Pro Gly Ile Asn Gly Ser
1               5                   10                  15

Pro Gly Gly Lys Gly Glu Met Gly Pro Ala Gly Ile Pro Gly
            20                  25                  30

<210> SEQ ID NO 62
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"

<400> SEQUENCE: 62

Asp Gly Pro Arg Gly Pro Thr Gly Pro Ile Gly Pro Pro Gly Pro Ala
1               5                   10                  15

Gly Gln Pro Gly Asp Lys
            20

<210> SEQ ID NO 63
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"

<400> SEQUENCE: 63

Asp Gly Pro Pro Gly Pro Ala Gly Asn Thr Gly Ala Pro Gly Ser Pro
1               5                   10                  15

Gly Val Ser Gly Pro Lys Gly Asp Ala
            20                  25

<210> SEQ ID NO 64
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"

<400> SEQUENCE: 64

```
Pro Gly Ser Pro Gly Pro Ala Gly Gln Gln Gly Ala Ile Gly Ser Pro
1               5                   10                  15

Gly Pro Ala Gly Pro Arg Gly Pro Val
            20                  25
```

<210> SEQ ID NO 65
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 65

```
Gly Glu Arg Gly Arg Pro Gly Leu Pro Gly
1               5                   10
```

<210> SEQ ID NO 66
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 66

```
Gly Lys Gly Asp Arg Gly Glu Asn Gly Ser Pro Gly Ala
1               5                   10
```

<210> SEQ ID NO 67
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 67

```
Glu Pro Gly Lys Asn Gly Ala Lys Gly Glu Pro Gly Pro Arg
1               5                   10
```

<210> SEQ ID NO 68
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 68

```
Ser Pro Gly Glu Arg Gly Glu Thr Gly Pro Pro Gly Pro Ala
1               5                   10
```

<210> SEQ ID NO 69
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"

/organism="Homo sapiens"

<400> SEQUENCE: 69

Pro Gly Gly Pro Gly Ala Asp Gly Val Pro Gly Lys Asp Gly Pro Arg
1               5                   10                  15

<210> SEQ ID NO 70
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 70

Gly Pro Pro Gly Lys Asp Gly Thr Ser Gly His Pro Gly Pro Ile
1               5                   10                  15

<210> SEQ ID NO 71
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 71

Arg Gly Leu Pro Gly Pro Pro Gly Ile Lys Gly Pro Ala Gly Ile Pro
1               5                   10                  15

Gly Phe

<210> SEQ ID NO 72
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"

<400> SEQUENCE: 72

Leu Pro Gly Glu Asn Gly Ala Pro Gly Pro Met Gly Pro Arg Gly Ala
1               5                   10                  15

Pro Gly Glu Arg
            20

<210> SEQ ID NO 73
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"

<400> SEQUENCE: 73

Gly Ala Pro Gly Ala Pro Gly Gly Lys Gly Asp Ala Gly Ala Pro Gly
1               5                   10                  15

Glu Arg Gly Pro Pro Gly
            20

```
<210> SEQ ID NO 74
<211> LENGTH: 28
<212> TYPE: PRT
<213> ORGANISM: Homo sapiens
<220> FEATURE:
<221> NAME/KEY: SOURCE
<222> LOCATION: 1..28
<223> OTHER INFORMATION: /mol_type="protein"
      /organism="Homo sapiens"

<400> SEQUENCE: 74

Ala Pro Gly Leu Lys Gly Glu Asn Gly Leu Pro Gly Glu Asn Gly Ala
1               5                   10                  15

Pro Gly Pro Met Gly Pro Arg Gly Ala Pro Gly Glu
            20                  25

<210> SEQ ID NO 75
<211> LENGTH: 28
<212> TYPE: PRT
<213> ORGANISM: Homo sapiens
<220> FEATURE:
<221> NAME/KEY: SOURCE
<222> LOCATION: 1..28
<223> OTHER INFORMATION: /mol_type="protein"
      /organism="Homo sapiens"

<400> SEQUENCE: 75

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly
            20                  25

<210> SEQ ID NO 76
<211> LENGTH: 30
<212> TYPE: PRT
<213> ORGANISM: Homo sapiens
<220> FEATURE:
<221> NAME/KEY: SOURCE
<222> LOCATION: 1..30
<223> OTHER INFORMATION: /mol_type="protein"
      /organism="Homo sapiens"

<400> SEQUENCE: 76

Gly Ser Pro Gly Ala Lys Gly Glu Val Gly Pro Ala Gly Ser Pro Gly
1               5                   10                  15

Ser Asn Gly Ala Pro Gly Gln Arg Gly Glu Pro Gly Pro Gln
            20                  25                  30

<210> SEQ ID NO 77
<211> LENGTH: 37
<212> TYPE: PRT
<213> ORGANISM: Homo sapiens
<220> FEATURE:
<221> NAME/KEY: SOURCE
<222> LOCATION: 1..37
<223> OTHER INFORMATION: /mol_type="protein"
      /organism="Homo sapiens"

<400> SEQUENCE: 77

Gly Leu Lys Gly Glu Asn Gly Leu Pro Gly Glu Asn Gly Ala Pro Gly
1               5                   10                  15

Pro Met Gly Pro Arg Gly Ala Pro Gly Glu Arg Gly Arg Pro Gly Leu
            20                  25                  30

Pro Gly Ala Ala Gly
        35
```

```
<210> SEQ ID NO 78
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"

<400> SEQUENCE: 78

Asp Gly Pro Pro Gly Pro Ala Gly Asn Thr Gly Ala Pro Gly Ser Pro
1               5                   10                  15

Gly Val Ser Gly Pro Lys Gly Asp Ala
            20                  25

<210> SEQ ID NO 79
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 79

Gly Phe Asp Gly Arg Asn Gly Glu Lys Gly
1               5                   10

<210> SEQ ID NO 80
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 80

Pro Gly Met Arg Gly Met Pro Gly Ser Pro
1               5                   10

<210> SEQ ID NO 81
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 81

Gly Leu Pro Gly Thr Gly Gly Pro Pro Gly
1               5                   10

<210> SEQ ID NO 82
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 82
```

Glu Asn Gly Lys Pro Gly Glu Pro Gly Pro
1               5                   10

<210> SEQ ID NO 83
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 83

Gly Glu Arg Gly Ser Pro Gly Gly Pro Gly
1               5                   10

<210> SEQ ID NO 84
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 84

Pro Gly Lys Asp Gly Pro Pro Gly Pro Ala
1               5                   10

<210> SEQ ID NO 85
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 85

Gly Leu Pro Gly Thr Gly Gly Pro Pro Gly
1               5                   10

<210> SEQ ID NO 86
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 86

Ile Val Ile Gly Thr Gly Pro Leu Gly Glu
1               5                   10

<210> SEQ ID NO 87
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

```
<400> SEQUENCE: 87

Pro Gly Pro Pro Gly Ile Val Ile Gly Thr
1               5                   10

<210> SEQ ID NO 88
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 88

Glu Arg Gly Pro Arg Gly Ile Thr Gly Lys
1               5                   10

<210> SEQ ID NO 89
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 89

Arg Arg Asn Ile Asp Ala Ser Gln Leu Leu
1               5                   10

<210> SEQ ID NO 90
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 90

Gln Gln Gly Gly Ala Gly Pro Thr Gly Pro
1               5                   10

<210> SEQ ID NO 91
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 91

Gln Arg Gly Ala His Gly Met Pro Gly Lys
1               5                   10

<210> SEQ ID NO 92
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"
```

<400> SEQUENCE: 92

Arg Val Gly Lys Met Gly Arg Pro Gly Ala
1               5                   10

<210> SEQ ID NO 93
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 93

His Met Gly Arg Glu Gly Arg Glu Gly Glu
1               5                   10

<210> SEQ ID NO 94
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 94

Arg Ile Ala Val Ala Gln Tyr Ser Asp Asp
1               5                   10

<210> SEQ ID NO 95
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 95

Gln Leu Gly Thr Val Gln Gln Val Ile Ser
1               5                   10

<210> SEQ ID NO 96
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 96

Arg Asp Val Val Phe Leu Ile Asp Gly Ser
1               5                   10

<210> SEQ ID NO 97
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"

/organism="Homo sapiens"

<400> SEQUENCE: 97

Leu Met Asp Glu Thr Met
1               5

<210> SEQ ID NO 98
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 98

Arg Leu Asp Glu Val Lys
1               5

<210> SEQ ID NO 99
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 99

Thr Pro Val Ala Glu Glu
1               5

<210> SEQ ID NO 100
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 100

Met Glu Glu Met Gly Ser
1               5

<210> SEQ ID NO 101
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 101

Lys Leu Thr Gly Ile Pro Lys Asp Leu Pro
1               5                   10

<210> SEQ ID NO 102
<211> LENGTH: 10
<212> TYPE: PRT
<213> ORGANISM: Homo sapiens
<220> FEATURE:
<221> NAME/KEY: SOURCE
<222> LOCATION: 1..10

<223> OTHER INFORMATION: /mol_type="protein"
      /organism="Homo sapiens"

<400> SEQUENCE: 102

Asp Leu Pro Glu Thr Leu Asn Glu Leu His
1               5                   10

<210> SEQ ID NO 103
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 103

Leu Thr Gly Ile Pro Lys Asp Leu Pro Glu
1               5                   10

<210> SEQ ID NO 104
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 104

Arg Ala Tyr Tyr Asn Gly Ile Ser Leu Phe
1               5                   10

<210> SEQ ID NO 105
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 105

Gly Ile Ser Leu Phe Asn Asn Pro Val Pro
1               5                   10

<210> SEQ ID NO 106
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 106

Glu Ile Ser Pro Asp Thr Thr Leu Leu Asp
1               5                   10

<210> SEQ ID NO 107
<211> LENGTH: 10
<212> TYPE: PRT
<213> ORGANISM: Homo sapiens
<220> FEATURE:
<221> NAME/KEY: SOURCE

```
<222> LOCATION: 1..10
<223> OTHER INFORMATION: /mol_type="protein"
      /organism="Homo sapiens"

<400> SEQUENCE: 107

Leu Gln Asn Asn Asp Ile Ser Glu Leu Arg
1               5                   10

<210> SEQ ID NO 108
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 108

Ile Glu Met Gly Gly Asn Pro Leu Glu Asn Ser
1               5                   10

<210> SEQ ID NO 109
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 109

Phe Glu Pro Gly Ala Phe Asp Gly Leu Lys
1               5                   10

<210> SEQ ID NO 110
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 110

Asn His Leu Val Glu Ile Pro Pro Asn Leu
1               5                   10

<210> SEQ ID NO 111
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 111

Val Glu Ile Pro Pro Asn Leu Pro Ser Ser
1               5                   10

<210> SEQ ID NO 112
<211> LENGTH: 9
<212> TYPE: PRT
<213> ORGANISM: Homo sapiens
<220> FEATURE:
```

```
<221> NAME/KEY: SOURCE
<222> LOCATION: 1..9
<223> OTHER INFORMATION: /mol_type="protein"
      /organism="Homo sapiens"

<400> SEQUENCE: 112

Asn Glu Leu His Leu Asp His Asn Lys
1               5

<210> SEQ ID NO 113
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 113

Tyr Trp Glu Val Gln Pro Ala Thr Phe Arg
1               5                   10

<210> SEQ ID NO 114
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 114

Ile Gln Ala Ile Glu Leu Glu Asp Leu Leu
1               5                   10

<210> SEQ ID NO 115
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 115

Val Pro Lys Asp Leu Pro Pro Asp Thr Thr
1               5                   10

<210> SEQ ID NO 116
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 116

Tyr Glu Asn Trp Arg Pro Asn Gln Pro Asp
1               5                   10

<210> SEQ ID NO 117
<211> LENGTH: 10
<212> TYPE: PRT
<213> ORGANISM: Homo sapiens
```

```
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 117

Pro Asp Ser Phe Phe Ser Ala Gly Glu Asp
1               5                   10

<210> SEQ ID NO 118
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 118

His Asp Tyr Gln Trp Ile Gly Leu Asn
1               5

<210> SEQ ID NO 119
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 119

Lys Thr Phe Gly Lys Met Lys Pro Arg Tyr
1               5                   10

<210> SEQ ID NO 120
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 120

Ser Val Thr Gln Ile Glu Gln Ile Glu Val
1               5                   10

<210> SEQ ID NO 121
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 121

Glu Gln Ile Glu Val Gly Pro Leu Val Thr
1               5                   10

<210> SEQ ID NO 122
<211> LENGTH: 6
<212> TYPE: PRT
```

```
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 122

Leu Ser His Ala Phe Gly
1               5

<210> SEQ ID NO 123
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 123

Thr Ser Leu Ser His Ala
1               5

<210> SEQ ID NO 124
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 124

Leu His Pro Ser Arg Pro
1               5

<210> SEQ ID NO 125
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 125

Lys Ala Ala Lys Tyr Gly
1               5

<210> SEQ ID NO 126
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 126

Gly Ile Gly Pro Gly Gly
1               5

<210> SEQ ID NO 127
<211> LENGTH: 10
```

```
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 127

Asn Asn Gln Ile Asp His Ile Asp Glu Lys
1               5                   10

<210> SEQ ID NO 128
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 128

Ser Ala Gly Tyr Leu Asp Asp Val Thr Leu
1               5                   10

<210> SEQ ID NO 129
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 129

Leu Asn Arg Lys Tyr Glu Gln Ala Lys Asn
1               5                   10

<210> SEQ ID NO 130
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 130

Gln Phe Glu Gly Lys Lys Leu Met Ala Tyr
1               5                   10

<210> SEQ ID NO 131
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 131

Gly Leu Trp Asn Phe Arg Glu Lys Glu Gly
1               5                   10

<210> SEQ ID NO 132
```

```
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 132

Ala Leu Asp Pro Ala Phe Lys Ile Glu Asp
1               5                   10

<210> SEQ ID NO 133
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 133

Ser Ile Glu Ser Glu Thr Ala Ala Ser Glu
1               5                   10

<210> SEQ ID NO 134
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 134

Glu Thr Leu Phe Asn Ala Ser Gln Arg Ile
1               5                   10

<210> SEQ ID NO 135
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 135

Asn Ser Arg Asn Gln Glu Arg Leu Glu Glu
1               5                   10

<210> SEQ ID NO 136
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 136

Glu Met Asp Thr Leu Asn Glu Glu Val Val
1               5                   10
```

```
<210> SEQ ID NO 137
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 137

Asp Leu Glu Leu Ala Asp Ala Tyr Tyr Leu
1               5                   10

<210> SEQ ID NO 138
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 138

Ala Ala Gly Pro Pro Gly
1               5

<210> SEQ ID NO 139
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 139

Ala Gly Pro Val Gly Pro
1               5

<210> SEQ ID NO 140
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline
<220> FEATURE:
<221> NAME/KEY: MOD_RES
<222> LOCATION: 6
<223> OTHER INFORMATION: hydroxyproline

<400> SEQUENCE: 140

Asp Gly Arg Pro Gly Pro
1               5

<210> SEQ ID NO 141
<211> LENGTH: 6
<212> TYPE: PRT
<213> ORGANISM: Homo sapiens
<220> FEATURE:
<221> NAME/KEY: SOURCE
<222> LOCATION: 1..6
```

```
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline

<400> SEQUENCE: 141

Glu Ala Gly Arg Pro Gly
1               5

<210> SEQ ID NO 142
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline

<400> SEQUENCE: 142

Gly Ala Pro Gly Leu Gln
1               5

<210> SEQ ID NO 143
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 143

Gly Leu Asn Gly Leu Pro
1               5

<210> SEQ ID NO 144
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 6
<223> OTHER INFORMATION: hydroxyproline

<400> SEQUENCE: 144

Gly Leu Asn Gly Leu Pro
1               5

<210> SEQ ID NO 145
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
```

```
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 6
<223> OTHER INFORMATION: hydroxylysine

<400> SEQUENCE: 145

Gly Leu Pro Gly Ala Lys
1               5

<210> SEQ ID NO 146
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 5..6
<223> OTHER INFORMATION: hydroxyproline

<400> SEQUENCE: 146

Gly Pro Pro Gly Pro Pro
1               5

<210> SEQ ID NO 147
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 2..3
<223> OTHER INFORMATION: hydroxyproline

<400> SEQUENCE: 147

Gly Pro Pro Gly Pro Pro
1               5

<210> SEQ ID NO 148
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 148

Gly Val Arg Gly Leu Thr
1               5

<210> SEQ ID NO 149
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
```

```
<220> FEATURE:
<221> NAME/KEY: MOD_RES
<222> LOCATION: 2
<223> OTHER INFORMATION: hydroxyproline
<220> FEATURE:
<221> NAME/KEY: MOD_RES
<222> LOCATION: 4..5
<223> OTHER INFORMATION: hydroxyproline

<400> SEQUENCE: 149

Leu Pro Gly Pro Pro Gly
1               5

<210> SEQ ID NO 150
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxyproline

<400> SEQUENCE: 150

Leu Pro Gly Pro Pro Gly
1               5

<210> SEQ ID NO 151
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 151

Pro Gly Ala Arg Gly Pro
1               5

<210> SEQ ID NO 152
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 152

Pro Gly Lys Asp Gly Val
1               5

<210> SEQ ID NO 153
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
```

```
<223> OTHER INFORMATION: hydroxyproline
<220> FEATURE:
<221> NAME/KEY: MOD_RES
<222> LOCATION: 6
<223> OTHER INFORMATION: hydroxyproline

<400> SEQUENCE: 153

Pro Gly Pro Pro Gly Pro
1               5

<210> SEQ ID NO 154
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: hydroxyproline
<220> FEATURE:
<221> NAME/KEY: MOD_RES
<222> LOCATION: 3..4
<223> OTHER INFORMATION: hydroxyproline

<400> SEQUENCE: 154

Pro Gly Pro Pro Gly Pro
1               5

<210> SEQ ID NO 155
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: hydroxyproline

<400> SEQUENCE: 155

Pro Gly Pro Pro Gly Pro
1               5

<210> SEQ ID NO 156
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline
<220> FEATURE:
<221> NAME/KEY: MOD_RES
<222> LOCATION: 6
<223> OTHER INFORMATION: hydroxyproline

<400> SEQUENCE: 156

Arg Gly Glu Pro Gly Pro
1               5
```

```
<210> SEQ ID NO 157
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline

<400> SEQUENCE: 157

Arg Gly Leu Pro Gly Pro
1               5

<210> SEQ ID NO 158
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 158

Val Gly Pro Val Gly Ala
1               5

<210> SEQ ID NO 159
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 159

Asp Gly Leu Asn Gly Leu
1               5

<210> SEQ ID NO 160
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline

<400> SEQUENCE: 160

Ala Lys Gly Glu Pro Gly
1               5

<210> SEQ ID NO 161
<211> LENGTH: 6
<212> TYPE: PRT
<213> ORGANISM: Homo sapiens
<220> FEATURE:
<221> NAME/KEY: SOURCE
```

```
<222> LOCATION: 1..6
<223> OTHER INFORMATION: /mol_type="protein"
      /organism="Homo sapiens"

<400> SEQUENCE: 161

Ala Gly Ala Arg Gly Asn
1               5

<210> SEQ ID NO 162
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 6
<223> OTHER INFORMATION: hydroxyproline

<400> SEQUENCE: 162

Val Gly Pro Pro Gly Pro
1               5

<210> SEQ ID NO 163
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5
<223> OTHER INFORMATION: hydroxylysine

<400> SEQUENCE: 163

Gly Ala Pro Gly Lys Asp
1               5

<210> SEQ ID NO 164
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 164

Ile Gly Ser Ala Gly Pro
1               5

<210> SEQ ID NO 165
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
```

```
<400> SEQUENCE: 165

Ala Gly Ala Pro Gly Lys
1               5

<210> SEQ ID NO 166
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 166

Pro Pro Gly Pro Pro Gly
1               5

<210> SEQ ID NO 167
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline
<220> FEATURE:
<221> NAME/KEY: MOD_RES
<222> LOCATION: 5..6
<223> OTHER INFORMATION: hydroxyproline

<400> SEQUENCE: 167

Gly Pro Pro Gly Pro Pro
1               5

<210> SEQ ID NO 168
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxyproline
<220> FEATURE:
<221> NAME/KEY: MOD_RES
<222> LOCATION: 4..5
<223> OTHER INFORMATION: hydroxyproline

<400> SEQUENCE: 168

Tyr Asp Glu Lys Ser Thr
1               5

<210> SEQ ID NO 169
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
```

```
                /organism="Homo sapiens"

<400> SEQUENCE: 169

Glu Arg Gly Pro Pro Gly
1               5

<210> SEQ ID NO 170
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 170

Ile Gly Asn Val Gly Ala
1               5

<210> SEQ ID NO 171
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 171

Ala Gly Lys Glu Gly Pro
1               5

<210> SEQ ID NO 172
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 172

Ile Gly Ser Ala Gly Pro
1               5

<210> SEQ ID NO 173
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
       /organism="Homo sapiens"
<220> FEATURE:
<221> NAME/KEY: MOD_RES
<222> LOCATION: 1
<223> OTHER INFORMATION: beta bond

<400> SEQUENCE: 173

Asp Gly Leu Asn Gly Leu Pro
1               5

<210> SEQ ID NO 174
<211> LENGTH: 6
<212> TYPE: PRT
```

```
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 174

Ala Glu Gly Ser Pro Gly
1               5

<210> SEQ ID NO 175
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline

<400> SEQUENCE: 175

Ala Gly Ala Pro Gly Asp
1               5

<210> SEQ ID NO 176
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 176

Ala Gly Pro Pro Gly Pro
1               5

<210> SEQ ID NO 177
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline

<400> SEQUENCE: 177

Ala Gly Pro Pro Gly Pro
1               5

<210> SEQ ID NO 178
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
```

<400> SEQUENCE: 178

Ala Pro Gln Leu Ser Tyr
1               5

<210> SEQ ID NO 179
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxyproline

<400> SEQUENCE: 179

Ala Pro Gln Leu Ser Tyr
1               5

<210> SEQ ID NO 180
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 180

Glu Ala Gly Leu Pro Gly
1               5

<210> SEQ ID NO 181
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 181

Gly Gly Arg Tyr Tyr Arg
1               5

<210> SEQ ID NO 182
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 182

Gly Asn Phe Ala Pro Gln
1               5

<210> SEQ ID NO 183
<211> LENGTH: 6
<212> TYPE: PRT
<213> ORGANISM: Homo sapiens
<220> FEATURE:

```
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 5
<223> OTHER INFORMATION: hydroxyproline

<400> SEQUENCE: 183

Gly Asn Phe Ala Pro Gln
1               5

<210> SEQ ID NO 184
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 6
<223> OTHER INFORMATION: hydroxyproline

<400> SEQUENCE: 184

Gly Pro Ala Gly Ala Pro
1               5

<210> SEQ ID NO 185
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: hydroxyproline

<400> SEQUENCE: 185

Gly Pro Pro Gly Ala Asp
1               5

<210> SEQ ID NO 186
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 186

Gly Pro Pro Ser Ala Gly
1               5

<210> SEQ ID NO 187
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
```

```
      /organism="Homo sapiens"
<220> FEATURE:
<221> NAME/KEY: MOD_RES
<222> LOCATION: 4
<223> OTHER INFORMATION: hydroxyproline

<400> SEQUENCE: 187

Ile Gly Pro Pro Gly Pro
1               5

<210> SEQ ID NO 188
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 188

Ile Gly Pro Pro Gly Pro
1               5

<210> SEQ ID NO 189
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 3..4
<223> OTHER INFORMATION: hydroxyproline

<400> SEQUENCE: 189

Ile Gly Pro Pro Gly Pro
1               5

<210> SEQ ID NO 190
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 190

Ile Ser Val Pro Gly Pro
1               5

<210> SEQ ID NO 191
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: oxidised methionine

<400> SEQUENCE: 191
```

```
Leu Gln Gly Met Pro Gly
1               5

<210> SEQ ID NO 192
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 192

Asn Phe Ala Pro Gln Leu
1               5

<210> SEQ ID NO 193
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: hydroxyproline
<220> FEATURE:
<221> NAME/KEY: MOD_RES
<222> LOCATION: 4
<223> OTHER INFORMATION: hydroxyproline

<400> SEQUENCE: 193

Pro Gly Ala Pro Gly Pro
1               5

<210> SEQ ID NO 194
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: hydroxyproline
<220> FEATURE:
<221> NAME/KEY: MOD_RES
<222> LOCATION: 4
<223> OTHER INFORMATION: hydroxyproline

<400> SEQUENCE: 194

Pro Gly Pro Asp Gly Lys
1               5

<210> SEQ ID NO 195
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
```

```
<221> NAME/KEY: MOD_RES
<222> LOCATION: 4
<223> OTHER INFORMATION: hydroxyproline

<400> SEQUENCE: 195

Pro Gly Pro Met Gly Pro
1               5

<210> SEQ ID NO 196
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 1
<223> OTHER INFORMATION: hydroxyproline
<220> FEATURE:
<221> NAME/KEY: MOD_RES
<222> LOCATION: 3..4
<223> OTHER INFORMATION: hydroxyproline

<400> SEQUENCE: 196

Pro Gly Pro Pro Gly Ala
1               5

<210> SEQ ID NO 197
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: hydroxylysine

<400> SEQUENCE: 197

Pro Lys Gly Asn Ser Gly
1               5

<210> SEQ ID NO 198
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 198

Pro Pro Ser Ala Gly Phe
1               5

<210> SEQ ID NO 199
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
```

```
<220> FEATURE:
<221> NAME/KEY: MOD_RES
<222> LOCATION: 1
<223> OTHER INFORMATION: hydroxyproline

<400> SEQUENCE: 199

Pro Gln Leu Ser Tyr Gly
1               5

<210> SEQ ID NO 200
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 200

Pro Ser Ala Gly Phe Asp
1               5

<210> SEQ ID NO 201
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: hydroxyproline

<400> SEQUENCE: 201

Gln Gly Pro Pro Gly Pro
1               5

<210> SEQ ID NO 202
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 202

Arg Gly Arg Thr Gly Asp
1               5

<210> SEQ ID NO 203
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 203

Val Gly Ala Arg Gly Pro
1               5
```

```
<210> SEQ ID NO 204
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 204

Ala Gly Ala Gln Gly Pro
1               5

<210> SEQ ID NO 205
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 205

Ala Gly Ile Pro Gly Val
1               5

<210> SEQ ID NO 206
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 206

Ala Pro Gly Ala Pro Gly
1               5

<210> SEQ ID NO 207
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 207

Glu Arg Gly Arg Pro Gly
1               5

<210> SEQ ID NO 208
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 208

Gly Glu Arg Gly Ser Pro
1               5
```

```
<210> SEQ ID NO 209
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 209

Gly Phe Asp Gly Arg Asn
1               5

<210> SEQ ID NO 210
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 210

Gly Gly Pro Gly Ala Asp
1               5

<210> SEQ ID NO 211
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 211

Gly Leu Pro Gly Pro Pro
1               5

<210> SEQ ID NO 212
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 212

Gly Leu Pro Gly Thr Gly
1               5

<210> SEQ ID NO 213
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 213

Gly Pro Pro Gly Pro Ala
1               5
```

```
<210> SEQ ID NO 214
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 214

Gly Pro Arg Gly Pro Thr
1               5

<210> SEQ ID NO 215
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 215

Gly Ser Pro Gly Pro Ala
1               5

<210> SEQ ID NO 216
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 216

Ile Ala Gly Ile Thr Gly
1               5

<210> SEQ ID NO 217
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 217

Lys Gly Asp Pro Gly Pro
1               5

<210> SEQ ID NO 218
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 218

Lys Gly Asp Arg Gly Glu
```

```
1               5
```

<210> SEQ ID NO 219
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 219

```
Leu Lys Gly Glu Asn Gly
1               5
```

<210> SEQ ID NO 220
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 220

```
Pro Gly Glu Asn Gly Ala
1               5
```

<210> SEQ ID NO 221
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 221

```
Pro Gly Glu Arg Gly Glu
1               5
```

<210> SEQ ID NO 222
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 222

```
Pro Gly Lys Asn Gly Ala
1               5
```

<210> SEQ ID NO 223
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 223

Pro Gly Leu Lys Gly Glu
1               5

<210> SEQ ID NO 224
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 224

Pro Gly Met Arg Gly Met
1               5

<210> SEQ ID NO 225
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 225

Pro Pro Gly Lys Asp Gly
1               5

<210> SEQ ID NO 226
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 226

Pro Gln Gly Pro Lys Gly
1               5

<210> SEQ ID NO 227
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 227

Ser Pro Gly Ala Lys Gly
1               5

<210> SEQ ID NO 228
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 228

Ala Gly Gln Pro Gly Asp
1               5

<210> SEQ ID NO 229
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 229

Glu Asn Gly Ser Pro Gly
1               5

<210> SEQ ID NO 230
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 230

Gly Asp Pro Gly Pro Pro
1               5

<210> SEQ ID NO 231
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 231

Gly Glu Arg Gly Pro Pro
1               5

<210> SEQ ID NO 232
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 232

Gly Leu Pro Gly Ala Ala
1               5

<210> SEQ ID NO 233
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

```
<400> SEQUENCE: 233

Gly Pro Ala Gly Ile Pro
1               5

<210> SEQ ID NO 234
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 234

Gly Pro Pro Gly Ile Pro
1               5

<210> SEQ ID NO 235
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 235

Gly Pro Pro Gly Pro Ala
1               5

<210> SEQ ID NO 236
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 236

Gly Arg Pro Gly Leu Pro
1               5

<210> SEQ ID NO 237
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 237

Gly Ser Pro Gly Gly Pro
1               5

<210> SEQ ID NO 238
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
```

```
<400> SEQUENCE: 238

Gly Ser Pro Gly Pro Gln
1               5

<210> SEQ ID NO 239
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 239

Gly Val Pro Gly Ala Lys
1               5

<210> SEQ ID NO 240
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 240

Lys Gly Glu Pro Gly Pro
1               5

<210> SEQ ID NO 241
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 241

Pro Ala Gly Ile Pro Gly
1               5

<210> SEQ ID NO 242
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 242

Ala Gly Pro Arg Gly Pro
1               5

<210> SEQ ID NO 243
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
```

/organism="Homo sapiens"

<400> SEQUENCE: 243

Pro Gly Glu Pro Gly Pro
1               5

<210> SEQ ID NO 244
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 244

Pro Gly Lys Asp Gly Pro
1               5

<210> SEQ ID NO 245
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 245

Pro Arg Gly Ala Pro Gly
1               5

<210> SEQ ID NO 246
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 246

Arg Gly Ala Pro Gly Glu
1               5

<210> SEQ ID NO 247
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 247

Arg Gly Glu Pro Gly Pro
1               5

<210> SEQ ID NO 248
<211> LENGTH: 6
<212> TYPE: PRT
<213> ORGANISM: Homo sapiens
<220> FEATURE:
<221> NAME/KEY: SOURCE
<222> LOCATION: 1..6

<223> OTHER INFORMATION: /mol_type="protein"
       /organism="Homo sapiens"

<400> SEQUENCE: 248

Ser Gly His Pro Gly Pro
1               5

<210> SEQ ID NO 249
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 249

Ser Gly Pro Lys Gly Asp
1               5

<210> SEQ ID NO 250
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 250

Thr Gly Pro Pro Gly Pro
1               5

<210> SEQ ID NO 251
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 251

Ile Val Ile Gly Thr Gly
1               5

<210> SEQ ID NO 252
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
       /organism="Homo sapiens"

<400> SEQUENCE: 252

Gly Ile Val Ile Gly Thr
1               5

<210> SEQ ID NO 253
<211> LENGTH: 6
<212> TYPE: PRT
<213> ORGANISM: Homo sapiens
<220> FEATURE:
<221> NAME/KEY: SOURCE

```
<222> LOCATION: 1..6
<223> OTHER INFORMATION: /mol_type="protein"
      /organism="Homo sapiens"

<400> SEQUENCE: 253

Arg Arg Asn Ile Asp Ala
1               5

<210> SEQ ID NO 254
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 254

Gln Gln Gly Gly Ala Gly
1               5

<210> SEQ ID NO 255
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 255

Gln Arg Gly Ala His Gly
1               5

<210> SEQ ID NO 256
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 256

Arg Val Gly Lys Met Gly
1               5

<210> SEQ ID NO 257
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 257

His Met Gly Arg Glu Gly
1               5

<210> SEQ ID NO 258
<211> LENGTH: 6
<212> TYPE: PRT
<213> ORGANISM: Homo sapiens
<220> FEATURE:
```

```
<221> NAME/KEY: SOURCE
<222> LOCATION: 1..6
<223> OTHER INFORMATION: /mol_type="protein"
      /organism="Homo sapiens"

<400> SEQUENCE: 258

Arg Gly Ile Thr Gly Lys
1               5

<210> SEQ ID NO 259
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 259

Arg Ile Ala Val Ala Gln
1               5

<210> SEQ ID NO 260
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 260

Gln Leu Gly Thr Val Gln
1               5

<210> SEQ ID NO 261
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 261

Arg Asp Val Val Phe Leu
1               5

<210> SEQ ID NO 262
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 262

Lys Leu Thr Gly Ile Pro
1               5

<210> SEQ ID NO 263
<211> LENGTH: 6
<212> TYPE: PRT
<213> ORGANISM: Homo sapiens
```

```
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 263

Arg Ala Tyr Tyr Asn Gly
1               5

<210> SEQ ID NO 264
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 264

Glu Ile Ser Pro Asp Thr
1               5

<210> SEQ ID NO 265
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 265

Ile Glu Met Gly Gly Asn
1               5

<210> SEQ ID NO 266
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 266

Asn His Leu Val Glu Ile
1               5

<210> SEQ ID NO 267
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 267

Asn Glu Leu His Leu Asp
1               5

<210> SEQ ID NO 268
<211> LENGTH: 6
<212> TYPE: PRT
```

```
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 268

Tyr Trp Glu Val Gln Pro
1               5

<210> SEQ ID NO 269
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 269

Ile Gln Ala Ile Glu Leu
1               5

<210> SEQ ID NO 270
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 270

Thr Leu Asn Glu Leu His
1               5

<210> SEQ ID NO 271
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 271

Pro Lys Asp Leu Pro Glu
1               5

<210> SEQ ID NO 272
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 272

Phe Asn Asn Pro Val Pro
1               5

<210> SEQ ID NO 273
<211> LENGTH: 6
```

```
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 273

Asp Ile Ser Glu Leu Arg
1               5

<210> SEQ ID NO 274
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 274

Ala Phe Asp Gly Leu Lys
1               5

<210> SEQ ID NO 275
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 275

Pro Asn Leu Pro Ser Ser
1               5

<210> SEQ ID NO 276
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 276

Val Pro Lys Asp Leu Pro
1               5

<210> SEQ ID NO 277
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 277

Tyr Glu Asn Trp Arg Pro
1               5

<210> SEQ ID NO 278
```

```
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 278

His Asp Tyr Gln Trp Ile
1               5

<210> SEQ ID NO 279
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 279

Lys Thr Phe Gly Lys Met
1               5

<210> SEQ ID NO 280
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 280

Phe Ser Ala Gly Glu Asp
1               5

<210> SEQ ID NO 281
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 281

Val Gly Pro Leu Val Thr
1               5

<210> SEQ ID NO 282
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 282

Asp His Ile Asp Glu Lys
1               5
```

```
<210> SEQ ID NO 283
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 283

Leu Ser His Ala Phe Gly
1               5

<210> SEQ ID NO 284
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 284

Thr Ser Leu Ser His Ala
1               5

<210> SEQ ID NO 285
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 285

Leu His Pro Ser Arg Pro
1               5

<210> SEQ ID NO 286
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 286

Lys Ala Ala Lys Tyr Gly
1               5

<210> SEQ ID NO 287
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 287

Gly Ile Gly Pro Gly Gly
1               5
```

```
<210> SEQ ID NO 288
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 288

Leu Met Asp Glu Thr Met
1               5

<210> SEQ ID NO 289
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 289

Met Glu Glu Met Gly Ser
1               5

<210> SEQ ID NO 290
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 290

Arg Leu Asp Glu Val Lys
1               5

<210> SEQ ID NO 291
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 291

Thr Pro Val Ala Glu Glu
1               5

<210> SEQ ID NO 292
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 292

Leu Asp Asp Val Thr Leu
1               5
```

```
<210> SEQ ID NO 293
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 293

Tyr Glu Gln Ala Lys Asn
1               5

<210> SEQ ID NO 294
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 294

Gln Phe Glu Gly Lys Lys
1               5

<210> SEQ ID NO 295
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 295

Gly Leu Trp Asn Phe Arg
1               5

<210> SEQ ID NO 296
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 296

Ser Ile Glu Ser Glu Thr
1               5

<210> SEQ ID NO 297
<211> LENGTH: 6
<212> TYPE: PRT
<213> ORGANISM: Homo sapiens
<220> FEATURE:
<221> NAME/KEY: SOURCE
<222> LOCATION: 1..6
```

```
<223> OTHER INFORMATION: /mol_type="protein"
     /organism="Homo sapiens"

<400> SEQUENCE: 297

Ala Phe Lys Ile Glu Asp
1               5

<210> SEQ ID NO 298
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
     /organism="Homo sapiens"

<400> SEQUENCE: 298

Asn Ala Ser Gln Arg Ile
1               5

<210> SEQ ID NO 299
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
     /organism="Homo sapiens"

<400> SEQUENCE: 299

Asn Ser Arg Asn Gln Glu
1               5

<210> SEQ ID NO 300
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
     /organism="Homo sapiens"

<400> SEQUENCE: 300

Leu Asn Glu Glu Val Val
1               5

<210> SEQ ID NO 301
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
     /organism="Homo sapiens"

<400> SEQUENCE: 301

Ala Asp Ala Tyr Tyr Leu
1               5

<210> SEQ ID NO 302
<211> LENGTH: 7
<212> TYPE: PRT
<213> ORGANISM: Homo sapiens
<220> FEATURE:
<221> NAME/KEY: SOURCE
```

```
<222> LOCATION: 1..7
<223> OTHER INFORMATION: /mol_type="protein"
      /organism="Homo sapiens"

<400> SEQUENCE: 302

Tyr Asp Gly Lys Gly Val Gly
1               5

<210> SEQ ID NO 303
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 303

Glu Lys Ala His Asp Gly Gly Arg
1               5

<210> SEQ ID NO 304
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 304

Ser Val Thr Gln Ile Glu
1               5
```